(12) United States Patent
Oppermann et al.

(10) Patent No.: US 7,429,484 B2
(45) Date of Patent: *Sep. 30, 2008

(54) NUCLEIC ACID MOLECULES ENCODING OSTEOGENIC PROTEINS

(75) Inventors: Hermann Oppermann, Medway, MA (US); Thangavel Kuberasampath, Medway, MA (US); David C. Rueger, West Roxbury, MA (US); Engin Ozkaynak, Milford, MA (US)

(73) Assignee: Stryker Corporation, Kalamazoo, MI (US)

( * ) Notice: Subject to any disclaimer, the term of this patent is extended or adjusted under 35 U.S.C. 154(b) by 29 days.

This patent is subject to a terminal disclaimer.

(21) Appl. No.: 11/331,855

(22) Filed: Jan. 13, 2006

(65) Prior Publication Data

US 2006/0198835 A1      Sep. 7, 2006

Related U.S. Application Data

(60) Division of application No. 09/754,831, filed on Jan. 3, 2001, now Pat. No. 7,078,221, which is a continuation of application No. 08/375,901, filed on Jan. 20, 1995, now Pat. No. 6,261,835, which is a division of application No. 08/145,812, filed on Nov. 1, 1993, now Pat. No. 5,750,651, which is a division of application No. 07/995,345, filed on Dec. 22, 1992, now Pat. No. 5,258,494, which is a division of application No. 07/315,342, filed on Feb. 23, 1989, now Pat. No. 5,011,691.

(51) Int. Cl.
*C12N 5/10*           (2006.01)
*C12N 1/11*           (2006.01)
*C12N 1/13*           (2006.01)
*C12N 1/21*           (2006.01)
*C12N 1/19*           (2006.01)
*C12N 15/11*          (2006.01)
*C12N 15/12*          (2006.01)

(52) U.S. Cl. ............... 435/325; 435/252.3; 435/254.11; 536/23.1; 536/23.5

(58) Field of Classification Search .................. None
See application file for complete search history.

(56) References Cited

U.S. PATENT DOCUMENTS

| | | | | |
|---|---|---|---|---|
| 5,250,302 A | * | 10/1993 | Oppermann et al. | 424/422 |
| 5,585,237 A | * | 12/1996 | Oppermann et al. | 435/6 |
| 5,614,385 A | * | 3/1997 | Oppermann et al. | 435/69.4 |
| 5,670,336 A | * | 9/1997 | Oppermann et al. | 435/69.1 |
| 5,712,119 A | * | 1/1998 | Oppermann et al. | 435/69.4 |
| 5,863,758 A | * | 1/1999 | Oppermann et al. | 435/69.1 |
| 6,071,695 A | * | 6/2000 | Ozkaynak et al. | 435/6 |
| 6,261,835 B1 | * | 7/2001 | Oppermann et al. | 435/320.1 |
| 7,078,221 B2 | * | 7/2006 | Oppermann et al. | 435/252.3 |

* cited by examiner

*Primary Examiner*—Elizabeth C Kemmerer
(74) *Attorney, Agent, or Firm*—K & L Gates LLP

(57) ABSTRACT

Disclosed are 1) osteogenic devices comprising a matrix containing osteogenic protein and methods of inducing endochondral bone growth in mammals using the devices; 2) amino acid sequence data, amino acid composition, solubility properties, structural features, homologies and various other data characterizing osteogenic proteins, 3) methods of producing osteogenic proteins using recombinant DNA technology, and 4) osteogenically and chondrogenically active synthetic protein constructs.

16 Claims, 28 Drawing Sheets

FIG. 1A-1

```
            10         20         30         40         50         60         70
GGAGGTATAGGAGCTCTCTTCGATTTTAGCAAACCAGGAGTCCGAAGATCTAAGGAGAGCTGGGGGTTGACTCC
            SacI                                        BglII
            85         95        105        115        125        135        145
GAGAGCTCGAGCAGTCCCCAAGACCTGGTCTTGACTCACGAGTTAGACTCCACTCAGAGGCTGACTGTCTCCAGG
SacI       PflMI
XhoI            Tth111I
           160        170        180        190        200        210        220
GTCTACACCTCTAAGGGCGACACTGGGCTCAAGCAGACTGCCGTTTCTATATGGATGAGCCTTCACAGGGCAG
           235        245        255        265        275        285        295
CCAGTGGGATGGGTTGAGGTTGGCTGTAGACATCAGAAACCCAAGTCAAATGCGTTCAACCAGTAGAAAATT
           310        320        330        340        350        360        370
CACCAGCCCGCAGAGCTAAGGTGGGTGGACATTAGGGTTGGTTGATCCAGGAGCTCAACAGTGTCCTCTGAGCC
                                                       SacI
           385        395        405        415        425        435        445
CCAGCTCCTTCTGCCCCACCCCACCACCATCTTCAGTGCTGCTTCCTCTCTCCAAGGCCACAGCTGTAGTTGGCCAGGGGG
                                                      PvuII    BalI
                                                                    BglI
           460        470        480        490        500        510        520
GCTTCATTATTTTTGCTCCTGGGCAGTAGGAGGAAGAGAAATGAATGTCTCTCACATGGGTCTTTCTTAGGAATGT
                                                         NcoI
           535        545        555        565        575        585        595
GGGAACTTTTCCAGAAGTCTCTATGTCTTTTAGTTGTTGGGTCACTTGCCCTTCCTGAACCACTTCCTGAC
           610        620        630        640        650        660        670
TCCTGGACAGGATGTGCACTGATGAGCTTAGCTTGGGATCTAATAGTGACTTTACAAAGCCTCTTTGAGAAGG
           685        695        705        715        725        735        745
TGACATTGGAACCAAGGCTTGAGCAGACAACACAAAGATTGCAGGGGCATTGCAGTGGAGGAAACGGCAC
ApaLI       EspI
           760        770        780        790        800        810        820
ATGCAAGAGCCCTGCGTGGAGTGAGCTTGGTTTGGTCAATCAGTTGTCAGAGCACACCGGGCCCTGTCAGCA
                                                                  ApaI
                                                                  EcoO
                                                         BspMI-
```

FIG. 1A-2

```
         835       845       855       865       875       885       895
GGCACAGCCTGGGCCTGCTCTGAGTATGACACAGAGAGCCCCTGGGAAGTTGTAGGTGAGGAAAGACAGTCATGA
         910       920       930       940       950       960       970
CTAGGAAAAAGCAATCCCTCTGTTGTGGGGTGGAAGGAAGGTTGCAGTGTGTGAGAGAGAAGACAAGACAGAC
         985       995      1005      1015      1025      1035      1045
AGACAGAGACACTTCTCAATGTTTACAAGTGCTTCAGGCCCTGACCCGAATGCTTCCAAATTTACGTAGTTCTGGAAA
                                                 EcoO              SnaBI
         1060      1070      1080      1090      1100      1110      1120
ACCCCCCTGTATCATTTTCACTACTCAAAGAAACCTCGGAGTGTTTTCTTCTGAAAGGTCATCAGGTTTTGACTC
                                         BsmI+
         1135      1145      1155      1165      1175      1185      1195
TCTGCTCTCATTTCTTCTTGCTGGTGGTGATGGTTGCTGTGTCCCAGGCCCTGTCCCGCATCCTCTTGCCC
                                                           EcoO
         1210      1220      1230      1240      1250      1260      1270
CTGCAGAGGGATGAGTGTGTTGGGGCCCTCACGAGTTGAGGTTGTTCATAAGCAGATCTCTTTGAGCAGGGCGCCT
PstI              EcoO                                                   NarI Ps
         1285      1295      1305      1315      1325      1335      1345
GCAGTGGCCTTGTGTGAGGCTGGAGGGGTTTCGATTCCCTTATGGAATCCAGGCAGATGTAGCATTAAACAACA
                                                  BglII                    DraI
         1360      1370      1380      1390      1400      1410      1420
CACGTGTATAAAAGAAACCAGTGTCCCAGAAGGTTCCAGAAAGTATTATGGATAAAGACTACATGAGAGGAA
         1435      1445      1455      1465      1475      1485      1495
TGGGGCATTGGCACCTCCCTTAGTAGGGCCTTTGCTGGGGTAGAAAATGAGTTTTAAGGCAGGTTAGACCCCTCGA
                                                                   BspMI-
         1510      1520      1530      1540      1550      1560      1570
ACTGGCTTTTGAATCGGGAAAATTTACCCCCCAGCCGTCTGTCTTCATTGCTTCACATCACTGCTAAGATG
         1585      1595      1605      1615      1625      1635      1645
GAGGAACTTGATGTGTGGTCTGTTTCTTCTCCCTACTGGCTTCTTGCTTCCTTGTCAATGCAGAGAA
         1660      1670      1680      1690      1700      1710      1720
CAGCAGCAGGCACCAGAGGCCTTGTAAGAAGCACGAGCTGTATGTCAGCTTCCGAGACCTGGGCTGGCAGG
         1735      1745      1755      1765      1775      1785      1795
TAAGGGGCTGGCTGGGTCTGTCTTGGGTGTGGGCCCTCTGGGCCTCCCACAGGCAGCGGGTGTGTGCTCA
                ApaI
                EcoO
                StuI                                                 BspMI
```

FIG. 1A-3

```
         1810      1820      1830      1840      1850      1860      1870
GTCTTGTTTCTCATCTCTGCCAGTCTGCCAGTTAAGACTCCAGTATCAAGTGGCCTCGCTAGGGAAGGGTACTTGGCTAAGGA
          1885      1895      1905      1915      1925      1935      1945
TACAGGG......(APPROX. 1000 BASES)..........GGGAGCCAGACATGGGTGATGCCATTATGA
    1960      1970      1980      1990      2000      2010      2020
GTTATTAGCCTCTCTGGCAGGTGGGCAAACCGAGGCATGGAGGTTTGTTTAAGTGAACTGCCAGTGTGACCA
     BglI  BspMI-                                                   Dr
                                                                    PflI
         2035      2045      2055      2065      2075      2085      2095
CCTAGTGGGTAGAGCTGATGATTGCCTCACACCGGAGCTCCTTCCTGTGCCGCGTTCTGTCCAGAAGACACAGC
aIII                                   SacI                             N
MI
         2110      2120      2130      2140      2150      2160      2170
CATGGATGTCCATTTAGGATCAGCCAAGCCCCGTCTGTCCTTCATTTTATTTTATGTTTTTTAGAAATGGG
coI
         2185      2195      2205      2215      2225      2235      2245
GTCTGCTCTGTCACCCAGGCTGGGTGCAGTGGTGTGATCATAGCTCACCGCAGCTTTGACGCCCGTCTTCCCACT
                                                                    Tth111I
         2260      2270      2280      2290      2300      2310      2320
CAGTCTACTAAGCTTGGACTATAGGCCAAGACTATAGAGTGGTCCTTCTTTCCATTCTCTTTGGACCATGAGAGG
         HindIII                                               BstXI
         2335      2345      2355      2365      2375      2385      2395
CCACCCATGTTTCCTGCCCCCTGCTGGGCCTGCTCAGAAGGCATGGTCTGAGGCTTTCACCTTGTCGTGAG
         ApaI
         EcoO
         2410      2420      2430      2440      2450      2460      2470
CCTTCGTGGTGGTTCTTTCAGCATGGGTTGGGATGCTGTGCTCAGGCTTCTGCATGGTTTCCCACACTCTCTT
         2485      2495      2505      2515      2525      2535      2545
CTCCTCCTCAGGACTGGATCATCGCGCTGAAGGCTACGCGCTACTACTGTGAGGGGAGTGTGCCTTCCCTC
MstII                              BssHII
         2560      2570      2580      2590      2600      2610      2620
TGAACTCCTACATGAACGCCACCACGCCCATCGTGCAGACGCTGGTGGGTGTCACGCCATCTTGGGGTGTGG
         2635      2645      2655      2665      2675      2685      2695
TCACCTGGCCGGGCCAGGCTGCGGGCCACCAGATCCTGCCTCCAAGCTGGGGCTGAGTAGATGTCAGCCC
tEII  BglI                                        EcoO                Bs
```

FIG. 1A-4

```
       2710      2720      2730      2740      2750      2760      2770
ATTGCCATGTCATGACTTTTGGGGGCCCCTTGCGCCGTTAAAAAAATCAAAAATTGTACTTTATGACTGGTTT
                         ApaI
                         EcoO
       2785      2795      2805      2815      2825      2835      2845
GGTATAAAGAGGAGTATAATCTTCGACCCTGGAGTTCATTTATTTCCTAATTTTTAAAGTAACTAAAAGTTGT
                                                        DraI
       2860      2870      2880      2890      2900      2910      2920
ATGGGCTCCTTTGAGGATGCTTGTAGTATTGTGGGTGCTGGTTACGGTGCCTAAGAGCACTGGGCCCCTGCTTCA
                                                              ApaI
                                                              EcoO
       2935      2945      2955      2965      2975      2985      2995
TTTTCCAGTAGAGGAAACAGGTAAACAGATGAGAAATTTCAGTGAGGGCACAGTGATCAGAAGGCGGGCCAGCAG
       3010      3020      3030      3040      3050      3060      3070
GATAATGGGATGGAGAGATGAGTGGGACCCATGGGCCATTTCAAGTTAAATTCAGTCGGGTCACCAGGAAGAT
                              EcoO NcoI                        BstEII
       3085      3095      3105      3115      3125      3135      3145
TCCATGTGATAATGAGATTAACGTGCCCAGTCACGGCGACACTCAGTAGGTGTTATTCCTGCTCTGCCAACAGCA
       3160      3170      3180      3190      3200      3210      3220
ACCATAGTTGATAAGAGCTGTTAGGGATTTTGTCCTTTTGCTTAGAATCCAAGGTTCAAGGACCTTGGTTATGTA
       3235      3245      3255      3265      3275      3285      3295
GCTCCCTGTCATGAACATCATCTGAGCCTTTCCTGCCTACTGATCATCCACCCTGCCTTGAATGCTTCTAGTGAC
                                                                 EcoO
                                                                 BsmI+
       3310      3320      3330      3340      3350      3360      3370
AGAGAGCTCACTACCAGGACTACTCCCCTCCTCCTTTCATTAGTAATCTGCCTCCTCTTTCTTTCTGTCCCTGTCCCTGT
       SacI
       3385      3395      3405      3415      3425      3435      3445
GTGTTAAGTCCTGGAGAAAATCTCATCTATCCCTTTCATTGATTCTGCTCTTTGAGGGCAGGGGTTTTGTTT
       3460      3470      3480      3490      3500      3510      3520
CTTTGTTTGTTTTTAAGTGTTGGTTTCCAAAGCCCTTGCTCCCCCTCCTCAATTGAAACTTCAAAGCCCTCAT
       3535      3545      3555      3565      3575      3585      3595
TGGGATTGAAGGTCCTTAGGCTGTGAAACAGAAGAGTCCTCCCCAACCTGTTCCCTGGCCTGGATGTGCTGTGCTG
       EcoOMstII
```

FIG. 1A-5

```
      3610       3620       3630       3640       3650       3660       3670
TGCCAGTATCCCCTGGAAGGTGCCAGGCATGTCTCCCCGGCTGCCAGGGACACATCTCTATCCTTCTCCAACCC
    3685       3695       3705       3715       3725       3735       3745
CTGCCTTCATGGCCCATGGAACAGGAGTGCCATGCCCCTGTGTCACCTACTTCCATCAGTATTCACCAGAGAT
   BglI    NcoI                           ApaLI                         BglI
     3760       3770       3780       3790       3800       3810       3820
CTGCAGGATCAAAGTGAATTCTCCAGGGATTGTGAAATGATGCGATTGTGGTCATGTTTAAAGGGGGCAACTGT
  I         EcoRI                                           DraI
 PstI
     3835       3845       3855       3865       3875       3885       3895
CTTCTAGAGAGTCCTGATGAATGCTTCCAGAGAAATGAGCTGGAATTTGCTTAAAATCATTCAAG
      XbaI                                                DraI
     3910       3920       3930       3940       3950       3960       3970
GTGGAGCAGTGGGGAAGGTATGTGATGTTGAAGAGTTTGAAATTGTCCATCATAAAATGTGTAAAAAGCATGCT
    BspMI-                                                            SphI
         3985       3995       4005       4015       4025       4035       4045
GGCCTATGTCAGCAGTCACAGCCTGGAGGTGGTAACAGAGTGCCAGTCACTGATGCTCAAGCCTGGCACCTACAG
         4060       4070       4080       4090       4100       4110       4120
TTGCTGGAAACCCAGAAGTTTCACGTTGAAGCAACAGGACAGTGGAATCTCTGGCCCTGTCTTGAACACGTGGC
         4135       4145       4155       4165       4175       4185       4195
AGATCTGCTAACACTGATCTTGGTTGGCTGCCGTCAGCTTAGGTTGAGTGGCGGTCTCTTCCCTTAGTTGCTTAGT
 BglII
         4210       4220       4230       4240       4250       4260       4270
CCCCGTCTATTCCCTATTGTCTTACCCTCGGTCTCTATTTTGCTCTTATCAGTGGACCTCACGAGGCACTCATAGGCATTT
         4285       4295       4305       4315       4325       4335       4345
GAGTCTATGTGTCCCGTGTCCCACATCCTCTGTAAGGTGCAGAGAAGTCCATGAGCAAGATGGAGCACTTCTAGTG
         4360       4370       4380       4390       4400       4410       4420
GGTCCAAGTCAGGGACACTATTCAGCAATCTACAGTGCACAGGGCAGTTCCCAACAGAGAATTACCTGGTCCTG
               ApaLI
         4435       4445       4455       4465       4475       4485       4495
AATGTCGGATCTGGCCCTTCCCTTCCCCACTGTATAATGTGAAAACCCTCTATGCTTTGTTCCCTTGTCTGCAAA
         4510       4520       4530       4540       4550       4560       4570
ACAGGGATAATCCCAGAACTGAGTTGTCCATGTAAAGTGCTTAGAACAGGAGTGCTTGGCTTGGGGAGTGTCAC
                                                                         Bs
```

FIG. 1A-6

```
     4585      4595      4605      4615      4625      4635      4645
CTGCAGTCATTCATTATGCCCAGACAGGATGTTTCTTTATAGAAACGTGGAGGCCAGTTAGAACGACTCACCGCT
pMI+
PstI
     4660      4670      4680      4690      4700      4710      4720
TCTCACCACTGCCCATGTTTGGTGTGTTTCAGGTCCACTTCATCAACCCGGAAACGGTGCCCAAGCCCTGCT
                  PflMI
     4735      4745      4755      4765      4775      4785      4795
GTGCGCCACGCAGCTCAATGCCATCTCCGTCCTCTACTTCGATGACAGTCCAACGTCATCCTGAAGAAATACA
             4810      4820      4830      4840
GAAACATGGTGGTCCGGGCCTGTGGCTGCCACTAGCTCCTCCGA
```

FIG. 1B

```
CONSENSUS PROBE   20        30        40        50        60        70
              GATCCTAATGGGCTGTACGTGGACTTCCAGCGCGACGTGGACGACTGGATCATCGCCCCGTCG
                  ** *** ** ********            ** *** ******************** **
OP4           TGTAAGAAGCACGAGAGCTGTATGTCAGCTTCCGAGACCTGGCTGCAGGACTGGATCATCGGCCTGAAG
                 28        38        48        58        68        78        88

80        90       100       110       120       130       140
              ACTTCGACGCGCCTACTACTGCTCCGGAGCCTGCCAGTTCCCCCTCTGCGGATCACTTCAACAGCACCAACCA
              ** **    ********      **          *****        ** ***    ***********
GCTACGCGCGCTACTACTGTGAGGGGAGTGTGCCTTCCCCTGAACTCCTACATGAACGCCACCAACCA
                 98       108       118       128       138       148       158

150       160       170       180       190       200       210
              CGCCGTGGTGCAGACCCTGGTGAACAACATGAACCCCGGCAAGGTACCAAGCCCTGCTGCCCACC
              ****  ********  ***** *****  *** *****          *** ************* ******
CGCCATCGTGCAGAACGCTGGTCCACTTCATCAACCCGAAACGGTGCCAAGCCCTGCTGCCCACG
                168       178       188       198       208       218       228

220       230       240       250       260       270       280
              GAGCTGTCCGCCATCAGCATGCTGTACCTGGACGAGAATTCCACCGTGGTGCTGAAGAACTACCAGGAGA
              ****  ******   ** ***     ** *** **  **        ******** *** *
CAGCTCAATGCCATCTCCGTCTCCTACTTCGATGACAGTCCAACGTCATCCTGAAGAAATACAGAAACA
                238       248       258       268       278       288       298

290       300       310
              TGACCGGTCCGGGCTGCGGGGCTGCCGCTAACTGCA
              **  ** *** ******* *** ************
TGGTGGTCCGGGCCCTGTGGCTGCCACTAGCTCCT
                308       318       328
```

FIG. 3A  FIG. 3B     FIG. 4A  FIG. 4B
FIG. 5
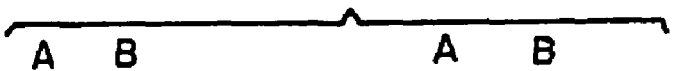
A   B         A   B
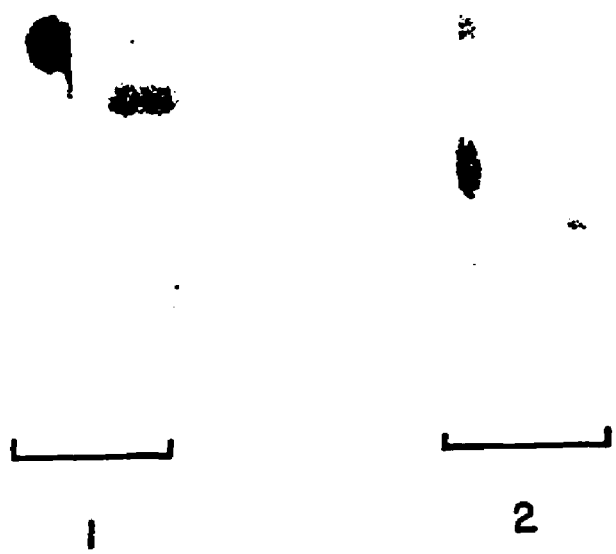
1            2

—— NON-REDUCIBLE 30K

—— 18K SUBUNIT
—— 16K SUBUNIT

FIG. 13

```
         10        20        30        40        50
GATCCTAATGGGCTGTACGTGGACTTCCAGCGCGACGTGGGCTGGGACGA
  D  P  N  G  L  Y  V  D  F  Q  R  D  V  G  W  D  D 60        70        80        90       100
CTGGATCATCGCCCCCGTCGACTTCGACGCCTACTACTGCTCCGGAGCCT
  W  I  I  A  P  V  D  F  D  A  Y  Y  C  S  G  A 110       120       130       140       150
GCCAGTTCCCCTCTGCGGATCACTTCAACAGCACCAACCACGCCGTGGTG
  C  Q  F  P  S  A  D  H  F  N  S  T  N  H  A  V  V 160       170       180       190       200
CAGACCCTGGTGAACAACATGAACCCCGGCAAGGTACCCAAGCCCTGCTG
  Q  T  L  V  N  N  M  N  P  G  K  V  P  K  P  C  C 210       220       230       240       250
CGTGCCCACCGAGCTGTCCGCCATCAGCATGCTGTACCTGGACGAGAATT
  V  P  T  E  L  S  A  I  S  M  L  Y  L  D  E  N 260       270       280       290       300
CCACCGTGGTGCTGAAGAACTACCAGGAGATGACCGTGGTGGGCTGCGGC
  S  T  V  V  L  K  N  Y  Q  E  M  T  V  V  G  C  G

310
TGCCGCTAACTGCAG
  C  R  *
```

| COP1 | COP3 | COP5 | COP7 | :VG1 | DPP | OP1 | CBMP2 a) b) | CBMP3 :(bov) | beta-Inhibin a) b) | TGF-beta 1 2 3 | :MIS Inhib: alpha | consensus choices |
|---|---|---|---|---|---|---|---|---|---|---|---|---|
| P | N | P P | P P> | : | : | : | : | : | : | C

COP-5 fusion protein

```
         10        20        30        40        50
ATGAAAGCAATTTTCGTACTGAAAGGTTCACTGGACAGAGATCTGGACTC
 M  K  A  I  F  V  L  K  G  S  L  D  R  D  L  D  S
                                        BglII 60        70        80        90       100
TCGTCTGGATCTGGACGTTCGTACCGACCACAAAGACCTGTCTGATCACC
 R  L  D  L  D  V  R  T  D  H  K  D  L  S  D  H 110       120       130       140       150
TGGTTCTGGTCGACCTGGCTCGTAACGACCTGGCTCGTATCGTTACTCCC
 L  V  L  V  D  L  A  R  N  D  L  A  R  I  V  T  P
          SalI                                  Sma 160       170       180       190       200
GGGTCTCGTTACGTTGCGGATCTGGAATTCATGGCTGACAACAAATTCAA
 G  S  R  Y  V  A  D  L  E  F  M  A  D  N  K  F  N
 I                    EcoRI 210       220       230       240       250
CAAGGAACAGCAGAACGCGTTCTACGAGATCTTGCACCTGCCGAACCTGA
 K  E  Q  Q  N  A  F  Y  E  I  L  H  L  P  N  L
             MluI        BglII      BspMI+

260       270       280       290       300
ACGAAGAGCAGCGTAACGGCTTCATCCAAAGCTTGAAGGATGAGCCCTCT
 N  E  E  Q  R  N  G  F  I  Q  S  L  K  D  E  P  S
                                HindIII 310       320       330       340       350
CAGTCTGCGAATCTGCTAGCGGATGCCAAGAAACTGAACGATGCGCAGGC
 Q  S  A  N  L  L  A  D  A  K  K  L  N  D  A  Q  A
             NheI                         FspI 360       370       380       390       400
ACCGAAATCGGATCAGGGGCAATTCATGGCTGACAACAAATTCAACAAGG
 P  K  S  D  Q  G  Q  F  M  A  D  N  K  F  N  K 410       420       430       440       450
AACAGCAGAACGCGTTCTACGAGATCTTGCACCTGCCGAACCTGAACGAA
 E  Q  Q  N  A  F  Y  E  I  L  H  L  P  N  L  N  E
             MluI        BglII      BspMI+

460       470       480       490       500
GAGCAGCGTAACGGCTTCATCCAAAGCTTGAAGGATGAGCCCTCTCAGTC
 E  Q  R  N  G  F  I  Q  S  L  K  D  E  P  S  Q  S
                             HindIII
```

*FIG. 21B-1*

```
        510        520        530        540        550
TGCGAATCTGCTAGCGGATGCCAAGAAACTGAACGATGCGCAGGCACCGA
  A  N  L  L  A  D  A  K  K  L  N  D  A  Q  A  P
      NheI                          FspI 560        570        580        590        600
AGGATCCTAATGGGCTGTACGTCGACTTCAGCGACGTGGGCTGGGACGAC
  K  D  P  N  G  L  Y  V  D  F  S  D  V  G  W  D  D
  BamHI              SalI 610        620        630        640        650
TGGATTGTGGCCCCACCAGGCTACCAGGCCTTCTACTGCCATGGCGAATG
  W  I  V  A  P  P  G  Y  Q  A  F  Y  C  H  G  E  C
                        StuI          NcoI    BsmI+

660        670        680        690        700
CCCTTTCCCGCTAGCGGATCACTTCAACAGCACCAACCACGCCGTGGTGC
  P  F  P  L  A  D  H  F  N  S  T  N  H  A  V  V
            NheI                      DraIII
                                      PflMI 710        720        730        740        750
AGACCCTGGTGAACTCTGTCAACTCCAAGATCCCTAAGGCTTGCTGCGTG
  Q  T  L  V  N  S  V  N  S  K  I  P  K  A  C  C  V
                              MstII 760        770        780        790        800
CCCACCGAGCTGTCCGCCATCAGCATGCTGTACCTGGACGAGAATGAGAA
  P  T  E  L  S  A  I  S  M  L  Y  L  D  E  N  E  K
                          SphI 810        820        830        840        850
GGTGGTGCTGAAGAACTACCAGGAGATGGTAGTAGAGGGCTGCGGCTGCC
  V  V  L  K  N  Y  Q  E  M  V  V  E  G  C  G  C
              PflMI

860
GCTAACTGCAG
  R  *
     PstI
```

*FIG. 21B-2*

SEQUENCE LISTING

<160> NUMBER OF SEQ ID NOS: 72

<210> SEQ ID NO 1
<211> LENGTH: 96
<212> TYPE: PRT
<213> ORGANISM: Artificial Sequence
<220> FEATURE:
<223> OTHER INFORMATION: Biosynthetic Protein COP5

<400> SEQUENCE: 1

Leu Tyr Val Asp Phe Ser Asp Val Gly Trp Asp Asp Trp Ile Val Ala
1               5                   10                  15

Pro Pro Gly Tyr Gln Ala Phe Tyr Cys His Gly Glu Cys Pro Phe Pro
                20                  25                  30

Leu Ala Asp His Phe Asn Ser Thr Asn His Ala Val Val Gln Thr Leu
            35                  40                  45

Val Asn Ser Val Asn Ser Lys Ile Pro Lys Ala Cys Cys Val Pro Thr
        50                  55                  60

Glu Leu Ser Ala Ile Ser Met Leu Tyr Leu Asp Glu Asn Glu Lys Val
65                  70                  75                  80

Val Leu Lys Asn Tyr Gln Glu Met Val Val Glu Gly Cys Gly Cys Arg
                85                  90                  95

<210> SEQ ID NO 2
<211> LENGTH: 96
<212> TYPE: PRT
<213> ORGANISM: Artificial Sequence
<220> FEATURE:
<223> OTHER INFORMATION: Biosynthetic protein COP7

<400> SEQUENCE: 2

Leu Tyr Val Asp Phe Ser Asp Val Gly Trp Asn Asp Trp Ile Val Ala
1               5                   10                  15

Pro Pro Gly Tyr His Ala Phe Tyr Cys His Gly Glu Cys Pro Phe Pro
                20                  25                  30

Leu Ala Asp His Leu Asn Ser Thr Asn His Ala Val Val Gln Thr Leu
            35                  40                  45

Val Asn Ser Val Asn Ser Lys Ile Pro Lys Ala Cys Cys Val Pro Thr
        50                  55                  60

Glu Leu Ser Ala Ile Ser Met Leu Tyr Leu Asp Glu Asn Glu Lys Val
65                  70                  75                  80

Val Leu Lys Asn Tyr Gln Glu Met Val Val Glu Gly Cys Gly Cys Arg
                85                  90                  95

<210> SEQ ID NO 3
<211> LENGTH: 97
<212> TYPE: PRT
<213> ORGANISM: Artificial Sequence
<220> FEATURE:
<223> OTHER INFORMATION: Biosytheic protein capable of inducing
     endochondral bone formation
<220> FEATURE:
<221> NAME/KEY: misc_feature
<222> LOCATION: (2)..(2)
<223> OTHER INFORMATION: wherein Xaa at position 2 is any amino acid
<220> FEATURE:
<221> NAME/KEY: misc_feature
<222> LOCATION: (4)..(4)
<223> OTHER INFORMATION: wherein Xaa at position 4 is any amino acid
<220> FEATURE:
<221> NAME/KEY: misc_feature
<222> LOCATION: (6)..(6)

```
<223> OTHER INFORMATION: wherein Xaa at position 6 is any amino acid
<220> FEATURE:
<221> NAME/KEY: misc_feature
<222> LOCATION: (8)..(8)
<223> OTHER INFORMATION: wherein Xaa at postion 8 is any amino acid
<220> FEATURE:
<221> NAME/KEY: misc_feature
<222> LOCATION: (11)..(11)
<223> OTHER INFORMATION: wherein Xaa at position 11 is any amino acid
<220> FEATURE:
<221> NAME/KEY: misc_feature
<222> LOCATION: (12)..(12)
<223> OTHER INFORMATION: wherein Xaa at position 12 is any amino acid
<220> FEATURE:
<221> NAME/KEY: misc_feature
<222> LOCATION: (14)..(14)
<223> OTHER INFORMATION: wherein Xaa at position 14 is any amino acid
<220> FEATURE:
<221> NAME/KEY: misc_feature
<222> LOCATION: (15)..(15)
<223> OTHER INFORMATION: wherein Xaa at position 15 is any amino acid
<220> FEATURE:
<221> NAME/KEY: misc_feature
<222> LOCATION: (16)..(16)
<223> OTHER INFORMATION: wherein Xaa at position 16 is any amino acid
<220> FEATURE:
<221> NAME/KEY: misc_feature
<222> LOCATION: (18)..(18)
<223> OTHER INFORMATION: wherein Xaa at position 18 is any amino acid
<220> FEATURE:
<221> NAME/KEY: misc_feature
<222> LOCATION: (20)..(20)
<223> OTHER INFORMATION: wherein Xaa at position 20 is any amino acid
<220> FEATURE:
<221> NAME/KEY: misc_feature
<222> LOCATION: (21)..(21)
<223> OTHER INFORMATION: wherein Xaa at position 21 is any amino acid
<220> FEATURE:
<221> NAME/KEY: misc_feature
<222> LOCATION: (23)..(23)
<223> OTHER INFORMATION: wherein Xaa at position 23 is any amino acid
<220> FEATURE:
<221> NAME/KEY: misc_feature
<222> LOCATION: (26)..(26)
<223> OTHER INFORMATION: wherein Xaa at position 26 is any amino acid
<220> FEATURE:
<221> NAME/KEY: misc_feature
<222> LOCATION: (28)..(28)
<223> OTHER INFORMATION: wherein Xaa at position 28 is any amino acid
<220> FEATURE:
<221> NAME/KEY: misc_feature
<222> LOCATION: (30)..(31)
<223> OTHER INFORMATION: wherein Xaa at positions 30-31 is any amino
      acid
<220> FEATURE:
<221> NAME/KEY: misc_feature
<222> LOCATION: (33)..(40)
<223> OTHER INFORMATION: wherein Xaa at positions 33-40 is any amino
      acid
<220> FEATURE:
<221> NAME/KEY: misc_feature
<222> LOCATION: (44)..(45)
<223> OTHER INFORMATION: wherein Xaa at positions 44-45 is any amino
      acid
<220> FEATURE:
<221> NAME/KEY: misc_feature
<222> LOCATION: (47)..(48)
<223> OTHER INFORMATION: wherein Xaa at positions 47-48 is any amino
      acid
<220> FEATURE:
<221> NAME/KEY: misc_feature
<222> LOCATION: (50)..(52)
<223> OTHER INFORMATION: wherein Xaa at positions 50-52 is any amino
      acid
<220> FEATURE:
<221> NAME/KEY: misc_feature
<222> LOCATION: (54)..(57)
<223> OTHER INFORMATION: wherein Xaa at positions 54-57 is any amino
      acid
```

```
<220> FEATURE:
<221> NAME/KEY: misc_feature
<222> LOCATION: (59)..(60)
<223> OTHER INFORMATION: wherein Xaa at positions 59-60 is any amino
      acid
<220> FEATURE:
<221> NAME/KEY: misc_feature
<222> LOCATION: (63)..(63)
<223> OTHER INFORMATION: wherein Xaa at position 63 is any amino acid
<220> FEATURE:
<221> NAME/KEY: misc_feature
<222> LOCATION: (65)..(72)
<223> OTHER INFORMATION: wherein Xaa at positions 65-72 is any amino
      acid
<220> FEATURE:
<221> NAME/KEY: misc_feature
<222> LOCATION: (74)..(80)
<223> OTHER INFORMATION: wherein Xaa at positions 74-80 is any amino
      acid
<220> FEATURE:
<221> NAME/KEY: misc_feature
<222> LOCATION: (82)..(82)
<223> OTHER INFORMATION: wherein Xaa at position 82 is any amino acid
<220> FEATURE:
<221> NAME/KEY: misc_feature
<222> LOCATION: (84)..(85)
<223> OTHER INFORMATION: wherein Xaa at positions 84-85 is any amino
      acid
<220> FEATURE:
<221> NAME/KEY: misc_feature
<222> LOCATION: (87)..(88)
<223> OTHER INFORMATION: wherein Xaa at positions 87-88 is any amino
      acid
<220> FEATURE:
<221> NAME/KEY: misc_feature
<222> LOCATION: (90)..(90)
<223> OTHER INFORMATION: wherein Xaa at position 90 is any amino acid
<220> FEATURE:
<221> NAME/KEY: misc_feature
<222> LOCATION: (92)..(93)
<223> OTHER INFORMATION: wherein Xaa at positions 92-93 is any amino
      acid
<220> FEATURE:
<221> NAME/KEY: misc_feature
<222> LOCATION: (95)..(95)
<223> OTHER INFORMATION: wherein Xaa at position 95 is any amino acid
<220> FEATURE:
<221> NAME/KEY: misc_feature
<222> LOCATION: (97)..(97)
<223> OTHER INFORMATION: wherein Xaa at position 97 is any amino acid

<400> SEQUENCE: 3

Leu Xaa Val Xaa Phe Xaa Asp Xaa Gly Trp Xaa Xaa Trp Xaa Xaa Xaa
1               5                   10                  15

Pro Xaa Gly Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Gln Xaa Xaa
        35                  40                  45

Val Xaa Xaa Xaa Asn Xaa Xaa Xaa Xaa Pro Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Tyr Xaa Xaa Met Xaa Val Xaa Xaa Cys Xaa Cys
                85                  90                  95

Xaa

<210> SEQ ID NO 4
<211> LENGTH: 102
<212> TYPE: PRT
<213> ORGANISM: Artificial Sequence
<220> FEATURE:
```

-continued

```
<223> OTHER INFORMATION: Biosynthetic protein capable of inducing
      endochondral bone formation
<220> FEATURE:
<221> NAME/KEY: misc_feature
<222> LOCATION: (2)..(5)
<223> OTHER INFORMATION: wherein Xaa at positions 2-5 is any amino acid
<220> FEATURE:
<221> NAME/KEY: misc_feature
<222> LOCATION: (7)..(7)
<223> OTHER INFORMATION: wherein Xaa at position 7 is any amino acid
<220> FEATURE:
<221> NAME/KEY: misc_feature
<222> LOCATION: (9)..(9)
<223> OTHER INFORMATION: wherein Xaa at position 9 is any amino acid
<220> FEATURE:
<221> NAME/KEY: misc_feature
<222> LOCATION: (11)..(11)
<223> OTHER INFORMATION: wherein Xaa at position 11 is any amino acid
<220> FEATURE:
<221> NAME/KEY: misc_feature
<222> LOCATION: (13)..(13)
<223> OTHER INFORMATION: wherein Xaa at position 13 is any amino acid
<220> FEATURE:
<221> NAME/KEY: misc_feature
<222> LOCATION: (16)..(17)
<223> OTHER INFORMATION: wherein Xaa at positions 16-17 is any amino
      acid
<220> FEATURE:
<221> NAME/KEY: misc_feature
<222> LOCATION: (19)..(21)
<223> OTHER INFORMATION: wherein Xaa at positions 19-21 is any amino
      acid
<220> FEATURE:
<221> NAME/KEY: misc_feature
<222> LOCATION: (23)..(23)
<223> OTHER INFORMATION: wherein Xaa at position 23 is any amino acid
<220> FEATURE:
<221> NAME/KEY: misc_feature
<222> LOCATION: (25)..(26)
<223> OTHER INFORMATION: wherein Xaa at positions 25-26 is any amino
      acid
<220> FEATURE:
<221> NAME/KEY: misc_feature
<222> LOCATION: (28)..(28)
<223> OTHER INFORMATION: wherein Xaa at position 28 is any amino acid
<220> FEATURE:
<221> NAME/KEY: misc_feature
<222> LOCATION: (31)..(31)
<223> OTHER INFORMATION: wherein Xaa at position 31 is any amino acid
<220> FEATURE:
<221> NAME/KEY: misc_feature
<222> LOCATION: (33)..(33)
<223> OTHER INFORMATION: wherein Xaa at position 33 is any amino acid
<220> FEATURE:
<221> NAME/KEY: misc_feature
<222> LOCATION: (35)..(36)
<223> OTHER INFORMATION: wherein Xaa at positions 35-36 is any amino
      acid
<220> FEATURE:
<221> NAME/KEY: misc_feature
<222> LOCATION: (38)..(45)
<223> OTHER INFORMATION: wherein Xaa at positions 38-45 is any amino
      acid
<220> FEATURE:
<221> NAME/KEY: misc_feature
<222> LOCATION: (49)..(50)
<223> OTHER INFORMATION: wherein Xaa at positions 49-50 is any amino
      acid
<220> FEATURE:
<221> NAME/KEY: misc_feature
<222> LOCATION: (52)..(53)
<223> OTHER INFORMATION: wherein Xaa at positions 52-53 is any amino
      acid
<220> FEATURE:
<221> NAME/KEY: misc_feature
<222> LOCATION: (55)..(57)
<223> OTHER INFORMATION: wherein Xaa at positions 55-57 is any amino
      acid
<220> FEATURE:
```

```
<221> NAME/KEY: misc_feature
<222> LOCATION: (59)..(62)
<223> OTHER INFORMATION: wherein Xaa at positions 59-62 is any amino
      acid
<220> FEATURE:
<221> NAME/KEY: misc_feature
<222> LOCATION: (64)..(65)
<223> OTHER INFORMATION: wherein Xaa at positions 64-65 is any amino
      acid
<220> FEATURE:
<221> NAME/KEY: misc_feature
<222> LOCATION: (68)..(68)
<223> OTHER INFORMATION: wherein Xaa at position 68 is any amino acid
<220> FEATURE:
<221> NAME/KEY: misc_feature
<222> LOCATION: (70)..(77)
<223> OTHER INFORMATION: wherein Xaa at positions 70-77 is any amino
      acid
<220> FEATURE:
<221> NAME/KEY: misc_feature
<222> LOCATION: (79)..(85)
<223> OTHER INFORMATION: wherein Xaa at positions 79-85 is any amino
      acid
<220> FEATURE:
<221> NAME/KEY: misc_feature
<222> LOCATION: (87)..(87)
<223> OTHER INFORMATION: wherein Xaa at position 87 is any amino acid
<220> FEATURE:
<221> NAME/KEY: misc_feature
<222> LOCATION: (89)..(90)
<223> OTHER INFORMATION: wherein Xaa at positions 89-90 is any amino
      acid
<220> FEATURE:
<221> NAME/KEY: misc_feature
<222> LOCATION: (92)..(93)
<223> OTHER INFORMATION: wherein Xaa at positions 92-93 is any amino
      acid
<220> FEATURE:
<221> NAME/KEY: misc_feature
<222> LOCATION: (95)..(95)
<223> OTHER INFORMATION: wherein Xaa at position 95 is any amino acid
<220> FEATURE:
<221> NAME/KEY: misc_feature
<222> LOCATION: (97)..(98)
<223> OTHER INFORMATION: wherein Xaa at positions 97-98 is any amino
      acid
<220> FEATURE:
<221> NAME/KEY: misc_feature
<222> LOCATION: (100)..(100)
<223> OTHER INFORMATION: wherein Xaa at position 100 is any amino acid
<220> FEATURE:
<221> NAME/KEY: misc_feature
<222> LOCATION: (102)..(102)
<223> OTHER INFORMATION: wherein Xaa at position 102 is any amino acid

<400> SEQUENCE: 4

Cys Xaa Xaa Xaa Xaa Leu Xaa Val Xaa Phe Xaa Asp Xaa Gly Trp Xaa
1               5                   10                  15

Xaa Trp Xaa Xaa Xaa Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Gln Xaa Xaa Val Xaa Xaa Xaa Asn Xaa Xaa Xaa Xaa Pro Xaa
    50                  55                  60

Xaa Cys Cys Xaa Pro Xaa Xaa Xaa Xaa Xaa Xaa Xaa Xaa Leu Xaa Xaa
65                  70                  75                  80

Xaa Xaa Xaa Xaa Xaa Val Xaa Leu Xaa Xaa Tyr Xaa Xaa Met Xaa Val
            85                  90                  95

Xaa Xaa Cys Xaa Cys Xaa
            100
```

```
<210> SEQ ID NO 5
<211> LENGTH: 97
<212> TYPE: PRT
<213> ORGANISM: Artificial Sequence
<220> FEATURE:
<223> OTHER INFORMATION: Biosynthetic protein capable of inducing
      endochondral bone formation
<220> FEATURE:
<221> NAME/KEY: misc_feature
<222> LOCATION: (2)..(2)
<223> OTHER INFORMATION: wherein Xaa at position 2 is a tyrosine, lysine
      or phenylalanine
<220> FEATURE:
<221> NAME/KEY: misc_feature
<222> LOCATION: (4)..(4)
<223> OTHER INFORMATION: wherein Xaa at position 4 is an aspartic acid,
      a serine or a glutamic acid
<220> FEATURE:
<221> NAME/KEY: misc_feature
<222> LOCATION: (6)..(6)
<223> OTHER INFORMATION: wherein Xaa at position 6 is an arginine, a
      serine, a lysine or an alanine<220> FEATURE:
<221> NAME/KEY: misc_feature
<222> LOCATION: (8)..(8)
<223> OTHER INFORMATION: wherein Xaa at position 8 is a valine, a
      leucine or an isoleucine
<220> FEATURE:
<221> NAME/KEY: misc_feature
<222> LOCATION: (11)..(11)
<223> OTHER INFORMATION: wherein Xaa at position 11 is an asparagine, a
      glutamine, an aspartic acid or a serine
<220> FEATURE:
<221> NAME/KEY: misc_feature
<222> LOCATION: (12)..(12)
<223> OTHER INFORMATION: wherein Xaa at position 12 is a aspartic acid,
      glutamic acid or an asparagine
<220> FEATURE:
<221> NAME/KEY: misc_feature
<222> LOCATION: (14)..(14)
<223> OTHER INFORMATION: wherein Xaa at position 14 is an isoleucine or
      a valine
<220> FEATURE:
<221> NAME/KEY: misc_feature
<222> LOCATION: (15)..(15)
<223> OTHER INFORMATION: wherein Xaa at position 15 is an isoleucine or
      a valine
<220> FEATURE:
<221> NAME/KEY: misc_feature
<222> LOCATION: (16)..(16)
<223> OTHER INFORMATION: wherein Xaa at position 16 is an alanine or a
      serine
<220> FEATURE:
<221> NAME/KEY: misc_feature
<222> LOCATION: (18)..(18)
<223> OTHER INFORMATION: wherein Xaa at position 18 is a proline, a
      glutamic acid, a leucine or a lysine
<220> FEATURE:
<221> NAME/KEY: misc_feature
<222> LOCATION: (20)..(20)
<223> OTHER INFORMATION: wherein Xaa at position 20 is a tyrosine or a
      phenylalanine
<220> FEATURE:
<221> NAME/KEY: misc_feature
<222> LOCATION: (21)..(21)
<223> OTHER INFORMATION: wherein Xaa at position 21 is a hiostidine or a
      glutamic acid
<220> FEATURE:
<221> NAME/KEY: misc_feature
<222> LOCATION: (23)..(23)
<223> OTHER INFORMATION: wherein Xaa at position 23 is a phenylalanine,
      a tyrosine or an asparagine
<220> FEATURE:
<221> NAME/KEY: misc_feature
<222> LOCATION: (26)..(26)
<223> OTHER INFORMATION: wherein Xaa at position 26 is a histidine, a
      glutamic acid or a serine
<220> FEATURE:
<221> NAME/KEY: misc_feature
<222> LOCATION: (28)..(28)
```

```
<223> OTHER INFORMATION: wherein Xaa at position 28 is a glutamic acid
      or an alanine
<220> FEATURE:
<221> NAME/KEY: misc_feature
<222> LOCATION: (30)..(30)
<223> OTHER INFORMATION: wherein Xaa at position 30 is a proline, an
      alanine or a glutamine
<220> FEATURE:
<221> NAME/KEY: misc_feature
<222> LOCATION: (31)..(31)
<223> OTHER INFORMATION: wherein Xaa at position 31 is a phenylalanine
      or a tyrosine
<220> FEATURE:
<221> NAME/KEY: misc_feature
<222> LOCATION: (33)..(33)
<223> OTHER INFORMATION: wherein Xaa at position 33 is a leucine, a
      methionine or an isoleucine
<220> FEATURE:
<221> NAME/KEY: misc_feature
<222> LOCATION: (34)..(34)
<223> OTHER INFORMATION: wherein Xaa at position 34 is an alanine, a
      proline or a threonine
<220> FEATURE:
<221> NAME/KEY: misc_feature
<222> LOCATION: (35)..(35)
<223> OTHER INFORMATION: wherein Xaa at position 35 is an aspartic acid,
      a glutamine or a lysine
<220> FEATURE:
<221> NAME/KEY: misc_feature
<222> LOCATION: (36)..(36)
<223> OTHER INFORMATION: wherein Xaa at position 36 is a histidine or a
      serine
<220> FEATURE:
<221> NAME/KEY: misc_feature
<222> LOCATION: (37)..(37)
<223> OTHER INFORMATION: wherein Xaa at position 37 is a leucine, a
      methionine or a phenyl alanine
<220> FEATURE:
<221> NAME/KEY: misc_feature
<222> LOCATION: (38)..(38)
<223> OTHER INFORMATION: wherein Xaa at position 38 is an asparagine or
      a lysine
<220> FEATURE:
<221> NAME/KEY: misc_feature
<222> LOCATION: (39)..(39)
<223> OTHER INFORMATION: wherein Xaa at position 39 is a serine, an
      alanine or a proline
<220> FEATURE:
<221> NAME/KEY: misc_feature
<222> LOCATION: (40)..(40)
<223> OTHER INFORMATION: wherein Xaa at position 40 is a threonine or a
      serine
<220> FEATURE:
<221> NAME/KEY: misc_feature
<222> LOCATION: (44)..(44)
<223> OTHER INFORMATION: wherein Xaa at position 44 is an isoleucine, a
      valine or a threonine
<220> FEATURE:
<221> NAME/KEY: misc_feature
<222> LOCATION: (45)..(45)
<223> OTHER INFORMATION: wherein Xaa at position 45 is a valine, an
      isoleucine or a leucine
<220> FEATURE:
<221> NAME/KEY: misc_feature
<222> LOCATION: (47)..(47)
<223> OTHER INFORMATION: wherein Xaa at position 47 is a threonine or a
      serine
<220> FEATURE:
<221> NAME/KEY: misc_feature
<222> LOCATION: (48)..(48)
<223> OTHER INFORMATION: wherein Xaa at position 48 is a leucine or an
      isoleucine
<220> FEATURE:
<221> NAME/KEY: misc_feature
<222> LOCATION: (50)..(50)
<223> OTHER INFORMATION: wherein Xaa at position 50 is an asparagine, a
      histidine or an arginine
<220> FEATURE:
<221> NAME/KEY: misc_feature
```

-continued

```
<222> LOCATION: (51)..(51)
<223> OTHER INFORMATION: wherein Xaa at position 51 is a serine, an
      alanine, a phenylalanine or an asparagine
<220> FEATURE:
<221> NAME/KEY: misc_feature
<222> LOCATION: (52)..(52)
<223> OTHER INFORMATION: wherein Xaa at position 52 is a valine or an
      isoleucine
<220> FEATURE:
<221> NAME/KEY: misc_feature
<222> LOCATION: (54)..(54)
<223> OTHER INFORMATION: wherein Xaa at position 54 is a proline or a
      serine
<220> FEATURE:
<221> NAME/KEY: misc_feature
<222> LOCATION: (55)..(55)
<223> OTHER INFORMATION: wherein Xaa at position 55 is a glycine or a
      glutamic acid
<220> FEATURE:
<221> NAME/KEY: misc_feature
<222> LOCATION: (56)..(56)
<223> OTHER INFORMATION: wherein Xaa at position 56 is a lysine, a
      glutamine, a threonine or a serine
<220> FEATURE:
<221> NAME/KEY: misc_feature
<222> LOCATION: (57)..(57)
<223> OTHER INFORMATION: wherein Xaa at position 57 is an isoleucine or
      a leucine
<220> FEATURE:
<221> NAME/KEY: misc_feature
<222> LOCATION: (59)..(59)
<223> OTHER INFORMATION: wherein Xaa at position 59 is a lysine or a
      glutamic acid
<220> FEATURE:
<221> NAME/KEY: misc_feature
<222> LOCATION: (60)..(60)
<223> OTHER INFORMATION: wherein Xaa at position 60 is an alanine, a
      proline or a serine
<220> FEATURE:
<221> NAME/KEY: misc_feature
<222> LOCATION: (63)..(63)
<223> OTHER INFORMATION: wherein Xaa at position 63 is a valine or an
      alanine
<220> FEATURE:
<221> NAME/KEY: misc_feature
<222> LOCATION: (65)..(65)
<223> OTHER INFORMATION: wherein Xaa at position 65 is a threonine or a
      glutamic acid
<220> FEATURE:
<221> NAME/KEY: misc_feature
<222> LOCATION: (66)..(66)
<223> OTHER INFORMATION: wherein Xaa at position 66 is a glutamic acid,
      a glutamine or a lysine
<220> FEATURE:
<221> NAME/KEY: misc_feature
<222> LOCATION: (67)..(67)
<223> OTHER INFORMATION: wherein Xaa at position 67 is a leucine or a
      methionine
<220> FEATURE:
<221> NAME/KEY: misc_feature
<222> LOCATION: (68)..(68)
<223> OTHER INFORMATION: wherein Xaa at position 68 is a serine, an
      asparagine or an aspartic acid
<220> FEATURE:
<221> NAME/KEY: misc_feature
<222> LOCATION: (69)..(69)
<223> OTHER INFORMATION: wherein Xaa at position 69 is an alanine, a
      serine or a proline
<220> FEATURE:
<221> NAME/KEY: misc_feature
<222> LOCATION: (70)..(70)
<223> OTHER INFORMATION: wherein Xaa at position 70 is an isoleucine, a
      leucine or a valine
<220> FEATURE:
<221> NAME/KEY: misc_feature
<222> LOCATION: (71)..(71)
<223> OTHER INFORMATION: wherein Xaa at position 71 is a serine or an
      alanine
<220> FEATURE:
```

-continued

```
<221> NAME/KEY: misc_feature
<222> LOCATION: (72)..(72)
<223> OTHER INFORMATION: wherein Xaa at position 72 is a methionine, a
      valine or an isoleucine
<220> FEATURE:
<221> NAME/KEY: misc_feature
<222> LOCATION: (74)..(74)
<223> OTHER INFORMATION: wherein Xaa at position 74 is a phenylalanine
      or a tyrosine
<220> FEATURE:
<221> NAME/KEY: misc_feature
<222> LOCATION: (75)..(75)
<223> OTHER INFORMATION: wherein Xaa at position 75 is a leucine, a
      tyrosine or a phenylalanine
<220> FEATURE:
<221> NAME/KEY: misc_feature
<222> LOCATION: (76)..(76)
<223> OTHER INFORMATION: wherein Xaa at position 76 is an aspartic acid
      or an asparagine
<220> FEATURE:
<221> NAME/KEY: misc_feature
<222> LOCATION: (77)..(77)
<223> OTHER INFORMATION: wherein Xaa at position 77 is a glutamic acid,
      an asparagine or an aspartic acid
<220> FEATURE:
<221> NAME/KEY: misc_feature
<222> LOCATION: (78)..(78)
<223> OTHER INFORMATION: wherein Xaa at position 78 is a glutamine or an
      asparagine
<220> FEATURE:
<221> NAME/KEY: misc_feature
<222> LOCATION: (79)..(79)
<223> OTHER INFORMATION: wherein Xaa at position 79 is a glutamic acid,
      a glutamine, a serine or a lysine
<220> FEATURE:
<221> NAME/KEY: misc_feature
<222> LOCATION: (80)..(80)
<223> OTHER INFORMATION: wherein Xaa at position 80 is an asparagine or
      a lysine
<220> FEATURE:
<221> NAME/KEY: misc_feature
<222> LOCATION: (82)..(82)
<223> OTHER INFORMATION: wherein Xaa at position 82 is a valine or an
      isoleucine
<220> FEATURE:
<221> NAME/KEY: misc_feature
<222> LOCATION: (84)..(84)
<223> OTHER INFORMATION: wherein Xaa at position 84 is a lysine or an
      arginine
<220> FEATURE:
<221> NAME/KEY: misc_feature
<222> LOCATION: (85)..(85)
<223> OTHER INFORMATION: wherein Xaa at position 85 is an asparagine, a
      lysine or a histidine
<220> FEATURE:
<221> NAME/KEY: misc_feature
<222> LOCATION: (87)..(87)
<223> OTHER INFORMATION: wherein Xaa at position 87 is a glutamine, a
      glutamic acid, an arginine or a proline
<220> FEATURE:
<221> NAME/KEY: misc_feature
<222> LOCATION: (88)..(88)
<223> OTHER INFORMATION: wherein Xaa at position 88 is an aspartic acid,
      a glutamic acid or an asparagine
<220> FEATURE:
<221> NAME/KEY: misc_feature
<222> LOCATION: (90)..(90)
<223> OTHER INFORMATION: wherein Xaa at position 90 is a valine or a
      threonine
<220> FEATURE:
<221> NAME/KEY: misc_feature
<222> LOCATION: (92)..(92)
<223> OTHER INFORMATION: wherein Xaa at position 92 is a glutamic acid,
      an aspartic acid or an arginine
<220> FEATURE:
<221> NAME/KEY: misc_feature
<222> LOCATION: (93)..(93)
<223> OTHER INFORMATION: wherein Xaa at position 93 is a glycine, an
      alanine, a serine or a glutamic acid
```

```
<220> FEATURE:
<221> NAME/KEY: misc_feature
<222> LOCATION: (95)..(95)
<223> OTHER INFORMATION: wherein Xaa at position 95 is a glycine or a
      histidine
<220> FEATURE:
<221> NAME/KEY: misc_feature
<222> LOCATION: (97)..(97)
<223> OTHER INFORMATION: wherein Xaa at position 97 is a an arginine or
      a histidine

<400> SEQUENCE: 5

Leu Xaa Val Xaa Phe Xaa Asp Xaa Gly Trp Xaa Xaa Trp Xaa Xaa Xaa
1               5                   10                  15

Pro Xaa Gly Xaa Xaa Ala Xaa Tyr Cys Xaa Gly Xaa Cys Xaa Xaa Pro
            20                  25                  30

Xaa Xaa Xaa Xaa Xaa Xaa Asn His Ala Xaa Xaa Gln Xaa Xaa
        35                  40                  45

Val Xaa Xaa Xaa Asn Xaa Xaa Xaa Xaa Pro Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Tyr Xaa Xaa Met Xaa Val Xaa Xaa Cys Xaa Cys
                85                  90                  95

Xaa

<210> SEQ ID NO 6
<211> LENGTH: 102
<212> TYPE: PRT
<213> ORGANISM: Artificial Sequence
<220> FEATURE:
<223> OTHER INFORMATION: Biosynthetic protein capable of inducing
      endochondral bone formation
<220> FEATURE:
<221> NAME/KEY: misc_feature
<222> LOCATION: (2)..(2)
<223> OTHER INFORMATION: wherein Xaa at position 2 is a lysine or an
      arginine
<220> FEATURE:
<221> NAME/KEY: misc_feature
<222> LOCATION: (4)..(4)
<223> OTHER INFORMATION: wherein Xaa at position 4 is a histidine, an
      arginine or a lysine
<220> FEATURE:
<221> NAME/KEY: misc_feature
<222> LOCATION: (5)..(5)
<223> OTHER INFORMATION: wherein Xaa at position 5 is a proline, a
      serine, a glutamic acid
      or a glutamine
<220> FEATURE:
<221> NAME/KEY: misc_feature
<222> LOCATION: (7)..(7)
<223> OTHER INFORMATION: wherein Xaa at position 7 is a tyrosine, a
      lysine or a phenylalanine
<220> FEATURE:
<221> NAME/KEY: misc_feature
<222> LOCATION: (9)..(9)
<223> OTHER INFORMATION: wherein Xaa at position 9 is an aspartic acid,
      a serine or a glutamic acid
<220> FEATURE:
<221> NAME/KEY: misc_feature
<222> LOCATION: (11)..(11)
<223> OTHER INFORMATION: wherein Xaa at position 11 is an arginine a
      serine, a lysine or an alanine
<220> FEATURE:
<221> NAME/KEY: misc_feature
<222> LOCATION: (13)..(13)
<223> OTHER INFORMATION: wherein Xaa at position 13 is a valine, a
      leucine or an isoleucine
<220> FEATURE:
<221> NAME/KEY: misc_feature
```

-continued

```
<222> LOCATION: (16)..(16)
<223> OTHER INFORMATION: wherein Xaa at position 16 is an asparagine, a
      glutamine, an aspartic acid or a serine
<220> FEATURE:
<221> NAME/KEY: misc_feature
<222> LOCATION: (17)..(17)
<223> OTHER INFORMATION: wherein Xaa at position 17 is an aspartic acid,
      a glutamic acid or an asparagine
<220> FEATURE:
<221> NAME/KEY: misc_feature
<222> LOCATION: (19)..(19)
<223> OTHER INFORMATION: wherein Xaa at position 19 is an isoleucine or
      a valine
<220> FEATURE:
<221> NAME/KEY: misc_feature
<222> LOCATION: (20)..(20)
<223> OTHER INFORMATION: wherein Xaa at position 20 is a valine or an
      isoleucine
<220> FEATURE:
<221> NAME/KEY: misc_feature
<222> LOCATION: (21)..(21)
<223> OTHER INFORMATION: wherein Xaa at position 21 is an alanine or a
      serine
<220> FEATURE:
<221> NAME/KEY: misc_feature
<222> LOCATION: (23)..(23)
<223> OTHER INFORMATION: wherein Xaa at position 23 is a proline, a
      glutamic acid, a leucine or a lysine
<220> FEATURE:
<221> NAME/KEY: misc_feature
<222> LOCATION: (25)..(25)
<223> OTHER INFORMATION: wherein Xaa at position 25 is a tyrosine or a
      phenylalanine
<220> FEATURE:
<221> NAME/KEY: misc_feature
<222> LOCATION: (26)..(26)
<223> OTHER INFORMATION: wherein Xaa at positon 26 is a histidine or an
      aspartic acid
<220> FEATURE:
<221> NAME/KEY: misc_feature
<222> LOCATION: (28)..(28)
<223> OTHER INFORMATION: wherein Xaa at position 28 is a phenylalanine,
      a tyrosine or an asparagine
<220> FEATURE:
<221> NAME/KEY: misc_feature
<222> LOCATION: (31)..(31)
<223> OTHER INFORMATION: wherein Xaa at position 31 is a histidine, a
      glutamic acid or a serine
<220> FEATURE:
<221> NAME/KEY: misc_feature
<222> LOCATION: (33)..(33)
<223> OTHER INFORMATION: wherein Xaa at position 33 is a glutamic acid
      or an alanine
<220> FEATURE:
<221> NAME/KEY: misc_feature
<222> LOCATION: (35)..(35)
<223> OTHER INFORMATION: wherein Xaa at position 35 is a proline, a
      glutamine or an alanine
<220> FEATURE:
<221> NAME/KEY: misc_feature
<222> LOCATION: (36)..(36)
<223> OTHER INFORMATION: wherein Xaa at position 36 is a phenylalanine
      or a tyrosine
<220> FEATURE:
<221> NAME/KEY: misc_feature
<222> LOCATION: (38)..(38)
<223> OTHER INFORMATION: wherein Xaa at position 38 is a leucine, a
      methionine or an isoleucine
<220> FEATURE:
<221> NAME/KEY: misc_feature
<222> LOCATION: (39)..(39)
<223> OTHER INFORMATION: wherein Xaa at position 39 is an alanine, a
      proline or a threonine
<220> FEATURE:
<221> NAME/KEY: misc_feature
<222> LOCATION: (40)..(40)
<223> OTHER INFORMATION: wherein Xaa at position 40 is an aspartic acid,
      a glutamic acid or a lysine
<220> FEATURE:
```

```
<221> NAME/KEY: misc_feature
<222> LOCATION: (41)..(41)
<223> OTHER INFORMATION: wherein Xaa at position 41 is a histidine or a
      serine
<220> FEATURE:
<221> NAME/KEY: misc_feature
<222> LOCATION: (42)..(42)
<223> OTHER INFORMATION: wherein Xaa at position 42 is a leucine, a
      methionine or a phenylalanine
<220> FEATURE:
<221> NAME/KEY: misc_feature
<222> LOCATION: (43)..(43)
<223> OTHER INFORMATION: wherein Xaa at position 43 is an asparagine or
      a lysine
<220> FEATURE:
<221> NAME/KEY: misc_feature
<222> LOCATION: (44)..(44)
<223> OTHER INFORMATION: wherein Xaa at position 44 is a serine, an
      alanine or a proline
<220> FEATURE:
<221> NAME/KEY: misc_feature
<222> LOCATION: (45)..(45)
<223> OTHER INFORMATION: wherein Xaa at position 45 is a threonine or a
      serine
<220> FEATURE:
<221> NAME/KEY: misc_feature
<222> LOCATION: (49)..(49)
<223> OTHER INFORMATION: wherein Xaa at position 49 is an isoleucine, a
      valine or a threonine
<220> FEATURE:
<221> NAME/KEY: misc_feature
<222> LOCATION: (50)..(50)
<223> OTHER INFORMATION: wherein Xaa at position 50 is a valine, an
      isoleucine or a leucine
<220> FEATURE:
<221> NAME/KEY: misc_feature
<222> LOCATION: (52)..(52)
<223> OTHER INFORMATION: wherein Xaa at position 52 is a threonine or a
      serine
<220> FEATURE:
<221> NAME/KEY: misc_feature
<222> LOCATION: (53)..(53)
<223> OTHER INFORMATION: wherein Xaa at position 53 is a leucine or a
      isoleucine
<220> FEATURE:
<221> NAME/KEY: misc_feature
<222> LOCATION: (55)..(55)
<223> OTHER INFORMATION: wherein Xaa at position 55 is an asparagine, a
      histidine or an arginine
<220> FEATURE:
<221> NAME/KEY: misc_feature
<222> LOCATION: (56)..(56)
<223> OTHER INFORMATION: wherein Xaa at position 56 is a serine, an
      alanine, a phenylalanin or an asparagine
<220> FEATURE:
<221> NAME/KEY: misc_feature
<222> LOCATION: (57)..(57)
<223> OTHER INFORMATION: wherein Xaa at position 57 is a valine or an
      isoleucine
<220> FEATURE:
<221> NAME/KEY: misc_feature
<222> LOCATION: (59)..(59)
<223> OTHER INFORMATION: wherein Xaa at position 59 is a serine or a
      proline
<220> FEATURE:
<221> NAME/KEY: misc_feature
<222> LOCATION: (60)..(60)
<223> OTHER INFORMATION: wherein Xaa at position 60 is a glycine or a
      glutamic acid
<220> FEATURE:
<221> NAME/KEY: misc_feature
<222> LOCATION: (61)..(61)
<223> OTHER INFORMATION: wherein Xaa at position 61 is a lysine, a
      glutamine, a threonine or a serine
<220> FEATURE:
<221> NAME/KEY: misc_feature
<222> LOCATION: (62)..(62)
<223> OTHER INFORMATION: wherein Xaa at position 62 is an isoleucine or
      a valine
```

-continued

```
<220> FEATURE:
<221> NAME/KEY: misc_feature
<222> LOCATION: (64)..(64)
<223> OTHER INFORMATION: wherein Xaa at position 64 is a lysine or a
      glutamic acid
<220> FEATURE:
<221> NAME/KEY: misc_feature
<222> LOCATION: (65)..(65)
<223> OTHER INFORMATION: wherein Xaa at position 65 is an alanine, a
      proline or a serine
<220> FEATURE:
<221> NAME/KEY: misc_feature
<222> LOCATION: (68)..(68)
<223> OTHER INFORMATION: wherein Xaa at position 68 is a valine or an
      alanine
<220> FEATURE:
<221> NAME/KEY: misc_feature
<222> LOCATION: (70)..(70)
<223> OTHER INFORMATION: wherein Xaa at position 70 is a threonine or a
      glutamic acid
<220> FEATURE:
<221> NAME/KEY: misc_feature
<222> LOCATION: (71)..(71)
<223> OTHER INFORMATION: wherein Xaa at position 71 is a glutamic acid,
      a glutamine or a lysine
<220> FEATURE:
<221> NAME/KEY: misc_feature
<222> LOCATION: (72)..(72)
<223> OTHER INFORMATION: wherein Xaa at position 72 is a leucine or a
      methionine
<220> FEATURE:
<221> NAME/KEY: misc_feature
<222> LOCATION: (73)..(73)
<223> OTHER INFORMATION: wherein Xaa at position 73 is a serine, an
      asparagine or an aspartic acid
<220> FEATURE:
<221> NAME/KEY: misc_feature
<222> LOCATION: (74)..(74)
<223> OTHER INFORMATION: wherein Xaa at position 74 is an alanine, a
      serine or a proline
<220> FEATURE:
<221> NAME/KEY: misc_feature
<222> LOCATION: (75)..(75)
<223> OTHER INFORMATION: wherein Xaa at position 75 is an isoleucine,
      a leucine or a valine
<220> FEATURE:
<221> NAME/KEY: misc_feature
<222> LOCATION: (76)..(76)
<223> OTHER INFORMATION: wherein Xaa at position 76 is a serine or an
      alanine
<220> FEATURE:
<221> NAME/KEY: misc_feature
<222> LOCATION: (77)..(77)
<223> OTHER INFORMATION: wherein Xaa at position 77 is a methionine, a
      valine or an isoleucine
<220> FEATURE:
<221> NAME/KEY: misc_feature
<222> LOCATION: (79)..(79)
<223> OTHER INFORMATION: wherein Xaa at position 79 is a phenylalanine
      or a tyrosine
<220> FEATURE:
<221> NAME/KEY: misc_feature
<222> LOCATION: (80)..(80)
<223> OTHER INFORMATION: wherein Xaa at position 80 is a leucine, a
      tyrosine or a phenylalanine
<220> FEATURE:
<221> NAME/KEY: misc_feature
<222> LOCATION: (81)..(81)
<223> OTHER INFORMATION: wherein Xaa at position 81 is an aspartic acid
      or an asparagine
<220> FEATURE:
<221> NAME/KEY: misc_feature
<222> LOCATION: (82)..(82)
<223> OTHER INFORMATION: wherein Xaa at position 82 is a glutamic acid,
      an asparagine or an aspartic acid
<220> FEATURE:
<221> NAME/KEY: misc_feature
<222> LOCATION: (83)..(83)
<223> OTHER INFORMATION: wherein Xaa at position 83 is a glutamine or an
``` asparagine
<220> FEATURE:
<221> NAME/KEY: misc_feature
<222> LOCATION: (84)..(84)
<223> OTHER INFORMATION: wherein Xaa at position 84 is a glutamic acid,
      a glutamine, a serine or a lysine
<220> FEATURE:
<221> NAME/KEY: misc_feature
<222> LOCATION: (85)..(85)
<223> OTHER INFORMATION: wherein Xaa at position 85 is an asparagine or
      a lysine
<220> FEATURE:
<221> NAME/KEY: misc_feature
<222> LOCATION: (87)..(87)
<223> OTHER INFORMATION: wherein Xaa at position 87 is a valine or an
      isoleucine
<220> FEATURE:
<221> NAME/KEY: misc_feature
<222> LOCATION: (89)..(89)
<223> OTHER INFORMATION: wherein Xaa at position 89 is a lysine or an
      arginine
<220> FEATURE:
<221> NAME/KEY: misc_feature
<222> LOCATION: (90)..(90)
<223> OTHER INFORMATION: wherein Xaa at position 90 is an asparagine, a
      lysine or a histidine
<220> FEATURE:
<221> NAME/KEY: misc_feature
<222> LOCATION: (92)..(92)
<223> OTHER INFORMATION: wherein Xaa at position 92 is a glutamine, a
      glutamic acid, an arginine or a proline
<220> FEATURE:
<221> NAME/KEY: misc_feature
<222> LOCATION: (93)..(93)
<223> OTHER INFORMATION: wherein Xaa at position 93 is an aspartic acid,
      a glutamic acid or an asparagine
<220> FEATURE:
<221> NAME/KEY: misc_feature
<222> LOCATION: (95)..(95)
<223> OTHER INFORMATION: wherein Xaa at position 95 is a valine or a
      threonine
<220> FEATURE:
<221> NAME/KEY: misc_feature
<222> LOCATION: (97)..(97)
<223> OTHER INFORMATION: wherein Xaa at position 97 is a glutamic acid,
      an aspartic acid or an arginine
<220> FEATURE:
<221> NAME/KEY: misc_feature
<222> LOCATION: (98)..(98)
<223> OTHER INFORMATION: wherein Xaa at position 98 is a glycine, an
      alanine, a serine or a glutamic acid
<220> FEATURE:
<221> NAME/KEY: misc_feature
<222> LOCATION: (100)..(100)
<223> OTHER INFORMATION: wherein Xaa at position 100 is a glycine or a
      histidine
<220> FEATURE:
<221> NAME/KEY: misc_feature
<222> LOCATION: (102)..(102)
<223> OTHER INFORMATION: wherein Xaa at position 102 is a an arginine or
      a histidine

<400> SEQUENCE: 6

Cys Xaa Arg Xaa Xaa Leu Xaa Val Xaa Phe Xaa Asp Xaa Gly Trp Xaa
1               5                   10                  15

Xaa Trp Xaa Xaa Xaa Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Gln Xaa Xaa Val Xaa Xaa Xaa Asn Xaa Xaa Xaa Xaa Pro Xaa
    50                  55                  60

Xaa Cys Cys Xaa Pro Xaa Xaa Xaa Xaa Xaa Xaa Xaa Xaa Leu Xaa Xaa
65                  70                  75                  80

```
Xaa Xaa Xaa Xaa Xaa Val Xaa Leu Xaa Xaa Tyr Xaa Xaa Met Xaa Val
                85                  90                  95

Xaa Xaa Cys Xaa Cys Xaa
            100

<210> SEQ ID NO 7
<211> LENGTH: 102
<212> TYPE: PRT
<213> ORGANISM: Xenopus sp.
<220> FEATURE:
<223> OTHER INFORMATION: Vg1 protein sequence with osteogenic activity

<400> SEQUENCE: 7

Cys Lys Lys Arg His Leu Tyr Val Glu Phe Lys Asp Val Gly Trp Gln
1               5                   10                  15

Asn Trp Val Ile Ala Pro Gln Gly Tyr Met Ala Asn Tyr Cys Tyr Gly
            20                  25                  30

Glu Cys Pro Tyr Pro Leu Thr Glu Ile Leu Asn Gly Ser Asn His Ala
        35                  40                  45

Ile Leu Gln Thr Leu Val His Ser Ile Glu Pro Glu Asp Ile Pro Leu
50                  55                  60

Pro Cys Cys Val Pro Thr Lys Met Ser Pro Ile Ser Met Leu Phe Tyr
65                  70                  75                  80

Asp Asn Asn Asp Asn Val Val Leu Arg His Tyr Glu Asn Met Ala Val
                85                  90                  95

Asp Glu Cys Gly Cys Arg
            100

<210> SEQ ID NO 8
<211> LENGTH: 102
<212> TYPE: PRT
<213> ORGANISM: Drosophila sp.
<220> FEATURE:
<223> OTHER INFORMATION: DPP protein sequence with osteogenic activity

<400> SEQUENCE: 8

Cys Arg Arg His Ser Leu Tyr Val Asp Phe Ser Asp Val Gly Trp Asp
1               5                   10                  15

Asp Trp Ile Val Ala Pro Leu Gly Tyr Asp Ala Tyr Tyr Cys His Gly
            20                  25                  30

Lys Cys Pro Phe Pro Leu Ala Asp His Phe Asn Ser Thr Asn His Ala
        35                  40                  45

Val Val Gln Thr Leu Val Asn Asn Asn Pro Gly Lys Val Pro Lys
50                  55                  60

Ala Cys Cys Val Pro Thr Gln Leu Asp Ser Val Ala Met Leu Tyr Leu
65                  70                  75                  80

Asn Asp Gln Ser Thr Val Val Leu Lys Asn Tyr Gln Glu Met Thr Val
                85                  90                  95

Val Gly Cys Gly Cys Arg
            100

<210> SEQ ID NO 9
<211> LENGTH: 107
<212> TYPE: PRT
<213> ORGANISM: mammalian
<220> FEATURE:
<223> OTHER INFORMATION: OP1 protein sequence with osteogenic activity

<400> SEQUENCE: 9

His Gln Arg Gln Ala Cys Lys Lys His Glu Leu Tyr Val Ser Phe Arg
```

```
1               5                   10                  15
Asp Leu Gly Trp Gln Asp Trp Ile Ile Ala Pro Glu Gly Tyr Ala Ala
                20                  25                  30

Tyr Tyr Cys Glu Gly Glu Cys Ala Phe Pro Leu Asn Ser Tyr Met Asn
            35                  40                  45

Ala Thr Asn His Ala Ile Val Gln Thr Leu Val His Phe Ile Asn Pro
        50                  55                  60

Glu Thr Val Pro Lys Pro Cys Cys Ala Pro Thr Gln Leu Asn Ala Ile
65                  70                  75                  80

Ser Val Leu Tyr Phe Asp Asp Ser Ser Asn Val Ile Leu Lys Lys Tyr
                85                  90                  95

Arg Asn Met Val Val Arg Ala Cys Gly Cys His
                100                 105

<210> SEQ ID NO 10
<211> LENGTH: 103
<212> TYPE: PRT
<213> ORGANISM: mammalian
<220> FEATURE:
<223> OTHER INFORMATION: CBP-2a protein sequence with osteogenic activity

<400> SEQUENCE: 10

Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
                20                  25                  30

Glu Cys Pro Phe Pro Leu Ala Asp His Leu Asn Ser Thr Asn His Ala
            35                  40                  45

Ile Val Gln Thr Leu Val Asn Ser Val Asn Ser Lys Ile Pro Lys Ala
        50                  55                  60

Cys Cys Val Pro Thr Glu Leu Ser Ala Ile Ser Met Leu Tyr Leu Tyr
65                  70                  75                  80

Leu Asp Glu Asn Glu Lys Val Val Leu Lys Asn Tyr Gln Asp Met Val
                85                  90                  95

Val Glu Gly Cys Gly Cys Arg
            100

<210> SEQ ID NO 11
<211> LENGTH: 100
<212> TYPE: PRT
<213> ORGANISM: mammalian
<220> FEATURE:
<223> OTHER INFORMATION: CBMP-2b protein sequence with osteogenic
      activity

<400> SEQUENCE: 11

Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
                20                  25                  30

Asp Cys Pro Phe Pro Leu Ala Asp His Leu Asn Ser Thr Asn His Ala
            35                  40                  45

Ile Val Gln Thr Leu Val Asn Ser Val Asn Ser Ile Pro Lys Ala Cys
        50                  55                  60

Cys Val Pro Thr Glu Leu Ser Ala Ile Ser Met Leu Tyr Leu Asp Glu
65                  70                  75                  80

Tyr Asp Lys Val Val Leu Lys Asn Tyr Gln Glu Met Val Val Glu Gly
                85                  90                  95
```

```
Cys Gly Cys Arg
            100

<210> SEQ ID NO 12
<211> LENGTH: 103
<212> TYPE: PRT
<213> ORGANISM: mammalian
<220> FEATURE:
<223> OTHER INFORMATION: CBMP-3 protein sequence with osteogenic
      activity

<400> SEQUENCE: 12

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
        35                  40                  45

Thr Ile Gln Ser Ile Val Arg Ala Val Gly Val Val Pro Gly Ile Pro
    50                  55                  60

Glu Pro Cys Cys Val Pro Glu Lys Met Ser Ser Leu Ser Ile Leu Phe
65                  70                  75                  80

Phe Asp Glu Asn Lys Asn Val Val Leu Lys Val Tyr Pro Asn Met Thr
                85                  90                  95

Val Glu Ser Cys Ala Cys Arg
            100

<210> SEQ ID NO 13
<211> LENGTH: 98
<212> TYPE: PRT
<213> ORGANISM: Artificial Sequence
<220> FEATURE:
<223> OTHER INFORMATION: Biosynthetic COP1 protein with osteogenic
      activity

<400> SEQUENCE: 13

Leu Tyr Val Asp Phe Gln Arg Asp Val Gly Trp Asp Asp Trp Ile Ile
1               5                   10                  15

Ala Pro Val Asp Phe Asp Ala Tyr Tyr Cys Ser Gly Ala Cys Gln Phe
            20                  25                  30

Pro Ser Ala Asp His Phe Asn Ser Thr Asn His Ala Val Val Gln Thr
        35                  40                  45

Leu Val Asn Asn Met Asn Pro Gly Lys Val Pro Lys Pro Cys Cys Val
    50                  55                  60

Pro Thr Glu Leu Ser Ala Ile Ser Met Leu Tyr Leu Asp Glu Asn Ser
65                  70                  75                  80

Thr Val Val Leu Lys Asn Tyr Gln Glu Met Thr Val Val Gly Cys Gly
                85                  90                  95

Cys Arg

<210> SEQ ID NO 14
<211> LENGTH: 98
<212> TYPE: PRT
<213> ORGANISM: Artificial Sequence
<220> FEATURE:
<223> OTHER INFORMATION: Biosynthetic COP3 protein with osteogenic
      activity

<400> SEQUENCE: 14

Leu Tyr Val Asp Phe Gln Arg Asp Val Gly Trp Asp Asp Trp Ile Val
```

```
              1               5                  10                 15
Ala Pro Pro Gly Tyr Gln Ala Phe Tyr Cys Ser Gly Ala Cys Gln Phe
                    20                  25                  30

Pro Ser Ala Asp His Phe Asn Ser Thr Asn His Ala Val Val Gln Thr
                    35                  40                  45

Leu Val Asn Asn Met Asn Pro Gly Lys Val Pro Lys Pro Cys Cys Val
     50                  55                  60

Pro Thr Glu Leu Ser Ala Ile Ser Met Leu Tyr Leu Asp Glu Asn Glu
65                   70                  75                  80

Lys Val Val Leu Lys Asn Tyr Gln Glu Met Val Val Glu Gly Cys Gly
                    85                  90                  95

Cys Arg

<210> SEQ ID NO 15
<211> LENGTH: 97
<212> TYPE: PRT
<213> ORGANISM: Artificial Sequence
<220> FEATURE:
<223> OTHER INFORMATION: Biosynthetic COP4 protein with osteogenic
      activity

<400> SEQUENCE: 15

Leu Tyr Val Asp Phe Ser Asp Val Gly Trp Asp Asp Trp Ile Val Ala
1               5                  10                  15

Pro Pro Gly Tyr Gln Ala Phe Tyr Cys Ser Gly Ala Cys Gln Phe Pro
                    20                  25                  30

Ser Ala Asp His Phe Asn Ser Thr Asn His Ala Val Val Gln Thr Leu
                    35                  40                  45

Val Asn Asn Met Asn Pro Gly Lys Val Pro Lys Pro Cys Cys Val Pro
     50                  55                  60

Thr Glu Leu Ser Ala Ile Ser Met Leu Tyr Leu Asp Glu Asn Glu Lys
65                   70                  75                  80

Val Val Leu Lys Asn Tyr Gln Glu Met Val Val Glu Gly Cys Gly Cys
                    85                  90                  95

Arg

<210> SEQ ID NO 16
<211> LENGTH: 97
<212> TYPE: PRT
<213> ORGANISM: Artificial Sequence
<220> FEATURE:
<223> OTHER INFORMATION: Biosynhetic COP16 protein with osteogenic
      activity

<400> SEQUENCE: 16

Leu Tyr Val Asp Phe Ser Asp Val Gly Trp Asp Asp Trp Ile Val Ala
1               5                  10                  15

Pro Pro Gly Tyr Gln Ala Phe Tyr Cys Ser Gly Ala Cys Gln Phe Pro
                    20                  25                  30

Ser Ala Asp His Phe Asn Ser Thr Asn His Ala Val Val Gln Thr Leu
                    35                  40                  45

Val Asn Asn Met Asn Pro Gly Lys Val Pro Lys Pro Cys Cys Val Pro
     50                  55                  60

Thr Glu Leu Ser Ala Ile Ser Met Leu Tyr Leu Asp Glu Asn Glu Lys
65                   70                  75                  80

Val Val Leu Lys Asn Tyr Gln Glu Met Val Val Glu Gly Cys Gly Cys
                    85                  90                  95
```

Arg

```
<210> SEQ ID NO 17
<211> LENGTH: 17
<212> TYPE: PRT
<213> ORGANISM: Artificial Sequence
<220> FEATURE:
<223> OTHER INFORMATION: peptide fragment

<400> SEQUENCE: 17
```

Ser Phe Asp Ala Tyr Tyr Cys Ser Gly Ala Cys Gln Phe Pro Met Pro
1               5                   10                  15

Lys

```
<210> SEQ ID NO 18
<211> LENGTH: 14
<212> TYPE: PRT
<213> ORGANISM: Artificial Sequence
<220> FEATURE:
<223> OTHER INFORMATION: peptide fragment

<400> SEQUENCE: 18
```

Ser Leu Lys Pro Ser Asn Tyr Ala Thr Ile Gln Ser Ile Val
1               5                   10

```
<210> SEQ ID NO 19
<211> LENGTH: 21
<212> TYPE: PRT
<213> ORGANISM: Artificial Sequence
<220> FEATURE:
<223> OTHER INFORMATION: peptide fragment

<400> SEQUENCE: 19
```

Ala Cys Cys Val Pro Thr Glu Leu Ser Ala Ile Ser Met Leu Tyr Leu
1               5                   10                  15

Asp Glu Asn Glu Lys
            20

```
<210> SEQ ID NO 20
<211> LENGTH: 13
<212> TYPE: PRT
<213> ORGANISM: Artificial Sequence
<220> FEATURE:
<223> OTHER INFORMATION: peptide fragment

<400> SEQUENCE: 20
```

Met Ser Ser Leu Ser Ile Leu Phe Phe Asp Glu Asn Lys
1               5                   10

```
<210> SEQ ID NO 21
<211> LENGTH: 10
<212> TYPE: PRT
<213> ORGANISM: Artificial Sequence
<220> FEATURE:
<223> OTHER INFORMATION: peptide fragment

<400> SEQUENCE: 21
```

Ser Gln Glu Leu Tyr Val Asp Phe Gln Arg
1               5                   10

```
<210> SEQ ID NO 22
<211> LENGTH: 11
<212> TYPE: PRT
<213> ORGANISM: Artificial Sequence
<220> FEATURE:
<223> OTHER INFORMATION: peptide fragment
```

```
<400> SEQUENCE: 22

Phe Leu His Cys Gln Phe Ser Glu Arg Asn Ser
1               5                   10

<210> SEQ ID NO 23
<211> LENGTH: 15
<212> TYPE: PRT
<213> ORGANISM: Artificial Sequence
<220> FEATURE:
<223> OTHER INFORMATION: peptide fragment

<400> SEQUENCE: 23

Thr Val Gly Gln Leu Asn Glu Gln Ser Ser Glu Pro Asn Ile Tyr
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: peptide fragment

<400> SEQUENCE: 24

Leu Tyr Asp Pro Met Val Val
1               5

<210> SEQ ID NO 25
<211> LENGTH: 15
<212> TYPE: PRT
<213> ORGANISM: Artificial Sequence
<220> FEATURE:
<223> OTHER INFORMATION: peptide fragment

<400> SEQUENCE: 25

Val Gly Val Val Pro Gly Ile Pro Glu Pro Cys Cys Val Pro Glu
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: peptide fragment

<400> SEQUENCE: 26

Val Asp Phe Ala Asp Ile Gly
1               5

<210> SEQ ID NO 27
<211> LENGTH: 9
<212> TYPE: PRT
<213> ORGANISM: Artificial Sequence
<220> FEATURE:
<223> OTHER INFORMATION: peptide fragment

<400> SEQUENCE: 27

Val Pro Lys Pro Cys Cys Ala Pro Thr
1               5

<210> SEQ ID NO 28
<211> LENGTH: 7
<212> TYPE: PRT
<213> ORGANISM: Artificial Sequence
<220> FEATURE:
<223> OTHER INFORMATION: peptide fragment
```

```
<400> SEQUENCE: 28

Ile Asn Ile Ala Asn Tyr Leu
1               5

<210> SEQ ID NO 29
<211> LENGTH: 13
<212> TYPE: PRT
<213> ORGANISM: Artificial Sequence
<220> FEATURE:
<223> OTHER INFORMATION: peptide fragment

<400> SEQUENCE: 29

Asp Asn His Val Leu Thr Met Phe Pro Ile Ala Ile Asn
1               5                   10

<210> SEQ ID NO 30
<211> LENGTH: 16
<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (15)..(15)
<223> OTHER INFORMATION: wherein Xaa at position 15 is any amino acid

<400> SEQUENCE: 30

Asp Glu Gln Thr Leu Lys Lys Ala Arg Arg Lys Gln Trp Ile Xaa Pro
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (4)..(4)
<223> OTHER INFORMATION: wherein Xaa at position 4 is any amino acid
<220> FEATURE:
<221> NAME/KEY: misc_feature
<222> LOCATION: (10)..(10)
<223> OTHER INFORMATION: wherein Xaa at position 10 is any amino acid

<400> SEQUENCE: 31

Asp Ile Gly Xaa Ser Glu Trp Ile Ile Xaa Pro
1               5                   10

<210> SEQ ID NO 32
<211> LENGTH: 17
<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (15)..(16)
<223> OTHER INFORMATION: wherein Xaa at positions 15 and 16 is any amino
      acid

<400> SEQUENCE: 32

Ser Ile Val Arg Ala Val Gly Val Pro Gly Ile Pro Glu Pro Xaa Xaa
1               5                   10                  15

Val

<210> SEQ ID NO 33
<211> LENGTH: 13
```

<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (2)..(2)
<223> OTHER INFORMATION: wherein Xaa at position 2 is any amino acid

<400> SEQUENCE: 33

Asp Xaa Ile Val Ala Pro Pro Gln Tyr His Ala Phe Tyr
1               5                   10

<210> SEQ ID NO 34
<211> LENGTH: 17
<212> TYPE: PRT
<213> ORGANISM: Artificial Sequence
<220> FEATURE:
<223> OTHER INFORMATION: peptide fragment

<400> SEQUENCE: 34

Asp Glu Asn Lys Asn Val Val Leu Lys Val Tyr Pro Asn Met Thr Val
1               5                   10                  15

Glu

<210> SEQ ID NO 35
<211> LENGTH: 18
<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (13)..(13)
<223> OTHER INFORMATION: wherein Xaa at position 13 is any amino acid
<220> FEATURE:
<221> NAME/KEY: misc_feature
<222> LOCATION: (16)..(16)
<223> OTHER INFORMATION: wherein Xaa at position 16 is any amino acid

<400> SEQUENCE: 35

Ser Gln Thr Leu Gln Phe Asp Glu Gln Thr Leu Lys Xaa Ala Arg Xaa
1               5                   10                  15

Lys Gln

<210> SEQ ID NO 36
<211> LENGTH: 24
<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (19)..(19)
<223> OTHER INFORMATION: wherein Xaa at position 19 is any amino acid

<400> SEQUENCE: 36

Asp Glu Gln Thr Leu Lys Lys Ala Arg Arg Lys Gln Trp Ile Glu Pro
1               5                   10                  15

Arg Asn Xaa Ala Arg Arg Tyr Leu
            20

<210> SEQ ID NO 37
<211> LENGTH: 20
<212> TYPE: PRT
<213> ORGANISM: Artificial Sequence
<220> FEATURE:
<223> OTHER INFORMATION: peptide fragment

```
<220> FEATURE:
<221> NAME/KEY: misc_feature
<222> LOCATION: (12)..(12)
<223> OTHER INFORMATION: wherein Xaa at position 12 is any amino acid
<220> FEATURE:
<221> NAME/KEY: misc_feature
<222> LOCATION: (14)..(14)
<223> OTHER INFORMATION: wherein Xaa at position 14 is any amino acid
<220> FEATURE:
<221> NAME/KEY: misc_feature
<222> LOCATION: (17)..(18)
<223> OTHER INFORMATION: wherein Xaa at positions 17-18 is any amino
      acid

<400> SEQUENCE: 37

Ala Arg Arg Lys Gln Trp Ile Glu Pro Arg Asn Xaa Ala Xaa Arg Tyr
1               5                   10                  15

Xaa Xaa Val Asp
            20

<210> SEQ ID NO 38
<211> LENGTH: 23
<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (2)..(2)
<223> OTHER INFORMATION: wherein Xaa at position 2 is any amino acid
<220> FEATURE:
<221> NAME/KEY: misc_feature
<222> LOCATION: (8)..(8)
<223> OTHER INFORMATION: wherein Xaa at position 8 is any amino acid
<220> FEATURE:
<221> NAME/KEY: misc_feature
<222> LOCATION: (10)..(10)
<223> OTHER INFORMATION: wherein Xaa at position 10 is any amino acid
<220> FEATURE:
<221> NAME/KEY: misc_feature
<222> LOCATION: (12)..(13)
<223> OTHER INFORMATION: wherein Xaa at positions 12-13 is any amino
      acid
<220> FEATURE:
<221> NAME/KEY: misc_feature
<222> LOCATION: (19)..(19)
<223> OTHER INFORMATION: wherein Xaa at position 19 is any amino acid
<220> FEATURE:
<221> NAME/KEY: misc_feature
<222> LOCATION: (21)..(22)
<223> OTHER INFORMATION: wherein Xaa at positions 21-22 is any amino
      acid

<400> SEQUENCE: 38

Arg Xaa Gln Trp Ile Glu Pro Xaa Asn Xaa Ala Xaa Xaa Tyr Leu Lys
1               5                   10                  15

Val Asp Xaa Ala Xaa Xaa Gly
            20

<210> SEQ ID NO 39
<211> LENGTH: 97
<212> TYPE: PRT
<213> ORGANISM: mammalian
<220> FEATURE:
<223> OTHER INFORMATION: OP1 shorter sequence capable of inducing
      endochondral bone formation

<400> SEQUENCE: 39

Leu Tyr Val Ser Phe Arg Asp Leu Gly Trp Gln Asp Trp Ile Ile Ala
1               5                   10                  15

Pro Glu Gly Tyr Ala Ala Tyr Tyr Cys Glu Gly Glu Cys Ala Phe Pro
```

```
                    20                  25                  30
Leu Asn Ser Tyr Met Asn Ala Thr Asn His Ala Ile Val Gln Thr Leu
        35                  40                  45

Val His Phe Ile Asn Pro Glu Thr Val Pro Lys Pro Cys Cys Ala Pro
 50                  55                  60

Thr Gln Leu Asn Ala Ile Ser Val Leu Tyr Phe Asp Asp Ser Ser Asn
 65                  70                  75                  80

Val Ile Leu Lys Lys Tyr Arg Asn Met Val Arg Ala Cys Gly Cys
                85                  90                  95

His

<210> SEQ ID NO 40
<211> LENGTH: 4805
<212> TYPE: DNA
<213> ORGANISM: mammalian
<220> FEATURE:
      OTHER INFORMATION: genomic sequence of OP1

<220> FEATURE:
<221> NAME/KEY: misc_feature
<223> OTHER INFORMATION: approximately 1000 bases are missing between
      position 1883 and 188

<400> SEQUENCE: 40
ggaggtatag gagctctctt cgattttagc aaaccaggag tccgaagatc taaggagagc      60
tgggggtttg actccgagag ctcgagcagt ccccaagacc tggtcttgac tcacgagtta    120
gactccactc agaggctgac tgtctccagg gtctacacct ctaagggcga cactgggctc    180
aagcagactg ccgttttcta tatgggatga gccttcacag ggcagccagt tgggatgggt    240
tgaggtttgg ctgtagacat cagaaaccca agtcaaatgc gcttcaacca gtagaaaatt    300
caccagcccg cagagctaag gttgggtgga cattagggtt ggttgatcca ggagctcaac    360
agtgtcctct gagccccagc tccttctgcc ccaccccacc atcttcagtg ctgcttcctc    420
tcaaggccac agctgtagtt ggccagggggg gcttcattat ttttgctcc tgggcagtag    480 gaggaagaga atgaatgtct ctccatgggt ctttcttagg aatgtgggaa cttttccag    540 aagtctctat gtcttttagt ttgtgttggg tcacttgccc ttcctgaacc acttcctgac    600
tcctggacag gatgtgcact gatgagctta gctttgggga tctaatagtg actttacaaa    660
gcctctttga aaggtgaca ttggaaccaa ggcttgagca gacacaacaa agattgcagg    720
gaggggcatt gcaggtggag gaaacggcac atgcaagagc cctgcgtggg agtgagcttg    780
gtgtttggtc aatcagttgt cagagcacac cgggccctgt cagcaggcac agcctgggcc    840
tgctctgagt atgacagaga gcccctggga agttgtaggt ggaggaaaga caggtcatga    900
ctaggaaaaa agcaatccct ctgttgtggg gtggaaggaa ggttgcagtg tgtgtgagag    960
agagacaaga cagacagaca gacacttctc aatgtttaca agtgctcagg ccctgacccg   1020
aatgcttcca aatttacgta gttctggaaa accccctgta tcattttcac tactcaaaga   1080
aacctcggga gtgttttctt ctgaaaggtc atcaggtttt gactctctgc tgtctcattt   1140
cttcttgctg gtggtggtga tggttgcttg tcccaggccc tgtcccgcat cctcttgccc   1200
ctgcagaggg atgagtgtgt tggggcctca cgagttgagg ttgttcataa gcagatctct   1260
ttgagcaggg cgcctgcagt ggccttgtgt gaggctggag gggtttcgat tcccttatgg   1320
aatccaggca gatgtagcat ttaaacaaca cacgtgtata aaagaaacca gtgtccgcag   1380
aaggttccag aaagtattat gggataagac tacatgagag aggaatgggg cattggcacc   1440
```

```
tcccttagta gggcctttgc tgggggtaga aatgagtttt aaggcaggtt agaccctcga    1500
actggctttt gaatcgggaa atttaccccc cagccgttct gtgcttcatt gctgttcaca    1560
tcactgccta agatggagga actttgatgt gtgtgtgttt cttctcctc actgggctct     1620 gcttcttcac ttccttgtca atgcagagaa cagcagcagg caccagaggc aggccttgta    1680
agaagcacga gctgtatgtc agcttccgag acctgggctg gcaggtaagg ggctggctgg    1740
gtctgtcttg ggtgtgggcc ctctggcgtg ggctcccaca ggcagcgggt gctgtgctca    1800
gtcttgtttc tcatctctgc cagttaagac tccagtatca agtggcctcg ctagggaagg    1860
gtacttggct aaggatacag gggggagcca gcatgggtga tgccattatg agttattagc    1920
ctctctggca ggtgggcaaa ccgaggcatg gaggtttgtt taaggtgaac tgccagtgtg    1980
tgaccaccta gtggggtaga gctgatgatt gcctcacacc ggagctcctt cctgtgccgc    2040
gttctgtcca gaagacacag ccatggatgt ccatttagg atcagccaag ccccgtcttg      2100
tccttcattt ttattttatg ttttttaga aatgggtct tgctctgtca cccaggctgg       2160
gtgcagtggt gtgatcatag ctcaccgcag ctttgacgcc gtcttcccac tcagtctact    2220
aagcttggac tataggccaa gactatagag tggtccttct ttccattctt ttgggaccat    2280
gagaggccac ccatgtttcc tgcccctgct gggccctgct gctcagaagg catggtctga    2340
ggctttcacc ttggtcgtga gccttcgtgg tggtttcttt cagcatgggg ttgggatgct    2400
gtgctcaggc ttctgcatgg tttcccacac tctcttctcc tcctcaggac tggatcatcg    2460
cgcctgaagg ctacgcgcgc tactactgtg aggggagtg tgccttccct ctgaactcct      2520
acatgaacgc caccaaccac gccatcgtgc agacgctggt gggtgtcacg ccatcttggg    2580
gtgtggtcac ctgggccggg caggctgcgg ggccaccaga tcctgctgcc tccaagctgg    2640
ggcctgagta gatgtcagcc cattgccatg tcatgacttt tgggggcccc ttgcgccgtt    2700
aaaaaaaaat caaaaattgt actttatgac tggtttggta taaagaggag tataatcttc    2760
gaccctggag ttcatttatt tctcctaatt tttaaagtaa ctaaaagttg tatgggctcc    2820
tttgaggatg cttgtagtat tgtgggtgct ggttacggtg cctaagagca ctgggcccct    2880
gcttcatttt ccagtagagg aaacaggtaa acagatgaga aatttcagtg aggggcacag    2940
tgatcagaag cgggccagca ggataatggg atggagagat gagtgggac ccatgggcca     3000 tttcaagtta aatttcagtc gggtcaccag gaagattcca tgtgataatg agattaacgt    3060
gcccagtcac ggcgacactc agtaggtgtt attcctgctc tgccaacagc aaccatagtt    3120
gataagagct gttagggatt ttgtcctttt gcttagaatc caaggttcaa ggaccttggt    3180
tatgtagctc cctgtcatga acatcatctg agcctttcct gcctactgat catccaccct    3240
gccttgaatg cttctagtga cagagagctc actaccagga ctactccctc ctttcattta    3300
gtaatctgcc tccttctttt cttgtccctg tcctgtgtgt taagtcctgg agaaaaatct    3360
catctatccc tttcatttga ttctgctctt tgagggcagg ggttttttgtt tctttgtttg   3420 tttttttaag tgttggtttt ccaaagccct tgctccctc ctcaattgaa acttcaaagc      3480
cctcattggg attgaaggtc cttaggctgg aaacagaaga gtcctcccca acctgttccc    3540
tggcctggat gtgctgtgct gtgccagtat cccctggaag gtgccaggca tgtctccccg    3600
gctgccaggg gacacatctc tatccttctc caacccctgc cttcatggcc catgaacag     3660 gagtgccatc gccctgtgtg cacctacttc catcagtatt tcaccagaga tctgcaggat    3720
caaagtgaat tctccaggga ttgtgaaatg atgcgattgt ggtcatgttt aaaaggggc     3780 aactgtcttc tagagagtcc tgatgaaatg cttccagagg aaatgagctg atggctggaa    3840
```

```
tttgctttaa aatcattcaa ggtggagcag gtggggaagg gtatggatgt gtaagagttt    3900
gaaattgtcc atcataaaat gtgtaaaaag catgctggcc tatgtcagca gtcacagcct    3960
ggaggtggta acagagtgcc agtcactgat gctcaagcct ggcacctaca gttgctggaa    4020
acccagaagt ttcacgttga aaacaacagg acagtggaat ctctggccct gtcttgaaca    4080
cgtggcagat ctgctaacac tgatcttggt tggctgccgt cagcttaggt tgagtggcgg    4140
tcttccctta gtttgcttag tccccgctat tccctattgt cttacctcgg tctatttgc    4200 ttatcagtgg acctcacgag gcactcatag gcatttgagt ctatgtgtcc ctgtcccaca    4260
tcctctgtaa ggtgcagaga agtccatgag caagatggag cacttctagt gggtccaagt    4320
cagggacact attcagcaat ctacagtgca cagggcagtt ccccaacaga gaattacctg    4380
gtcctgaatg tcggatctgg ccccttcctt ccccactgta taatgtgaaa acctctatgc    4440
tttgttcccc ttgtctgcaa aacagggata atcccagaac tgagttgtcc atgtaaagtg    4500
cttagaacag ggagtgcttg gcttggggag tgtcacctgc agtcattcat tatgcccaga    4560
caggatgttt ctttatagaa acgtggaggc cagttagaac gactcaccgc ttctcaccac    4620
tgcccatgtt ttggtgtgtg tttcaggtcc acttcatcaa cccggaaacg gtgcccaagc    4680
cctgctgtgc gcccacgcag ctcaatgcca tctccgtcct ctacttcgat gacagctcca    4740
acgtcatcct gaagaaatac agaaacatgg tggtccgggc ctgtggctgc cactagctcc    4800
tccga                                                                4805

<210> SEQ ID NO 41
<211> LENGTH: 314
<212> TYPE: DNA
<213> ORGANISM: Artificial Sequence
<220> FEATURE:
<223> OTHER INFORMATION: consensus probe for OP1

<400> SEQUENCE: 41
gatcctaatg ggctgtacgt ggacttccag cgcgacgtgg gctgggacga ctggatcatc     60
gcccccgtcg acttcgacgc ctactactgc tccggagcct gccagttccc ctctgcggat    120
cacttcaaca gcaccaacca cgccgtggtg cagaccctgg tgaacaacat gaaccccggc    180
aaggtaccca gccctgctg cgtgcccacc gagctgtccg ccatcagcat gctgtacctg    240
gacgagaatt ccaccgtggt gctgaagaac taccaggaga tgaccgtggt gggctgcggc    300
tgccgctaac tgca                                                      314

<210> SEQ ID NO 42
<211> LENGTH: 314
<212> TYPE: DNA
<213> ORGANISM: mammalian
<220> FEATURE:
<223> OTHER INFORMATION: OP1

<400> SEQUENCE: 42
tgtaagaagc acgagctgta tgtcagcttc cgagacctgg gctggcagga ctggatcatc     60
gcgcctgaag gctacgcgcg ctactactgt gaggggagt gtgccttccc tctgaactcc    120
tacatgaacg ccaccaacca cgccatcgtg cagacgctgg tccacttcat caacccggaa    180
acggtgccca gccctgctg tgcgcccacg cagctcaatg ccatctccgt cctctacttc    240
gatgacagct ccaacgtcat cctgaagaaa tacagaaaca tggtggtccg ggcctgtggc    300
tgccactagc tcct                                                      314
```

```
<210> SEQ ID NO 43
<211> LENGTH: 315
<212> TYPE: DNA
<213> ORGANISM: Artificial Sequence
<220> FEATURE:
<221> NAME/KEY: CDS
<222> LOCATION: (1)..(306)
<223> OTHER INFORMATION: COPO

<400> SEQUENCE: 43 gat cct aat ggg ctg tac gtg gac ttc cag cgc gac gtg ggc tgg gac      48
Asp Pro Asn Gly Leu Tyr Val Asp Phe Gln Arg Asp Val Gly Trp Asp
1               5                   10                  15 gac tgg atc atc gcc ccc gtc gac ttc gac gcc tac tac tgc tcc gga      96
Asp Trp Ile Ile Ala Pro Val Asp Phe Asp Ala Tyr Tyr Cys Ser Gly
            20                  25                  30 gcc tgc cag ttc ccc tct gcg gat cac ttc aac agc acc aac cac gcc     144
Ala Cys Gln Phe Pro Ser Ala Asp His Phe Asn Ser Thr Asn His Ala
        35                  40                  45 gtg gtg cag acc ctg gtg aac aac atg aac ccc ggc aag gta ccc aag     192
Val Val Gln Thr Leu Val Asn Asn Met Asn Pro Gly Lys Val Pro Lys
    50                  55                  60 ccc tgc tgc gtg ccc acc gag ctg tcc gcc atc agc atg ctg tac ctg     240
Pro Cys Cys Val Pro Thr Glu Leu Ser Ala Ile Ser Met Leu Tyr Leu
65                  70                  75                  80 gac gag aat tcc acc gtg gtg ctg aag aac tac cag gag atg acc gtg     288
Asp Glu Asn Ser Thr Val Val Leu Lys Asn Tyr Gln Glu Met Thr Val
                85                  90                  95 gtg ggc tgc ggc tgc cgc taactgcag                                   315
Val Gly Cys Gly Cys Arg
            100

<210> SEQ ID NO 44
<211> LENGTH: 102
<212> TYPE: PRT
<213> ORGANISM: Artificial Sequence
<220> FEATURE:
<223> OTHER INFORMATION: COPO

<400> SEQUENCE: 44

Asp Pro Asn Gly Leu Tyr Val Asp Phe Gln Arg Asp Val Gly Trp Asp
1               5                   10                  15

Asp Trp Ile Ile Ala Pro Val Asp Phe Asp Ala Tyr Tyr Cys Ser Gly
            20                  25                  30

Ala Cys Gln Phe Pro Ser Ala Asp His Phe Asn Ser Thr Asn His Ala
        35                  40                  45

Val Val Gln Thr Leu Val Asn Asn Met Asn Pro Gly Lys Val Pro Lys
    50                  55                  60

Pro Cys Cys Val Pro Thr Glu Leu Ser Ala Ile Ser Met Leu Tyr Leu
65                  70                  75                  80

Asp Glu Asn Ser Thr Val Val Leu Lys Asn Tyr Gln Glu Met Thr Val
                85                  90                  95

Val Gly Cys Gly Cys Arg
            100

<210> SEQ ID NO 45
<211> LENGTH: 4
<212> TYPE: PRT
<213> ORGANISM: Artificial Sequence
<220> FEATURE:
<223> OTHER INFORMATION: Hinge region
```

<400> SEQUENCE: 45

Asp Pro Asn Gly
1

<210> SEQ ID NO 46
<211> LENGTH: 106
<212> TYPE: PRT
<213> ORGANISM: Artificial Sequence
<220> FEATURE:
<223> OTHER INFORMATION: beta-inhibin-a

<400> SEQUENCE: 46

Cys Cys Lys Lys Gln Phe Phe Val Ser Phe Lys Asp Ile Gly Trp Asn
1               5                  10                  15

Asp Trp Ile Ile Ala Pro Ser Gly Tyr His Ala Asn Tyr Cys Glu Gly
            20                  25                  30

Glu Cys Pro Ser His Ile Ala Gly Thr Ser Gly Ser Ser Leu Ser Phe
        35                  40                  45

His Ser Thr Val Ile Asn His Tyr Arg Met Arg Gly His Ser Pro Phe
    50                  55                  60

Ala Asn Leu Lys Ser Cys Cys Val Pro Thr Lys Leu Arg Pro Met Ser
65                  70                  75                  80

Met Leu Tyr Tyr Asp Asp Gly Gln Asn Ile Ile Lys Lys Asp Ile Gln
                85                  90                  95

Asn Met Ile Val Glu Glu Cys Gly Cys Ser
            100                 105

<210> SEQ ID NO 47
<211> LENGTH: 105
<212> TYPE: PRT
<213> ORGANISM: Artificial Sequence
<220> FEATURE:
<223> OTHER INFORMATION: beta-inhibin-b

<400> SEQUENCE: 47

Cys Cys Arg Gln Gln Phe Phe Ile Asp Phe Arg Ile Gly Trp Asn Asp
1               5                  10                  15

Trp Ile Ile Ala Pro Thr Gly Tyr Tyr Gly Asn Tyr Cys Glu Gly Ser
            20                  25                  30

Cys Pro Ala Tyr Leu Ala Gly Val Pro Gly Ser Ala Ser Ser Phe His
        35                  40                  45

Thr Ala Val Val Asn Gln Tyr Arg Met Arg Gly Leu Asn Pro Gly Thr
    50                  55                  60

Lys Val Asn Ser Cys Cys Ile Pro Thr Lys Leu Ser Thr Met Ser Met
65                  70                  75                  80

Leu Tyr Phe Asp Asp Glu Tyr Asn Ile Val Lys Arg Asp Val Pro Asn
                85                  90                  95

Met Ile Val Glu Glu Cys Gly Cys Ala
            100                 105

<210> SEQ ID NO 48
<211> LENGTH: 99
<212> TYPE: PRT
<213> ORGANISM: Artificial Sequence
<220> FEATURE:
<223> OTHER INFORMATION: TGF-beta-1

<400> SEQUENCE: 48

Cys Cys Val Arg Gln Leu Tyr Ile Asp Phe Arg Lys Asp Leu Gly Trp
1               5                  10                  15

Lys Trp Ile His Glu Pro Lys Gly Tyr His Ala Asn Phe Cys Leu Gly
            20                  25                  30

Pro Cys Pro Tyr Ile Trp Ser Leu Leu Asp Thr Gln Tyr Ser Lys Val
         35                  40                  45

Leu Ala Leu Tyr Asn Gln His Asn Pro Gly Ala Ser Ala Ala Pro Cys
     50                  55                  60

Cys Val Pro Gln Ala Leu Glu Pro Leu Pro Ile Val Tyr Tyr Val Gly
65                  70                  75                  80

Arg Lys Pro Lys Val Glu Gln Leu Ser Asn Met Ile Val Arg Ser Cys
                85                  90                  95

Lys Cys Ser

<210> SEQ ID NO 49
<211> LENGTH: 99
<212> TYPE: PRT
<213> ORGANISM: Artificial Sequence
<220> FEATURE:
<223> OTHER INFORMATION: TGF-beta-2

<400> SEQUENCE: 49

Cys Cys Leu Arg Pro Leu Tyr Ile Asp Phe Lys Arg Asp Leu Gly Trp
1               5                   10                  15

Lys Trp Ile His Glu Pro Lys Gly Tyr Asn Ala Asn Phe Cys Ala Gly
            20                  25                  30

Ala Cys Pro Tyr Leu Trp Ser Leu Ser Asp Thr Gln His Ser Arg Val
         35                  40                  45

Leu Ser Leu Tyr Asn Thr Ile Asn Pro Glu Ala Ser Ala Ser Pro Cys
     50                  55                  60

Cys Val Ser Gln Asp Leu Glu Pro Leu Thr Ile Leu Tyr Tyr Ile Gly
65                  70                  75                  80

Lys Thr Pro Lys Ile Glu Gln Leu Ser Asn Met Ile Val Lys Ser Cys
                85                  90                  95

Lys Cys Ser

<210> SEQ ID NO 50
<211> LENGTH: 99
<212> TYPE: PRT
<213> ORGANISM: Artificial Sequence
<220> FEATURE:
<223> OTHER INFORMATION: TGF-beta-3

<400> SEQUENCE: 50

Cys Cys Val Arg Pro Leu Tyr Ile Asp Phe Arg Gln Asp Leu Gly Trp
1               5                   10                  15

Lys Trp Val His Glu Pro Lys Gly Tyr Tyr Ala Asn Phe Cys Ser Gly
            20                  25                  30

Pro Cys Pro Tyr Leu Arg Ser Leu Ala Asp Thr Thr His Ser Thr Val
         35                  40                  45

Leu Gly Leu Tyr Asn Thr Leu Asn Pro Glu Ala Ser Ala Ser Pro Cys
     50                  55                  60

Cys Val Pro Gln Asp Leu Glu Pro Leu Thr Ile Leu Tyr Tyr Val Gly
65                  70                  75                  80

Arg Thr Pro Lys Val Glu Gln Leu Ser Asn Met Val Val Lys Ser Cys
                85                  90                  95

Lys Cys Ser

```
<210> SEQ ID NO 51
<211> LENGTH: 99
<212> TYPE: PRT
<213> ORGANISM: Artificial Sequence
<220> FEATURE:
<223> OTHER INFORMATION: MIS

<400> SEQUENCE: 51

Cys Ala Leu Arg Glu Leu Ser Val Asp Leu Arg Ala Glu Arg Ser Val
1               5                   10                  15

Leu Ile Pro Glu Thr Tyr Gln Ala Asn Asn Cys Gln Gly Val Cys Gly
            20                  25                  30

Trp Pro Gln Ser Asp Arg Asn Pro Arg Tyr Gly Asn His Val Val Leu
        35                  40                  45

Leu Leu Lys Met Gln Ala Arg Gly Ala Ala Leu Ala Arg Pro Pro Cys
50                  55                  60

Cys Val Pro Thr Ala Tyr Ala Gly Lys Leu Leu Ile Ser Leu Ser Glu
65                  70                  75                  80

Glu Arg Ile Ser Ala His His Val Pro Asn Met Val Ala Thr Glu Cys
                85                  90                  95

Gly Cys Arg

<210> SEQ ID NO 52
<211> LENGTH: 103
<212> TYPE: PRT
<213> ORGANISM: Artificial Sequence
<220> FEATURE:
<223> OTHER INFORMATION: Alpha-inhibin
<220> FEATURE:
<221> NAME/KEY: misc_feature
<222> LOCATION: (93)..(93)
<223> OTHER INFORMATION: wherein Xaa at position 93 is a threonine, a
      valine or a proline

<400> SEQUENCE: 52

Cys His Arg Val Ala Leu Asn Ile Ser Phe Gln Glu Leu Gly Trp Glu
1               5                   10                  15

Arg Trp Ile Val Tyr Pro Pro Ser Phe Ile Phe His Tyr Cys His Gly
            20                  25                  30

Gly Cys Gly Leu His Ile Pro Pro Asn Leu Ser Leu Pro Val Pro Gly
        35                  40                  45

Ala Pro Pro Thr Pro Ala Gln Pro Tyr Ser Leu Leu Pro Gly Ala Gln
50                  55                  60

Pro Cys Cys Ala Ala Leu Pro Gly Thr Met Arg Pro Leu His Val Arg
65                  70                  75                  80

Thr Thr Ser Asp Gly Gly Tyr Ser Phe Lys Tyr Glu Xaa Asn Leu Leu
                85                  90                  95

Thr Gln His Cys Ala Cys Ile
            100

<210> SEQ ID NO 53
<211> LENGTH: 861
<212> TYPE: DNA
<213> ORGANISM: Artificial Sequence
<220> FEATURE:
<221> NAME/KEY: CDS
<222> LOCATION: (1)..(852)
<223> OTHER INFORMATION: COP-5 fusion protein

<400> SEQUENCE: 53 atg aaa gca att ttc gta ctg aaa ggt tca ctg gac aga gat ctg gac    48
Met Lys Ala Ile Phe Val Leu Lys Gly Ser Leu Asp Arg Asp Leu Asp
```

```
tct cgt ctg gat ctg gac gtt cgt acc gac cac aaa gac ctg tct gat      96
Ser Arg Leu Asp Leu Asp Val Arg Thr Asp His Lys Asp Leu Ser Asp
        20                  25                  30 cac ctg gtt ctg gtc gac ctg gct cgt aac gac ctg gct cgt atc gtt     144
His Leu Val Leu Val Asp Leu Ala Arg Asn Asp Leu Ala Arg Ile Val
        35                  40                  45 act ccc ggg tct cgt tac gtt gcg gat ctg gaa ttc atg gct gac aac     192
Thr Pro Gly Ser Arg Tyr Val Ala Asp Leu Glu Phe Met Ala Asp Asn
        50                  55                  60 aaa ttc aac aag gaa cag cag aac gcg ttc tac gag atc ttg cac ctg     240
Lys Phe Asn Lys Glu Gln Gln Asn Ala Phe Tyr Glu Ile Leu His Leu
65                  70                  75                  80 ccg aac ctg aac gaa gag cag cgt aac ggc ttc atc caa agc ttg aag     288
Pro Asn Leu Asn Glu Glu Gln Arg Asn Gly Phe Ile Gln Ser Leu Lys
            85                  90                  95 gat gag ccc tct cag tct gcg aat ctg cta gcg gat gcc aag aaa ctg     336
Asp Glu Pro Ser Gln Ser Ala Asn Leu Leu Ala Asp Ala Lys Lys Leu
            100                 105                 110 aac gat gcg cag gca ccg aaa tcg gat cag ggg caa ttc atg gct gac     384
Asn Asp Ala Gln Ala Pro Lys Ser Asp Gln Gly Gln Phe Met Ala Asp
            115                 120                 125 aac aaa ttc aac aag gaa cag cag aac gcg ttc tac gag atc ttg cac     432
Asn Lys Phe Asn Lys Glu Gln Gln Asn Ala Phe Tyr Glu Ile Leu His
        130                 135                 140 ctg ccg aac ctg aac gaa gag cag cgt aac ggc ttc atc caa agc ttg     480
Leu Pro Asn Leu Asn Glu Glu Gln Arg Asn Gly Phe Ile Gln Ser Leu
145                 150                 155                 160 aag gat gag ccc tct cag tct gcg aat ctg cta gcg gat gcc aag aaa     528
Lys Asp Glu Pro Ser Gln Ser Ala Asn Leu Leu Ala Asp Ala Lys Lys
                165                 170                 175 ctg aac gat gcg cag gca ccg aag gat cct aat ggg ctg tac gtc gac     576
Leu Asn Asp Ala Gln Ala Pro Lys Asp Pro Asn Gly Leu Tyr Val Asp
            180                 185                 190 ttc agc gac gtg ggc tgg gac gac tgg att gtg gcc cca cca ggc tac     624
Phe Ser Asp Val Gly Trp Asp Asp Trp Ile Val Ala Pro Pro Gly Tyr
            195                 200                 205 cag gcc ttc tac tgc cat ggc gaa tgc cct ttc ccg cta gcg gat cac     672
Gln Ala Phe Tyr Cys His Gly Glu Cys Pro Phe Pro Leu Ala Asp His
        210                 215                 220 ttc aac agc acc aac cac gcc gtg gtg cag acc ctg gtg aac tct gtc     720
Phe Asn Ser Thr Asn His Ala Val Val Gln Thr Leu Val Asn Ser Val
225                 230                 235                 240 aac tcc aag atc cct aag gct tgc tgc gtg ccc acc gag ctg tcc gcc     768
Asn Ser Lys Ile Pro Lys Ala Cys Cys Val Pro Thr Glu Leu Ser Ala
                245                 250                 255 atc agc atg ctg tac ctg gac gag aat gag aag gtg gtg ctg aag aac     816
Ile Ser Met Leu Tyr Leu Asp Glu Asn Glu Lys Val Val Leu Lys Asn
            260                 265                 270 tac cag gag atg gta gta gag ggc tgc ggc tgc cgc taactgcag           861
Tyr Gln Glu Met Val Val Glu Gly Cys Gly Cys Arg
            275                 280
```

<210> SEQ ID NO 54
<211> LENGTH: 284
<212> TYPE: PRT
<213> ORGANISM: Artificial Sequence
<220> FEATURE:
<223> OTHER INFORMATION: COP-5 fusion protein

<400> SEQUENCE: 54

```
Met Lys Ala Ile Phe Val Leu Lys Gly Ser Leu Asp Arg Asp Leu Asp
1               5                   10                  15

Ser Arg Leu Asp Leu Asp Val Arg Thr Asp His Lys Asp Leu Ser Asp
            20                  25                  30

His Leu Val Leu Val Asp Leu Ala Arg Asn Asp Leu Ala Arg Ile Val
                35                  40                  45

Thr Pro Gly Ser Arg Tyr Val Ala Asp Leu Glu Phe Met Ala Asp Asn
        50                  55                  60

Lys Phe Asn Lys Glu Gln Gln Asn Ala Phe Tyr Glu Ile Leu His Leu
65                  70                  75                  80

Pro Asn Leu Asn Glu Glu Gln Arg Asn Gly Phe Ile Gln Ser Leu Lys
                85                  90                  95

Asp Glu Pro Ser Gln Ser Ala Asn Leu Leu Ala Asp Ala Lys Lys Leu
            100                 105                 110

Asn Asp Ala Gln Ala Pro Lys Ser Asp Gln Gly Gln Phe Met Ala Asp
        115                 120                 125

Asn Lys Phe Asn Lys Glu Gln Gln Asn Ala Phe Tyr Glu Ile Leu His
130                 135                 140

Leu Pro Asn Leu Asn Glu Glu Gln Arg Asn Gly Phe Ile Gln Ser Leu
145                 150                 155                 160

Lys Asp Glu Pro Ser Gln Ser Ala Asn Leu Leu Ala Asp Ala Lys Lys
                165                 170                 175

Leu Asn Asp Ala Gln Ala Pro Lys Asp Pro Asn Gly Leu Tyr Val Asp
            180                 185                 190

Phe Ser Asp Val Gly Trp Asp Trp Ile Val Ala Pro Pro Gly Tyr
        195                 200                 205

Gln Ala Phe Tyr Cys His Gly Glu Cys Pro Phe Pro Leu Ala Asp His
        210                 215                 220

Phe Asn Ser Thr Asn His Ala Val Val Gln Thr Leu Val Asn Ser Val
225                 230                 235                 240

Asn Ser Lys Ile Pro Lys Ala Cys Cys Val Pro Thr Glu Leu Ser Ala
                245                 250                 255

Ile Ser Met Leu Tyr Leu Asp Glu Asn Glu Lys Val Val Leu Lys Asn
            260                 265                 270

Tyr Gln Glu Met Val Val Glu Gly Cys Gly Cys Arg
        275                 280

<210> SEQ ID NO 55
<211> LENGTH: 15
<212> TYPE: PRT
<213> ORGANISM: Artificial Sequence
<220> FEATURE:
<223> OTHER INFORMATION: BOP

<400> SEQUENCE: 55

Ser Phe Asp Ala Tyr Tyr Cys Ser Gly Ala Cys Gln Phe Pro Ser
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: DPP

<400> SEQUENCE: 56

Gly Tyr Asp Ala Tyr Tyr Cys His Gly Lys Cys Pro Phe Phe Leu
```

-continued

```
1               5                  10                  15

<210> SEQ ID NO 57
<211> LENGTH: 15
<212> TYPE: PRT
<213> ORGANISM: Artificial Sequence
<220> FEATURE:
<223> OTHER INFORMATION: Vg1

<400> SEQUENCE: 57

Gly Tyr Met Ala Asn Tyr Cys Tyr Gly Glu Cys Pro Tyr Pro Leu
1               5                  10                  15

<210> SEQ ID NO 58
<211> LENGTH: 15
<212> TYPE: PRT
<213> ORGANISM: Artificial Sequence
<220> FEATURE:
<223> OTHER INFORMATION: inhibin

<400> SEQUENCE: 58

Gly Tyr His Ala Asn Tyr Cys Glu Gly Glu Cys Pro Ser His Ile
1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: TGF-beta

<400> SEQUENCE: 59

Gly Tyr His Ala Asn Phe Cys Leu Gly Pro Cys Pro Tyr Ile Trp
1               5                  10                  15

<210> SEQ ID NO 60
<211> LENGTH: 21
<212> TYPE: PRT
<213> ORGANISM: Artificial Sequence
<220> FEATURE:
<223> OTHER INFORMATION: BOP

<400> SEQUENCE: 60

Lys Arg Ala Cys Cys Val Pro Thr Glu Leu Ser Ala Ile Ser Met Leu
1               5                  10                  15

Tyr Leu Asp Glu Asn
            20

<210> SEQ ID NO 61
<211> LENGTH: 20
<212> TYPE: PRT
<213> ORGANISM: Artificial Sequence
<220> FEATURE:
<223> OTHER INFORMATION: Vg1

<400> SEQUENCE: 61

Leu Pro Cys Cys Val Pro Thr Lys Met Ser Pro Ile Ser Met Leu Phe
1               5                  10                  15

Tyr Asp Asn Asn
            20

<210> SEQ ID NO 62
<211> LENGTH: 20
<212> TYPE: PRT
<213> ORGANISM: Artificial Sequence
<220> FEATURE:
```

<223> OTHER INFORMATION: inhibin

<400> SEQUENCE: 62

Lys Ser Cys Cys Val Pro Thr Lys Leu Arg Pro Met Ser Met Leu Tyr
1               5                   10                  15

Tyr Asp Asp Gly
            20

<210> SEQ ID NO 63
<211> LENGTH: 19
<212> TYPE: PRT
<213> ORGANISM: Artificial Sequence
<220> FEATURE:
<223> OTHER INFORMATION: TGF-beta

<400> SEQUENCE: 63

Ala Pro Cys Cys Val Pro Gln Ala Leu Glu Pro Leu Pro Ile Val Tyr
1               5                   10                  15

Tyr Val Gly

<210> SEQ ID NO 64
<211> LENGTH: 20
<212> TYPE: PRT
<213> ORGANISM: Artificial Sequence
<220> FEATURE:
<223> OTHER INFORMATION: DPP

<400> SEQUENCE: 64

Lys Ala Cys Cys Val Pro Thr Gln Leu Asp Ser Val Ala Met Leu Tyr
1               5                   10                  15

Leu Asn Asp Gln
            20

<210> SEQ ID NO 65
<211> LENGTH: 5
<212> TYPE: PRT
<213> ORGANISM: Artificial Sequence
<220> FEATURE:
<223> OTHER INFORMATION: BOP

<400> SEQUENCE: 65

Leu Tyr Val Asp Phe
1               5

<210> SEQ ID NO 66
<211> LENGTH: 5
<212> TYPE: PRT
<213> ORGANISM: Artificial Sequence
<220> FEATURE:
<223> OTHER INFORMATION: DPP

<400> SEQUENCE: 66

Leu Tyr Val Asp Phe
1               5

<210> SEQ ID NO 67
<211> LENGTH: 5
<212> TYPE: PRT
<213> ORGANISM: Artificial Sequence
<220> FEATURE:
<223> OTHER INFORMATION: Vgl

<400> SEQUENCE: 67

Leu Tyr Val Glu Phe
1               5

```
<210> SEQ ID NO 68
<211> LENGTH: 5
<212> TYPE: PRT
<213> ORGANISM: Artificial Sequence
<220> FEATURE:
<223> OTHER INFORMATION: TGF-beta

<400> SEQUENCE: 68

Leu Tyr Ile Asp Phe
1               5

<210> SEQ ID NO 69
<211> LENGTH: 5
<212> TYPE: PRT
<213> ORGANISM: Artificial Sequence
<220> FEATURE:
<223> OTHER INFORMATION: inhibin

<400> SEQUENCE: 69

Phe Phe Val Ser Phe
1               5

<210> SEQ ID NO 70
<211> LENGTH: 5
<212> TYPE: PRT
<213> ORGANISM: Artificial Sequence
<220> FEATURE:
<223> OTHER INFORMATION: N-terminal sequence

<400> SEQUENCE: 70

Cys Lys Arg His Pro
1               5

<210> SEQ ID NO 71
<211> LENGTH: 5
<212> TYPE: PRT
<213> ORGANISM: Artificial Sequence
<220> FEATURE:
<223> OTHER INFORMATION: N-terminal sequence

<400> SEQUENCE: 71

Cys Arg Arg Lys Gln
1               5

<210> SEQ ID NO 72
<211> LENGTH: 5
<212> TYPE: PRT
<213> ORGANISM: Artificial Sequence
<220> FEATURE:
<223> OTHER INFORMATION: N-terminal sequence

<400> SEQUENCE: 72

Cys Lys Arg His Glu
1               5
```

NUCLEIC ACID MOLECULES ENCODING OSTEOGENIC PROTEINS

CROSS-REFERENCE TO RELATED APPLICATIONS

This application is a divisional application of U.S. Ser. No. 09/754,831, filed Jan. 3, 2001, now U.S. Pat. No. 7,078,221, which is a continuation of U.S. Ser. No. 08/375,901, filed Jan. 20, 1995, now U.S. Pat. No. 6,261,835, which is a divisional of U.S. Ser. No. 08/145,812, filed Nov. 1, 1993, now U.S. Pat. No. 5,750,651, which is a divisional of U.S. Ser. No. 07/995,345, filed Dec. 22, 1992, now U.S. Pat. No. 5,258,494, which is a divisional of U.S. Ser. No. 07/315,342, filed Feb. 23, 1989, now U.S. Pat. No. 5,011,691, the disclosures of all of which are incorporated herein by reference. This application—also relates to U.S. Ser. No. 07/232,630, entitled "Osteogenic Devices", filed Aug. 15, 1988, now abandoned, and U.S. Ser. No. 07/179,406, entitled "Osteogenic Devices", filed Apr. 8, 1988, now U.S. Pat. No. 4,968,590, the disclosures of both of which are hereby incorporated by reference.

BACKGROUND OF THE INVENTION

This invention relates to osteogenic devices, to genes encoding proteins which can induce osteogenesis in mammals and methods for their production using recombinant DNA techniques, to synthetic forms of osteogenic protein, to a method of reproducibly purifying osteogenic protein from mammalian bone, to matrix materials which act as a carrier to induce osteogenesis in mammals, and to bone and cartilage repair procedures using the osteogenic device.

Mammalian bone tissue is known to contain one or more proteinaceous materials, presumably active during growth and natural bone healing, which can induce a developmental cascade of cellular events resulting in endochondral bone formation. This active factor (or factors) has variously been referred to in the literature as bone morphogenetic or morphogenic protein, bone inductive protein, osteogenic protein, osteogenin, or osteoinductive protein.

The developmental cascade of bone differentiation consists of chemotaxis of mesenchymal cells, proliferation of progenitor cells, differentiation of cartilage, vascular invasion, bone formation, remodeling, and finally marrow differentiation (Reddi (1981) Collagen Rel. Res. 1: 209-226).

Though the precise mechanisms underlying these phenotypic transformations are unclear, it has been shown that the natural endochondral bone differentiation activity of bone matrix can be dissociatively extracted and reconstituted with inactive residual collagenous matrix to restore full bone induction activity (Sampath and Reddi, (1981) Proc. Natl. Acad. Sci. USA 21: 7599-7603). This provides an experimental method for assaying protein extracts for their ability to induce endochondral bone in vivo.

This putative bone inductive protein has been shown to have a molecular mass of less than 50 kilodaltons (kD). Several species of mammals produce closely related protein as demonstrated by cross species implant experiments (Sampath and Reddi (1983) Proc. Natl. Acad. Sci. USA 80: 6591-6595).

The potential utility of these proteins has been widely recognized. It is contemplated that the availability of the pure protein would revolutionize orthopedic medicine, certain types of plastic surgery, and various periodontal and craniofacial reconstructive procedures.

The observed properties of these protein fractions have induced an intense research effort in various laboratories directed to isolating and identifying the pure factor or factors responsible for osteogenic activity. The current state of the art of purification of osteogenic protein from mammalian bone is disclosed by Sampath et al. (Proc. Natl. Acad. Sci. USA (1987) 80). Urist et al. (Proc. Soc. Exp. Biol. Med. (1984) 17: 194-199) disclose a human osteogenic protein fraction which was extracted from demineralized cortical bone by means of a calcium chloride-urea inorganic-organic solvent mixture, and retrieved by differential precipitation in guanidine-hydrochloride and preparative gel electrophoresis. The authors report that the protein fraction has an amino acid composition of an acidic polypeptide and a molecular weight in a range of 17-18 kD.

Urist et al. (Proc. Natl. Acad. Sci. USA (1984) 11: 371-375) disclose a bovine bone morphogenetic protein extract having the properties of an acidic polypeptide and a molecular weight of approximately 18 kD. The authors reported that the protein was present in a fraction separated by hydroxyapatite chromatography, and that it induced bone formation in mouse hindquarter muscle and bone regeneration in trephine defects in rat and dog skulls. Their method of obtaining the extract from bone results in ill-defined and impure preparations.

European Patent Application Serial No. 148,155, published Oct. 7, 1985, purports to disclose osteogenic proteins derived from bovine, porcine, and human origin. One of the proteins, designated by the inventors as a P3 protein having a molecular weight of 22-24 kD, is said to have been purified to an essentially homogeneous state. This material is reported to induce bone formation when implanted into animals.

International Application No. PCT/087/01537, published Jan. 14, 1988, discloses an impure fraction from bovine bone which has bone induction qualities. The named applicants also disclose putative bone inductive factors produced by recombinant DNA techniques. Four DNA sequences were retrieved from human or bovine genomic or cDNA libraries and apparently expressed in recombinant host cells. While the applicants stated that the expressed proteins may be bone morphogenic proteins, bone induction was not demonstrated, suggesting that the recombinant proteins are not osteogenic. See also Urist et al., EP 0,212,474 entitled Bone Morphogenic Agents.

Wang et al. (Proc. Nat. Acad. Sci. USA (1988) 85: 9484-9488) discloses the purification of a bovine bone morphogenetic protein from guanidine extracts of demineralized bone having cartilage and bone formation activity as a basic protein corresponding to a molecular weight of 30 kD determined from gel elution. Purification of the protein yielded proteins of 30, 18 and 16 kD which, upon separation, were inactive. In view of this result, the authors acknowledged that the exact identity of the active material had not been determined.

Wozney et al. (Science (1988) 242: 1528-1534) discloses the isolation of full-length cDNA's encoding the human equivalents of three polypeptides originally purified from bovine bone. The authors report that each of the three recombinantly expressed human proteins are independently or in combination capable of inducing cartilage formation. No evidence of bone formation is reported.

It is an object of this invention to provide osteogenic devices comprising matrices containing dispersed osteogenic protein capable of bone induction in allogenic and xenogenic implants. Another object is to provide a reproducible method of isolating osteogenic protein from mammalian bone tissue. Another object is to characterize the protein responsible for osteogenesis. Another object is to provide natural and recombinant osteogenic proteins capable of inducing endochondral bone formation in mammals, including humans. Yet another object is to provide genes encoding native and non-native osteogenic proteins and methods for their production using recombinant DNA techniques. Another object is to provide novel biosynthetic forms of osteogenic proteins and a structural design for novel, functional osteogenic proteins. Another object is to provide a suitable deglycosylated collagenous bone matrix as a carrier for osteogenic protein for use in zenogenic implants. Another object is to provide methods for inducing cartilage formation.

These and other objects and features of the invention will be apparent from the description, drawings, and claims which follow.

SUMMARY OF THE INVENTION

This invention involves osteogenic devices which, when implanted in a mammalian body, can induce at the locus of the implant the full developmental cascade of endochondral bone formation and bone marrow differentiation. Suitably modified as disclosed herein, the devices also may be used to induce cartilage formation. The devices comprise a carrier material, referred to herein as a matrix, having the characteristics disclosed below, containing dispersed osteogenic protein either in its native form or in the form of a biosynthetic construct.

A key to these developments was the elucidation of amino acid sequence and structure data of native osteogenic protein. A protocol was developed which results in retrieval of active, substantially pure osteogenic protein from mammalian bone. Investigation of the properties and structure of the native form osteogenic protein then permitted the inventors to develop a rational design for non-native forms, i.e., forms never before known in nature, capable of inducing bone formation. As far as applicants are aware, the constructs disclosed herein constitute the first instance of the design of a functional, active protein without preexisting knowledge of the active region of a native form nucleotide or amino acid sequence.

A series of consensus DNA sequences were designed with the goal of producing an active osteogenic protein. The sequences were based on partial amino acid sequence data obtained from the natural source product and on observed homologies with unrelated genes reported in the literature, or the sequences they encode, having a presumed or demonstrated developmental function. Several of the biosynthetic consensus sequences have been expressed as fusion proteins in procaryotes, purified, cleaved, refolded, combined with a matrix, implanted in an established animal model, and shown to have endochondral bone-inducing activity. The currently preferred active totally biosynthetic proteins comprise two synthetic sequences designated COP5 and COP7. The amino acid sequences of these proteins are set forth below.

```
        1         10        20        30        40
COP5         LYVDFS-DVGWDDWIVAPPGYQAFYCHGECPFPLAD
                 50        60        70
        HFNSTN--H-AVVQTLVNSVNSKI--PKACCVPTELSA
                 80        90        100
        ISMLYLDENEKVVLKNYQEMVVEGCGCR
        (SEQ ID NO: 1)

1         10        20        30        40
COP7         LYVDFS-DVGWNDWIVAPPGYHAFYCHGECPFPLAD
                 50        60        70
        HLNSTN--H-AVVQTLVNSVNSKI--PKACCVPTELSA
                 80        90        100
        ISMLYLDENEKVVLKNYQEMVVEGCGCR
        (SEQ ID NO: 2)
```

In these sequences and all other amino acid sequences disclosed herein, the dashes (–) are used as fillers only to line up comparable sequences in related proteins, and have no other function. Thus, amino acids 45-50 of COP7, for example, are NHAVV. Also, the numbering of amino acids is selected solely for purposes of facilitating comparisons between sequences. Thus, for example, the DF residues numbered at 9 and 10 of COP5 and COP7 may comprise residues, e.g., 35 and 36, of an osteogenic protein embodying invention.

Thus, in one aspect, the invention comprises a protein comprising an amino acid sequence sufficiently duplicative of the sequence of COP5 or COP7 such that it is capable of inducing endochondral bone formation when properly folded and implanted in a mammal in association with a matrix. Some of these sequences induce cartilage, but not bone. Also, the bone forming materials may be used to produce cartilage if implanted in an avascular locus, or if an inhibitor to full bone development is implanted together with the active protein. Thus, in another aspect, the invention comprises a protein less than about 200 amino acids long in a sequence sufficiently duplicative of the sequence of COP5 or COP7 such that it is capable at least of cartilage formation when properly folded and implanted in a mammal in association with a matrix.

In one preferred aspect, these proteins comprise species of the generic amino acid sequences (SEQ ID NO: 3):

```
1         10        20        30        40        50
     LXVXFXDXGWXXWXXXPXGXXAXYCXGXCXXPXXXXXXXXXNHAXX
           60        70        80        90
QXXVXXXNXXXXPXXCCXPXXXXXXXXXLXXXXXXXXVXLXXYXXMXVX

100
XCXCX
or 1         10        20        30        40        50
CXXXXLXVXFXDXGWXXWXXXPXGXXAXYCXGXCXXPXXXXXXXXXNHAXX
           60        70        80        90
QXXVXXXNXXXXPXXCCXPXXXXXXXXXLXXXXXXXXVXLXXYXXMXVX

100
XCXCX
(SEQ ID NO: 4)
``` where the letters indicate the amino acid residues of standard single letter code, and the Xs represent amino acid residues. Preferred amino acid sequences within the foregoing generic sequences are:

```
1         10        20        30        40        50
     LYVDFRDVGWNDWIVAPPGYHAFYCHGECPFPLADHLNSTNHAIV
      K S S L   QE VIS E FD Y    E A AY MPESMKAS    VI
      F E K I   DN    L   N S    Q   ITK F P        TL
        A       S     K 60        70        80        90
QTLVNSVNPGKIPKACCVPTELSAISMLYLDENENVVLKNYQDMVVE
 SI HAI SEQV EP  A   EQMNSLAI FFNDQDK  I RK EE  T
    RF    T  S       K DPV V  Y N S      H RN   R
    N     S                             K       P

100
GCGCR
DA H H
S
E
(SEQ ID NO: 5)
and 1         10        20        30        40        50
CKRHPLYVDFRDVGWNDWIVAPPGYHAFYCHGECPFPLADHLNSTNHAIV
```

```
            -continued
RRRS K S S L  QE VIS E FD Y  E A AY MPESMKS    VI
  KE F E K I  DN     L  N S Q ITK F P          TL
     Q   A    S         K
```

```
                60        70        80        90
QTLVNSVNPGKIPKACCVPTELSAISMLYLDENENVVLKNYQDMVVE
 SI HAI SEQV EP A   EQMNSLAI FFNDQDK I RK EE  T
    RF   T   S      K DPV V Y N S      H RN   R
     N   S                          K         P

100
GCGCR
DA H H
S
E
(SEQ ID NO: 6)
``` wherein each of the amino acids arranged vertically at each position in the sequence may be used alternatively in various combinations. Note that these generic sequences have 6 and preferably 7 cysteine residues where inter- or intramolecular disulfide bonds can form, and contain other critical amino acids which influence the tertiary structure of the proteins. These generic structural features are found in previously published sequences, none of which have been described as capable of osteogenic activity, and most of which never have been linked with such activity.

Particular useful sequences include:

```
            1         10         20        30         40
Vg1         CKKRHLYVEFK-DVGWQNWVIAPQGYMANYCYGECPYPLTE
                       50        60         70
            ILNGSN--H-AILQTLVHSIEPED-IPLPCCVPTKMSP
                       80        90        100
            ISMLFYDNNDNVVLRHYENMAVDECGCR
            (SEQ ID NO: 7)

1         10         20        30         40
DPP         CRRHSLYVDFS-DVGWDDWIVAPLGYDAYYCHGKCPFPLAD
                       50        60         70
            HFNSTN--H-AVVQTLVNNNNPGK-VPKACCVPTQLDS
                       80        90        100
            VAMLYLNDQSTVVLKNYQEMTVVGCGCR
            (SEQ ID NO: 8)

-5
                                       HQRQA
            1         10         20        30         40
OP1         CKKHELYVSFR-DLGWQDWIIAPEGYAAYYCEGECAFPLNS
                       50        60         70
            YMNATN--H-AIVQTLVHFINPET-VPKPCCAPTQLNA
                       80        90        100
            ISVLYFDDSSNVILKKYRNMVVRACGCH
            (SEQ ID NO: 9)

1         10         20        30         40
CBMP-2a     CKRHPLYVDFS-DVGWNDWIVAPPGYHAFYCHGECPFPLAD
                       50        60         70
            HLHSTN--H-AIVQTLVNSVNS-K-IPKACCVPTELSA
                       80        90        100
            ISMLYLDENEKVVLKNYQDMVVEGCGCR
            (SEQ ID NO: 10)

1         10         20        30         40
CBMP-2b     CRRHSLYVDFS-DVGWNDWIVAPPGYQAFYCHGDCPFPLAD
                       50        60         70
            HLNSTN--H-AIVQTLVNSVNS-S-IPKACCVPTELSA
                       80        90        100
            ISMLYLDEYDKVVLKNYQEMVVEGCGCR
            (SEQ ID NO: 11)

1         10         20        30         40
CBMP-3      CARRYLKVDFA-DIGWSEWIISPKSFDAYYCSGACQFPMPK
                       50        60         70
            SLKPSN--H-ATIQSIVRAVGVVPGIPEPCCVPEKMSS
                       80        90        100
            LSILFFDENKNVVLKVYPNMTVESCACR
            (SEQ ID NO: 12)

1         10         20        30         40
COP1        LYVDFQRDVGWDDWIIAPVDFDAYYCSGACQFPSAD
                       50        60         70
            HFNSTN--H-AVVQTLVNNMNPGK-VPKPCCVPTELSA
                       80        90        100
            ISMLYLDENSTVVLKNYQEMTVVGCGCR
            (SEQ ID NO: 13)

1         10         20        30         40
COP3        LYVDFQRDVGWDDWIVAPPGYQAFYCSGACQFPSAD
                       50        60         70
            HFNSTN--H-AVVQTLVNNMNPGK-VPKPCCVPTELSA
                       80        90        100
            ISMLYLDENEKVVLKNYQEMVVEGCGCR
            (SEQ ID NO: 14)

1         10         20        30         40
COP4        LYVDFS-DVGWDDWIVAPPGYQAFYCSGACQFPSAD
                       50        60         70
            HFNSTN--H-AVVQTLVNNMNPGK-VPKPCCVPTELSA
                       80        90        100
            ISMLYLDENEKVVLKNYQEMVVEGCGCR
            (SEQ ID NO: 15)

-10
                                       PKHHSQRARKKNKN
            1         10         20        30         40
COP16       CRRHSLYVDFS-DVGWNDWIVAPPGYQAFYCHGECPFPLAD
                       50        60         70
            HFNSTN--H-AVVQTLVNSVNSKI--PKACCVPTELSA
                       80        90        100
            ISMLYLDENEKVVLKNYQEMVVEGCGCR
            (SEQ ID NO: 16)
```

Vg1 is a known *Xenopus* sequence heretofore not associated with bone formation. DPP is an amino acid sequence encoded by a *drosophila* gene responsible for development of the dorsoventral pattern. OP1 is a region of a natural sequence encoded by exons of a genomic DNA sequence retrieved by applicants. The CBMPs are amino acid sequences comprising subparts of mammalian proteins encoded by genomic DNAs and cDNAs retrieved by applicants. The COPs are biosynthetic protein sequences expressed by novel consensus gene constructs, designed using the criteria set forth herein, and not yet found in nature.

These proteins are believed to dimerize during refolding. They appear not to be active when reduced. Various combinations of species of the proteins, i.e., heterodimers, have activity, as do homodimers. As far as applicants are aware, the COP5 and COP7 constructs constitute the first instances of the design of a bioactive protein without preexisting knowledge of the active region of a native form nucleotide or amino acid sequence.

The invention also provides native forms of osteogenic protein, extracted from bone or produced using recombinant DNA techniques. The substantially pure osteogenic protein may include forms having varying glycosylation patterns, varying N-termini, a family of related proteins having regions of amino acid sequence homology, and active truncated or mutated forms of native protein, no matter how derived. The osteogenic protein in its native form is glycosylated and has an apparent molecular weight of about 30 kD as determined by SDS-PAGE. When reduced, the 30 kD protein gives rise to two glycosylated polypeptide chains having apparent molecular weights of about 16 kD and 18 kD. In the reduced state, the 30 kD protein has no detectable osteogenic activity. The deglycosylated protein, which has osteogenic activity, has an apparent molecular weight of about 27 kD. When reduced, the 27 kD protein gives rise to the two deglycosylated polypeptides have molecular weights of about 14 kD to 16 kD.

Analysis of digestion fragments indicate that the native 30 kD osteogenic protein contains the following amino acid sequences (question marks indicate undetermined residues):

```
(1)   S-F-D-A-Y-Y-C-S-G-A-C-Q-F-P-M-P-K;
      (SEQ ID NO: 17)

(2)   S-L-K-P-S-N-Y-A-T-I-Q-S-I-V;
      (SEQ ID NO: 18)

(3)   A-C-C-V-P-T-E-L-S-A-I-S-M-L-Y-L-D-E-N-E-K;
      (SEQ ID NO: 19)

(4)   M-S-S-L-S-I-L-F-F-D-E-N-K;
      (SEQ ID NO: 20)

(5)   S-Q-E-L-Y-V-D-F-Q-R;
      (SEQ ID NO: 21)

(6)   F-L-H-C-Q-F-S-E-R-N-S;
      (SEQ ID NO: 22)

(7)   T-V-G-Q-L-N-E-Q-S-S-E-P-N-I-Y;
      (SEQ ID NO: 23)

(8)   l-y-d-p-m-v-v;
      (SEQ ID NO: 24)

(9)   V-G-V-V-P-G-I-P-E-P-C-C-V-P-E;
      (SEQ ID NO: 25)

(10)  V-D-F-A-D-I-G;
      (SEQ ID NO: 26)

(11)  V-P-K-P-C-C-A-P-T;
      (SEQ ID NO: 27)

(12)  I-N-I-A-N-Y-L;
      (SEQ ID NO: 28)

(13)  D-N-H-V-L-T-M-F-P-I-A-I-N;
      (SEQ ID NO: 29)

(14)  D-E-Q-T-L-K-K-A-R-R-K-Q-W-I-?-P;
      (SEQ ID NO: 30)

(15)  D-I-G-?-S-E-W-I-I-?-P;
      (SEQ ID NO: 31)

(16)  S-I-V-R-A-V-G-V-P-G-I-P-E-P-?-?-V;
      (SEQ ID NO: 32)

(17)  D-?-I-V-A-P-P-Q-Y-H-A-F-Y;
      (SEQ ID NO: 33)

(18)  D-E-N-K-N-V-V-L-K-V-Y-P-N-M-T-V-E;
      (SEQ ID NO: 34)

(19)  S-Q-T-L-Q-F-D-E-Q-T-L-K-?-A-R-?-K-Q;
      (SEQ ID NO: 35)

(20)  D-E-Q-T-L-K-K-A-R-R-K-Q-W-I-E-P-R-N-?-A-R-R-Y
      -L;
      (SEQ ID NO: 36)

(21)  A-R-R-K-Q-W-I-E-P-R-N-?-A-?-R-Y-?-?-V-D;
      (SEQ ID NO: 37)
and
(22)  R-?-Q-W-I-E-P-?-N-?-A-?-?-Y-L-K-V-D-?-A-?-?
      -G.
      (SEQ ID NO: 38)
```

The substantially pure (i.e., free of contaminating proteins having no osteoinductive activity) osteogenic proteins and the synthetics are useful in clinical applications in conjunction with a suitable delivery or support system (matrix). The matrix is made up of particles or porous materials. The pores must be of a dimension to permit progenitor cell migration and subsequent differentiation and proliferation. The particle size should be within the range of 70-850 mm, preferably 70-420 mm. It may be fabricated by close packing particulate material into a shape spanning the bone defect, or by otherwise structuring as desired a material that is biocompatible (non-inflammatory) and, biodegradable in vivo to serve as a "temporary scaffold" and substratum for recruitment of migratory progenitor cells, and as a base for their subsequent anchoring and proliferation. Currently preferred carriers include particulate, demineralized, guanidine extracted, species-specific (allogenic) bone, and particulate, deglycosglated, protein extracted, demineralized, zenogenic bone. Optionally, such xenogenic bone powder matrices also may be treated with proteases such as trypsin. Other useful matrix materials comprise collagen, homopolymers and copolymers of glycolic acid and lactic acid, hydroxyapatite, tricalcium phosphate and other calcium phosphates.

The availability of the protein in substantially pure form, and knowledge of its amino acid sequence and other structural features, enable the identification, cloning, and expression of native genes which encode osteogenic proteins. When properly modified after translation, incorporated in a suitable matrix, and implanted as disclosed herein, these proteins are operative to induce formation of cartilage and endochondral bone.

The consensus DNA sequences are also useful as probes for extracting genes encoding osteogenic protein from genomic and cDNA libraries. One of the consensus sequences has been used to isolate a heretofore unidentified genomic DNA sequence, portions of which when ligated encode a protein having a region capable of inducing endochondral bone formation. This protein, designated OP1, has an active region having the sequence set forth below.

```
            1         10        20        30        40
    OP1     LYVSFR-DLGWQDWIIAPEGYAAYYCEGECAFPLNS
                      50        60        70
            YMNATN--H-AIVQTLVHFINPET-VPKPCCAPTQLNA
                      80        90        100
            ISVLYFDDSSNVILKKYRNMVVRACGCH
            (SEQ ID NO: 39)

A longer active sequence is:
                                                   -5
                                                 HQRQA
            1         10        20        30        40
    OP1   CKKHELYVSFR-DLGWQDWIIAPEGYAAYYCEGECAFPLNS
                      50        60        70
            YMNATN--H-AIVQTLVHFINPET-VPKPCCAPTQLNA
                      80        90        100
            ISVLYFDDSSNVILKKYRNMVVRACGCH
            (SEQ ID NO: 9)
```

FIG. 1A discloses the genomic DNA sequence of OP1 (SEQ ID NO: 40).

The probes have also retrieved the DNA sequences identified in PCT/087/01537, referenced above, designated therein as BMPII(b) and BMPIII. The inventors herein have discovered that certain subparts of these genomic DNAs, and BMPIIa, from the same publication, when properly assembled, encode proteins (CBMPIIa, CBMPIIb, and CBMPIII) which have true osteogenic activity, i.e., induce the full cascade of events when properly implanted in a mammal leading to endochondral bone formation.

Thus, in view of this disclosure, skilled genetic engineers can design and synthesize genes or isolate genes from cDNA or genomic libraries which encode appropriate amino acid sequences, and then can express them in various types of host cells, including both procaryotes and eucaryotes, to produce large quantities of active proteins in native forms, truncated analogs, muteins, fusion proteins, and other constructs capable of inducing bone formation in mammals including humans.

The osteogenic proteins and implantable osteogenic devices enabled and disclosed herein will permit the physician to obtain optimal predictable bone formation to correct, for example, acquired and congenital craniofacial and other skeletal or dental anomalies (Glowacki et al. (1981) Lancet 1: 959-963). The devices may be used to induce local endochondral bone formation in non-union-fractures as demonstrated in animal tests, and in other clinical applications including periodontal applications where bone formation is required. The other potential clinical application is in cartilage repair, for example, in the treatment of osteoarthritis.

BRIEF DESCRIPTION OF THE DRAWINGS

The foregoing and other objects of this invention, the various features thereof, as well as the invention itself, may be more fully understood from the following description, when read together with the accompanying drawings, in which:

FIG. 1A represents the nucleotide sequence of the genomic copy of osteogenic protein "OP1" gene (SEQ ID NO:40). The unknown region between 1880 and 1920 actually represents about 1000 nucleotides.

FIG. 1B is a representation of the hybridization of the consensus gene/probe to the osteogenic protein "OP1" gene (SEQ ID NO:42).

FIG. 3 is a photographic reproduction of a Coomassie blue stained SDS polyacrylamide gel of the osteogenic protein under non-reducing (A) and reducing (B) conditions;

FIG. 4 is a photographic reproduction of a Con A blot of an SDS polyacrylamide gel showing the carbohydrate component of oxidized (A) and reduced (B) 30 kD protein;

FIG. 5 is a photographic reproduction of an autoradiogram of an SDS polyacrylamide gel of $^{125}$I-labelled glycosylated (A) and deglycosylated (B) osteogenic protein under non-reducing (1) and reducing (2) conditions;

FIG. 13 is a schematic representation of the DNA sequence (SEQ ID NO:43) and corresponding amino acid sequence (SEQ ID NO:44) of a consensus gene/probe for osteogenic protein (COPO);

FIG. 18 is a comparison of the amino acid sequence of various osteogenic proteins to those of the TGF-beta family. COP1 (SEQ ID NO: 13), COP3 (SEQ ID NO: 14), COP4 (SEQ ID NO: 15), COP5 (SEQ ID NO: 1), and COP7 (SEQ ID NO: 2) are a family of analogs of synthetic osteogenic proteins developed from the consensus gene that was joined to a leader protein via a hinge region having the sequence D-P-N-G (SEQ ID NO: 45) that permitted chemical cleavage at the D-P site (by acid) or N-G (by hydroxylamine) resulting in the release of the analog protein; VGI (SEQ ID NO: 7) is a *Xenopus* protein, DPP (SEQ ID NO: 8) is a *Drosophila* protein; OP1 (amino acids 6-x of SEQ ID NO: 9) is a native osteogenic protein; CBMP2a (SEQ ID NO: 10) and 2b (SEQ ID NO: 11), and CBMP3 (SEQ ID NO: 12) are subparts of proteins disclosed in PCT application 087/01537; beta-Inhibin a) is shown in SEQ ID NO: 46, beta-Inhibin b) is shown in SEQ ID NO: 47, TGF-beta 1 is shown in SEQ ID NO: 48, TGF-beta 2 is shown in SEQ ID NO: 49, TGF-beta 3 is shown in SEQ ID NO: 50; MIS (SEQ ID NO: 51) is Mullerian inhibitory substance; alpha-Inhibin is shown in SEQ ID NO: 52; and "consensus choices" represent various substitutions of amino acids that may be made at various positions in osteogenic proteins;

FIG. 21B is the DNA sequence (SEQ ID NO:53) and amino acid sequence (SEQ ID NO:54) comprising a modified trp-LE leader, two Fb domains of protein A, an ASP-PRO cleavage site, and the COP5 sequence.

DESCRIPTION

Figure 2A:
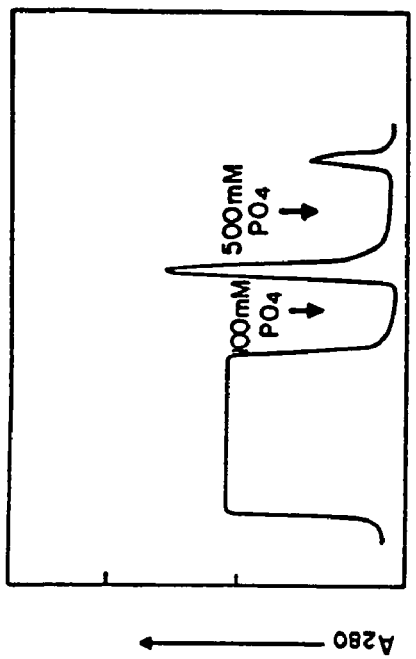
FIG. 2 is a collection of plots of protein concentration (as indicated by optical absorption) vs elution volume illustrating the results of bovine osteogenic protein (BOP) fractionation during purification on heparin-Sepharose-I; HAP-Ultragel; sieving gel (Sephacryl 300); and heparin-Sepharose-II.

Purification protocols have been developed which enable isolation of the osteogenic protein present in crude protein extracts from mammalian bone. While each of the separation steps constitute known separation techniques, it has been discovered that the combination of a sequence of separations exploiting the protein's affinity for heparin and for hydroxyapatite (HAP) in the presence of a denaturant such as urea is key to isolating the pure protein from the crude extract. These critical separation steps are combined with separations on hydrophobic media, gel exclusion chromatography, and elution form SDS PAGE.

The isolation procedure enables the production of significant quantities of substantially pure osteogenic protein from any mammalian species, provided sufficient amounts of fresh bone from the species is available. The empirical development of the procedure, coupled with the availability of fresh calf bone, has enabled isolation of substantially pure bovine osteogenic protein (BOP). BOP has been characterized significantly as set forth below; its ability to induce cartilage and ultimately endochondral bone growth in cat, rabbit, and rat have been studied; it has been shown to be able to induce the full developmental cascade of bone formation previously ascribed to unknown protein or proteins in heterogeneous bone extracts; and it may be used to induce formation of endochondral bone in orthopedic defects including nonunion fractures. In its native form it is a glycosylated, dimeric protein. However, it is active in deglycosylated form. It has been partially sequenced. Its primary structure includes the amino acid sequences set forth herein.

Elucidation of the amino acid sequence of BOP enables the construction of pools of nucleic acid probes encoding peptide fragments. Also, a consensus nucleic acid sequence designed as disclosed herein based on the amino acid sequence data, inferred codons for the sequences, and observation of partial homology with known genes, also may be used as a probe. The probes may be used to isolate naturally occurring cDNAs which encode active mammalian osteogenic proteins (OP) as described below using standard hybridization methodology. The mRNAs are present in the cytoplasm of cells of various species which are known to synthesize osteogenic proteins. Useful cells harboring the mRNAs include, for example, osteoblasts from bone or osteosarcoma, hypertrophic chondrocytes, and stem cells. The mRNAs can be used to produce cDNA libraries. Alternatively, relevant DNAs encoding osteogenic protein may be retrieved from cloned genomic DNA libraries from various mammalian species.

The consensus sequence described above also may be refined by comparison with the sequences present in certain regulatory genes from *drosophila, zenopus*, and human followed by point mutation, expression, and assay for activity. This approach has been successful in producing several active totally synthetic constructs not found in nature (as far as applicants are aware) which have true osteogenic activity.

These discoveries enable the construction of DNAS encoding totally novel, non-native protein constructs which individually, and combined are capable of producing true endochondral bone. They also permit expression of the natural material, truncated forms, muteins, analogs, fusion proteins, and various other variants and constructs, from cDNAs retrieved from natural sources or synthesized using the techniques disclosed herein using automated, commercially available equipment. The DNAs may be expressed using well established recombinant DNA technologies in procaryotic or eucaryotic host cells, and may be oxidized and refolded in vitro if necessary for biological activity.

The isolation procedure for obtaining the protein from bone, the retrieval of an osteogenic protein gene, the design and production of biosynthetics, the nature of the matrix, and other material aspects concerning the nature, utility, how to make, and how to use the subject matter claimed herein will be further understood from the following, which constitutes the best method currently known for practicing the various aspects of the invention.

I. Naturally Sourced Osteogenic Protein

A—PURIFICATION

A1. Preparation of Demineralized Bone

Demineralized bovine bone matrix is prepared by previously published procedures (Sampath and Reddi (1983) Proc. Natl. Acad. Sci. USA 80: 6591-6595). Bovine diaphyseal bones (age 1-10 days) are obtained from a local slaughterhouse and used fresh. The bones are stripped of muscle and fat, cleaned of periosteum, demarrowed by pressure with cold water, dipped in cold absolute ethanol, and stored at −20° C. They are then dried and fragmented by crushing and pulverized in a large mill. Care is taken to prevent heating by using liquid nitrogen. The pulverized bone is milled to a particle size between 70-420 mm and is defatted by two washes of approximately two hours duration with three volumes of chloroform and methanol (3:1). The particulate bone is then washed with one volume of absolute ethanol and dried over one volume of anhydrous ether. The defatted bone powder (the alternative method is to obtain Bovine Cortical Bone Powder (75-425 mm) from American Biomaterials) is then demineralized with 10 volumes of 0.5 N HCl at 4° C. for 40 min., four times. Finally, neutralizing washes are done on the demineralized bone powder with a large volume of water.

A2. Dissociative Extraction and Ethanol Precipitation

Demineralized bone matrix thus prepared is dissociatively extracted with 5 volumes of 4 M guanidine-HCl, 50M Tris-HCl, pH 7.0, containing protease inhibitors (5 mM benzamidine, 44 mM 6-aminohexanoic acid, 4.3 mM N-ethylmaleimide, 0.44 mM phenylmethylsulfonyfluoride) for 16 hr. at 4° C. The suspension is filtered. The supernatant is collected and concentrated to one volume using an ultrafiltration hollow fiber membrane (Amicon, YM-10). The concentrate is centrifuged (8,000×g for 10 min. at 4° C.), and the supernatant is then subjected to ethanol precipitation. To one volume of concentrate is added five volumes of cold (−70° C.) absolute ethanol (100%), which is then kept at −70° C. for 16 hrs. The precipitate is obtained upon centrifugation at 10,000×9 for 10 min. at 4° C. The resulting pellet is resuspended in 4 l of 85% cold ethanol incubated for 60 min. at −70° C. and recentrifuged. The precipitate is again resuspended in 85% cold ethanol (2 l), incubated at −70° C. for 60 min. and centrifuged. The precipitate is then lyophilized.

A3. Heparin-Sepharose Chromatography I

The ethanol precipitated, lyophilized, extracted crude protein is dissolved in 25 volumes of 6 M urea, 50 mM Tris-HCl, pH 7.0 (Buffer A) containing 0.15 M lacI, and clarified by centrifugation at 8,000×g for 10 min. The heparin-Sepharose is column-equilibrated with Buffer A. The protein is loaded onto the column and after washing with three column volume of initial buffer (Buffer A containing 0.15 M HaCl), protein is eluted with Buffer A containing 0.5 M NaCl. The absorption of the eluate is monitored continuously at 280 nm. The pool of protein eluted by 0.5 M NaCl (approximately 1 column volumes) is collected and stored at 4° C.

As shown in FIG. 2A, most of the protein (about 95%) remains unbound. Approximately 5% of the protein is bound to the column. The unbound fraction has no bone inductive activity when bioassayed as a whole or after a partial purification through Sepharose CL-6B.

A4. Hydroxyapaptite-Ultrogel Chromatography

Figure 2B:
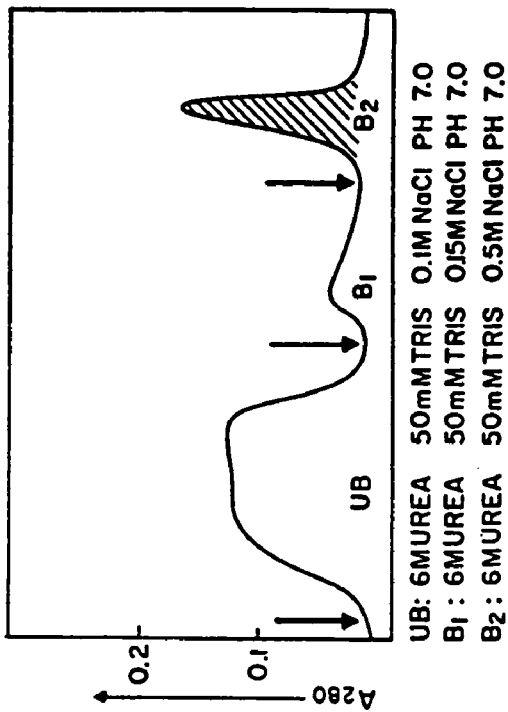

The volume of protein eluted by Buffer A containing 0.5 M NaCl from the heparin-Sepharose is applied directly to a column of hydroxyapaptite-ultrogel (HAP-ultrogel) (LKB Instruments), equilibrated with Buffer A containing 0.5 M NaCl. The HAP-ultrogel is treated with Buffer A containing 500 mM Na phosphate prior to equilibration. The unadsorbed protein is collected as an unbound fraction, and the column is washed with three column volumes of Buffer A containing 0.5H NaCl. The column is subsequently eluted with Buffer A containing 100 mM Na Phosphate (FIG. 2B).

The eluted component can induce endochondral bone as measured by alkaline phosphatase activity and histology. As the biologically active protein is bound to HAP in the presence of 6 M urea and 0.5 MN NaCl, it is likely that the protein has an affinity for bone mineral and may be displaced only by phosphate ions.

A5. Sephacryl S-300 Gel Exclusion Chromatography

Figure 2C:
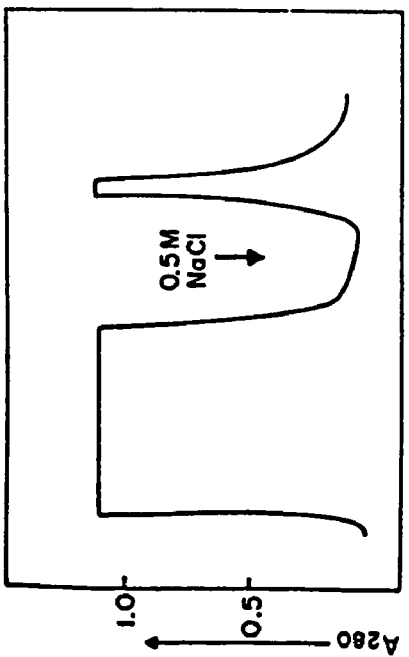

Sephacryl S-300 HR (High Resolution, 5 cm×100 cm column) is obtained from Pharmacia and equilibrated with 4 M guanidine-HCl, 50 mM Tris-HCl, pH 7.0. The bound protein fraction from HA-ultrogel is concentrated and exchanged from urea to 4 M guanidine-HCl, 50M Tris-HCl, pH 7.0 via an Amicon ultrafiltration YM-10 membrane. The solution is then filtered with Schleicher and Schuell CENTREX disposable microfilters. A sample aliquot of approximately 15 ml containing approximately 400 mg of protein is loaded onto the column and then eluted with 4 M guanidine-HCl, 50 mM Tris-HCl, pH 7.0, with a flow rate of 3 ml/min; 12 ml fractions are collected over 8 hours and the concentration of protein is measured at $A_{280}$ nm (FIG. 2C). An aliquot of the individual fractions is bioassayed for bone formation. Those fractions which have shown bone formation and have a molecular weigh less than 35 kD are pooled and concentrated via an Amicon ultrafiltration system with YM-10 membrane.

A6. Heparin-Sepharose Chromatography-II

Figure 2D:
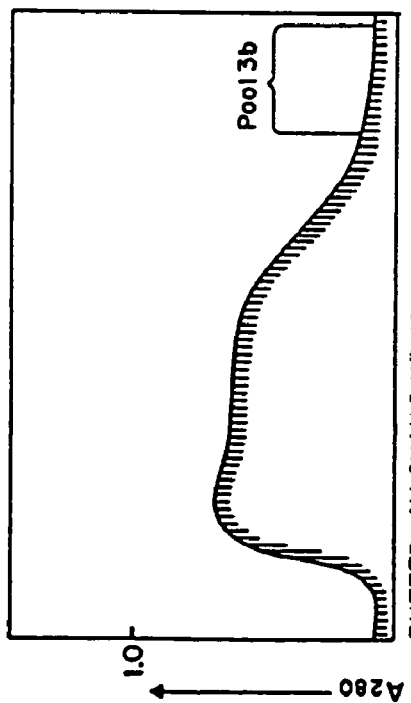

The pooled osteo-inductive fractions obtained from gel exclusion chromatography are dialysed extensively against distilled water and then against 6 M urea, 50 mM Tris-HCl, pH 7.0 (Buffer A) containing 0.1 M NaCl. The dialysate is then cleared through centrifugation. The sample is applied to the heparin-sepharose column (equilibrated with the same buffer). After washing with three column volumes of initial buffer, the column is developed sequentially with Buffer B containing 0.15 M MaCl, and 0.5 N NaCl (FIG. 2D). The protein eluted by 0.5 M NaCl is collected and dialyzed extensively against distilled water. It is then dialyzed against 30% acetonitrile, 0.1% TFA at 4° C.

A7. Reverse Phase HPLC

Figure 8:
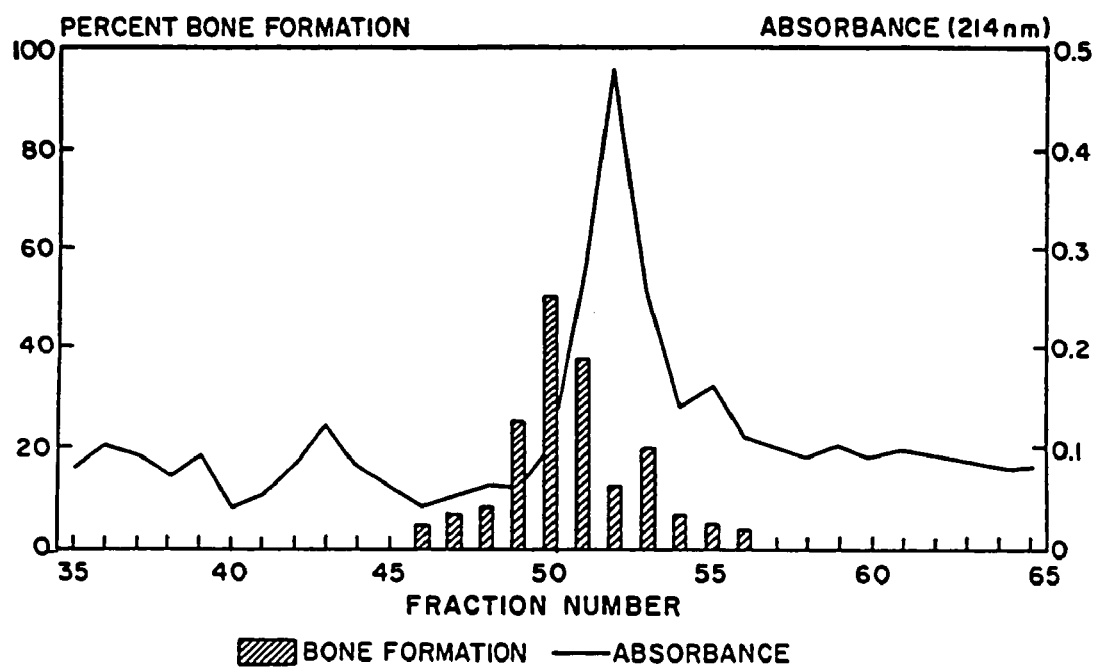
FIG. 8 is an HPLC chromatogram of an elution profile on reverse phase C-18 HPLC of the samples recovered from the second heparin-Sepharose chromatography step (see FIG. 2D). Superimposed is the percent bone formation in each fraction.

The protein is further purified by C-18 Vydac silica-based HPLC column chromatography (particle size 5 mm; pore size 300 A). The osteoinductive fraction obtained from heparin-sepharose-II chromatograph is loaded onto the column, and washed in 0.1% TFA, 10% acetonitrile for five min. As shown in FIG. 8, the bound proteins are eluted with a linear gradient of 10-30% acetonitrile over 15 min., 30-50% acetonitrile over 60 min, and 50-70% acetonitrile over 10 min at 22° C. with a flow rate of 1.5 ml/min and 1.4 ml samples are collected in polycarbonate tubes. Protein is monitored by absorbance at $A_{214}$ nm. Column fractions are tested for the presence of osteoinductive activity, concanavalin A-blottable proteins and then pooled. Pools are then characterized biochemically for the presence of 30 kD protein by autoradiography, concanavalin A blotting, and Coomassie blue dye staining. They are then assayed for in vivo osteogenic activity. Biological activity is not found in the absence of 30 kD protein.

A8. Gel Elution

The glycosylated or deglycosylated protein is eluted from SDS gels (0.5 mm and 1.5 mm thickness) for further characterization. $^{125}$I-labelled 30 kD protein is routinely added to each preparation to monitor yields. TABLE 1 shows the various elution buffers that have been tested and the yields of $^{125}$I-labelled protein.

TABLE 1

Elution of 30 kD Protein from SDS Gel

| | Buffer | % Eluted | |
|---|---|---|---|
| | | 0.5 mm | 1.5 mm |
| (1) | $dH_2O$ | 22 | |
| (2) | 4M Guanidine-HCl, Tris-HCl, pH 7.0 | 2 | |
| (3) | 4M Guanidine-HCl, Tris-HCl, pH 7.0, 0.5% Triton x 100 | 93 | 52 |
| (4) | 0.1% SDS, Tris-HCl, pH 7.0 | 98 | |

TABLE 2 lists the steps used to isolate the 30 kD or deglycosylated 27 kD gel-bound protein. The standard protocol uses diffusion elution using 4M guanidine-HCl containing 0.5% Triton x 100 in Tris-HCl buffer or in Tris-HCl buffer containing 0.1% SDS to achieve greater than 95% elution of the protein from the 27 or 30 kD region of the gel for demonstration of osteogenic activity in vivo as described in later section.

In order to isolate substantially purified 30 kD or deglycosylated 27 kD protein for sequencing and characterization, the following steps are mentioned in Table 2.

TABLE 2

Preparation of Gel Eluted Protein
(C-18 Pool or deglycoslated protein plus
$^{125}$I-labelled 30 kD protein)

| | |
|---|---|
| 1. | Dry using vacuum centrifugation; |
| 2. | Wash pellet with $H_2O$; |
| 3. | Dissolve pellet in gel sample buffer (no reducing agent); |
| 4. | Electrophorese on pre-electrophoresed 0.5 mm mini gel; |
| 5. | Cut out 27 or 30 kD protein; |
| 6. | Elute from gel with 0.1% SDS, 50 mM Tris-HCl, pH 7.0; |
| 7. | Filter through Centrex membrane; |
| 8. | Concentrate in Centricon tube (10 kD membrane); |
| 9. | Chromatograph of TSK-3000 gel filtration column; |
| 10. | Concentrate in Centricon tube. |

Chromatography in 0.1% SDS on a TSK-3000 gel filtration column is performed to separate gel impurities, such as soluble acrylamide, from the final product. The overall yield of labelled 30 kD protein from the gel elution protocol is 50-60% of the loaded sample. Most of the loss occurs in the electrophoresis step, due to protein aggregation and/or smearing. In a separate experiment, a sample of gel eluted 30 kD protein is reduced, electrophoresed on an SDS gel, and transferred to an Immobilon membrane. The membrane is stained with Coomassie blue dye, cut into slices, and the slices are counted. Coomassie blue dye stains the 16 kD and 18 kD reduced species of the 30 kD protein almost exclusively. However, the counts showed significant smearing throughout the gel in addition to being concentrated in the 16 kD and 18 kD species. This suggests that the $^{125}$I-label can exhibit anomolous behavior on SDS gels and cannot be used as an accurate marker for cold protein under such circumstances.

The yield is 0.5 to 1.0 mg substantially pure osteogenic protein per kg of bone.

A9. Isolation of the 16 kD and 18 kD Species

TABLE 3 summarizes the procedures involved in the preparation of the subunits. Approximately 10 mg of gel eluted 30 kD protein (FIG. 3) is carboxymethylated and electrophoresed on an SDS-gel.

Figure 15:
FIG. 15 is a photographic representation of a Coomassie blue stained SDS gel showing gel purified subunits of the 30 kD protein.

The sample contains $^{125}$I-label to trace yields and to use as an indicator for slicing the 16 kD, IS kD and non-reduceable 30 K regions from the gel. FIG. 15 shows a Coomassie stained gel of aliquots of the protein isolated from the different gel slices. The slices corresponding to the 16 kD, 18 kD and non-reduceable 30 kD species contained approximately 2-3 mg, 3-4 mg, and 1-2 mg, of protein respectively, as estimated by staining intensity.

Prior to SDS electrophoresis, all of the 30 kD species can be reduced to the 16 kD and 18 kID species. The nonreducible 30 kD species observed after electrophoresis appears to be an artifact resulting from the electrophoresis procedure.

TABLE 3

Isolation of the Subunits of the 30 kD protein
(C-18 pool plus $^{125}$I labeled 30 kD protein)

| | |
|---|---|
| 1. | Electrophorese on SDS gel. |
| 2. | Cut out 30 kD protein. |
| 3. | Elute with 0.1% SDS, 50 nm Tris, pH 7.0. |
| 4. | Concentrate and wash with H$_2$O in Centricon tube (10 kD membranes). |
| 5. | Reduce and carboxymethylate in 1% SDS, 0.4 M Tris, pH 8.5. |
| 6. | Concentrate and wash with H$_2$O in Centricon tube. |
| 7. | Electrophorese on SDS gel. |
| 8. | Cut out the 16 kD and 18 kD subunits. |
| 9. | Elute with 0.1% SDS, 50 mM Tris, pH 7.0. |
| 10. | Concentrate and wash with H$_2$O in Centricon tubes. |

B. Demonstration that the 30 KD Protein is Osteogenic Protein—Biological Characterization B1. Gel Slicing:

Gel slicing experiments confirm that the isolated 30 kD protein is the protein responsible for osteogenic activity.

Gels from the last step of the purification are sliced. Protein in each fraction is extracted in 15 mM Tris-HCl, pH 7.0 containing 0.1% SDS or in buffer containing 4M guanidine-HCl, 0.5% non-ionic detergent (Triton x 100), 50 mM Tris-HCl. The extracted proteins are desalted, concentrated, and assayed for endochondral bone formation activity. The results are set forth in FIG. 14. From this Figure it is clear that the majority of osteogenic activity is due to protein at 30 kD region of the gene. Activity in higher molecular weight regions is apparently due to protein aggregation. These protein aggregates, when reduced, yields the 16 kD and 18 kD species discussed above.

B2. Con A-Sepharose Chromatography:

A sample containing the 30 kD protein is solubilized using 0.1% SDS, 50 mM Tris-HCl, and is applied to a column of Con A-Sepharose equilibrated with the same buffer. The bound material is eluted in SDS Tris-HCl buffer containing 0.5 M alpha-methyl mannoside. After reverse phase chromatography of both the bound and unbound fractions, Con A-bound materials, when implanted, result in extensive bone formation. Further characterization of the bound materials show a Con A-blottable 30 kD protein. Accordingly, the 30 kD glycosylated protein is responsible for the bone forming activity.

Figure 9:
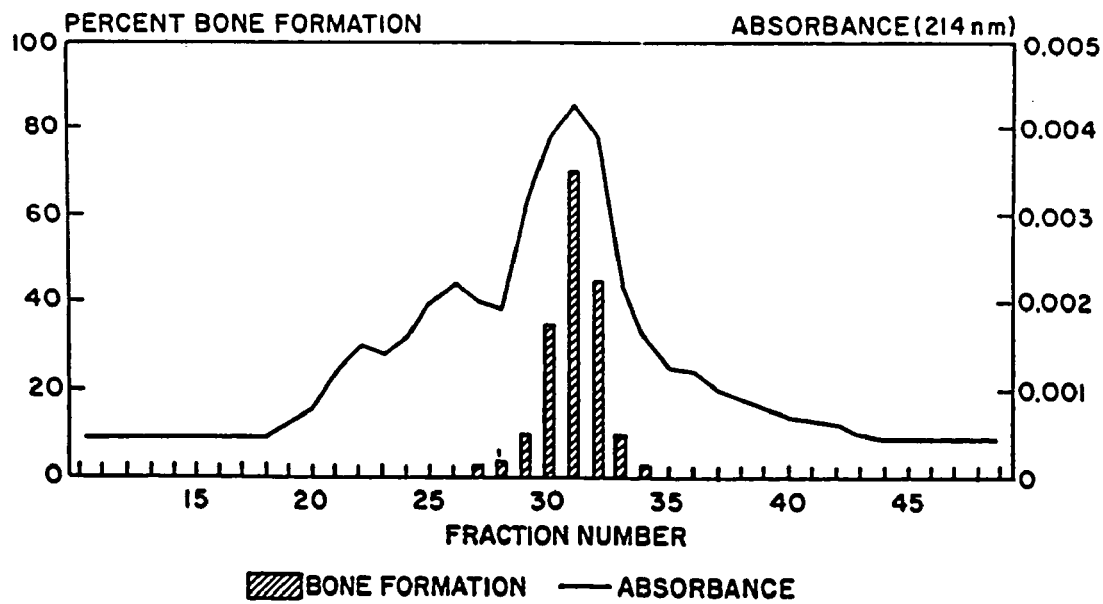
FIG. 9 is a gel permeation chromatogram of an elution profile on TSK 3000/2000 gel of the C-18 purified osteogenic peak fraction. Superimposed is the percent bone formation in each fraction.

B3. Gel Permeation Chromatography:

TSK-3000/2000 gel permeation chromatography in guanidine-HCl alternately is used to achieve separation of the high specific activity fraction obtained from C-18 chromatography (FIG. 9). The results demonstrate that the peak of bone inducing activity elutes in fractions containing substantially pure 30 kD protein by Coomassie blue staining. When this fraction is iodinated and subjected to autoradiography, a strong band at 30 kD accounts for 90% of the iodinated proteins. The fraction induces bone formation in vivo at a dose of 50 to 100 ng per implant.

B4. Structural Requirements for Biological Activity

Although the role of 30 kD osteogenic protein is clearly established for bone induction, through analysis of proteolytic cleavage products we have begun to search for a minimum structure that is necessary for activity in vivo. The results of cleavage experiments demonstrate that pepsin treatment fails to destroy bone inducing capacity, whereas trypsin or CNBr completely abolishes the activity.

An experiment is performed to isolate and identify pepsin digested product responsible for biological activity. Sample used for pepsin digest were 20%-30% pure. The buffer used is 0.1 TFA in water. The enzyme to substrate ratio is 1:10. A control sample is made without enzyme. The digestion mixture is incubated at room temperature for 16 hr. The digested product is then separated in 4 M guanidine-HCl using gel permeation chromatography, and the fractions are prepared for in vivo assay. The results demonstrate that active fractions from gel permeation chromatography of the pepsin digest correspond to molecular weight of 8 kD-10 kD.

Figure 17A:
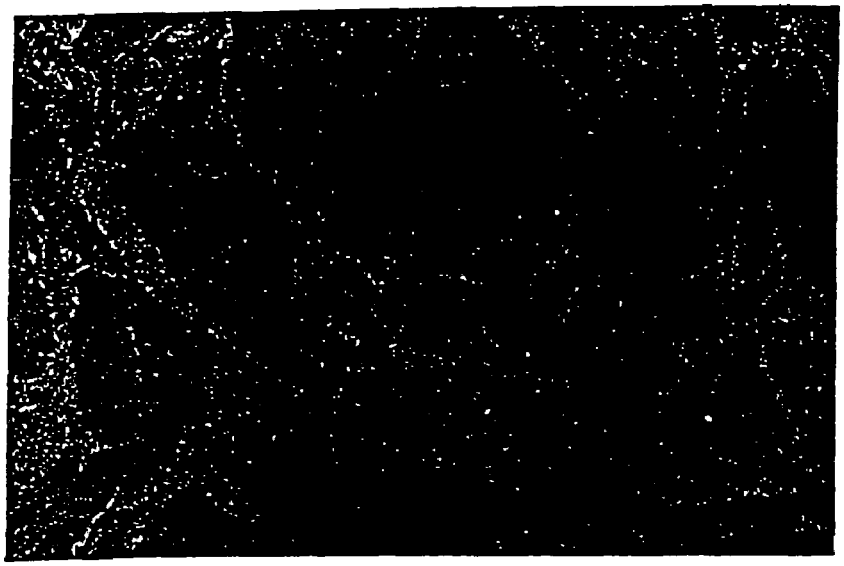
FIG. 17 is a photographic representation of the histological examination of bone implants in the rat model: carrier alone (A); carrier and glycosylated osteogenic protein (B); and carrier and deglycosylated osteogenic protein (C). Arrows indicate osteoblasts.
Figure 17B:
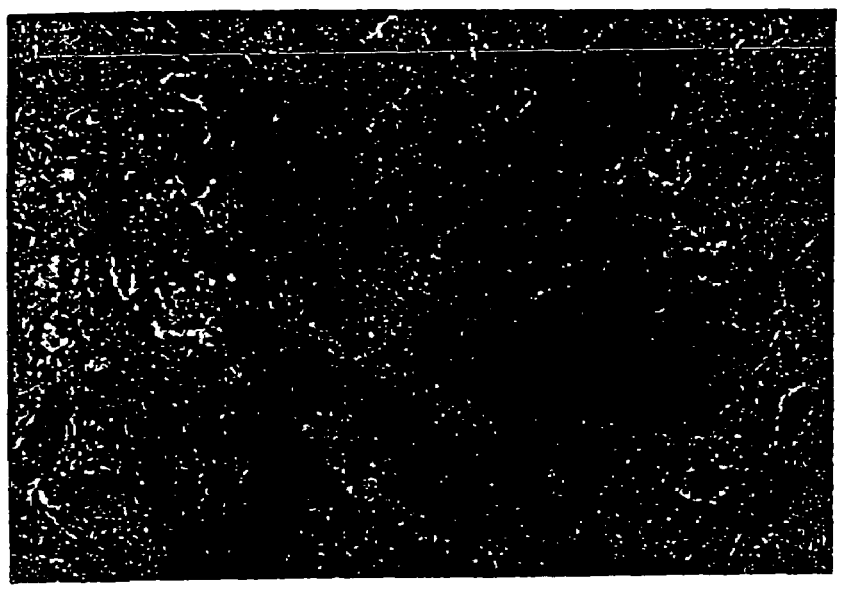
Figure 17C:
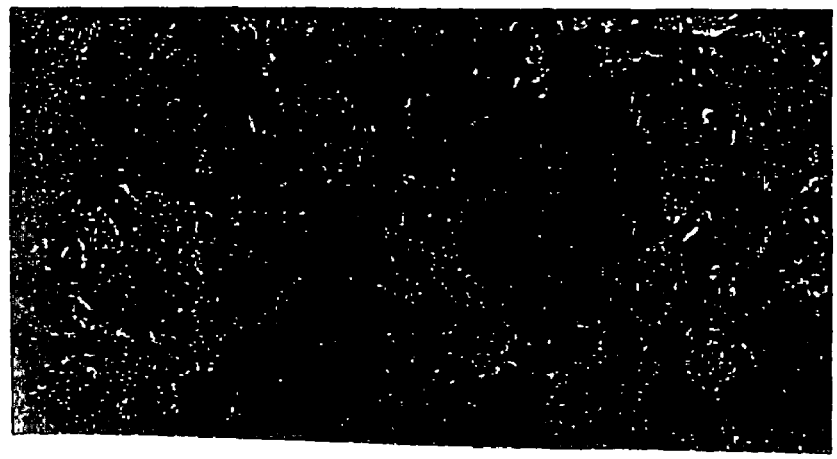

In order to understand the importance of the carbohydrates moiety with respect to osteogenic activity, the 30 kD protein has been chemically deglycosylated using HF (see below). After analyzing an aliquot of the reaction product by Con A blot to confirm the absence of carbohydrate, the material is assayed for its activity in vivo. The bioassay is positive (i.e., the deglycosylated protein produces a bone formation response as determined by histological examination shown in FIG. 17C), demonstrating that exposure to HF did not destroy the biological function of the protein. In addition, the specific activity of the deglycosylated protein is approximately the same as that of the native glycosylated protein.

B5. Specific Activity of BOP

Experiments were performed 1) to determine the half maximal bone-inducing activity based on calcium content of the implant; 2) to estimate proteins at nanogram levels using a gel scanning method; and 3) to establish dose for half maximal bone inducing activity for gel eluted 30 kD BOP.

The results demonstrate that gel eluted substantially pure 30 kD osteogenic protein induces bone at less than 5 ng per 25 mg implant and exhibits half maximal bone differentiation activity at 20 ng per implant. The purification data suggest that osteogenic protein has been purified from bovine bone to 367,307 fold after final gel elution step with a specific activity of 47,750 bone forming units per mg of protein.

B5(a)Half Maximal Bone Differentiation Activity

The bone inducing activity is determined biochemically by the specific activity of alkaline phosphatase and calcium content of the day 12 implant. An increase in the specific activity of alkaline phosphatase indicates the onset of bone formation. Calcium content, on the other hand, is proportional to the amount of bone formed in the implant. The bone formation is therefore calculated by determining calcium content of the implant on day 12 in rats and expressed as bone forming units, which represent the amount that exhibits half maximal bone inducing activity compared to rat demineralized bone matrix. Bone induction exhibited by intact demineralized rat bone matrix is considered to be the maximal bone-differentiation activity for comparison.

B5(b)Protein Estimation Using Gel Scanning Techniques

A standard curve is developed employing known amounts of a standard protein, bovine serum albumin. The protein at varying concentration (50-300 ng) is loaded on 15% SDS gel, electrophoresed, stained in comassie and destained. The gel containing standard proteins is scanned at predetermined settings using a gel scanner at 580 nm. The area covered by the protein band is calculated and a standard curve against concentrations of protein is constructed. A sample with an unknown protein concentration is electrophoresed with known concentration of BSA. The lane contained unknown sample is scanned and from the area the concentration of protein is determined.

B5(c)Gel Elution and Specific Activity

Figure 14:
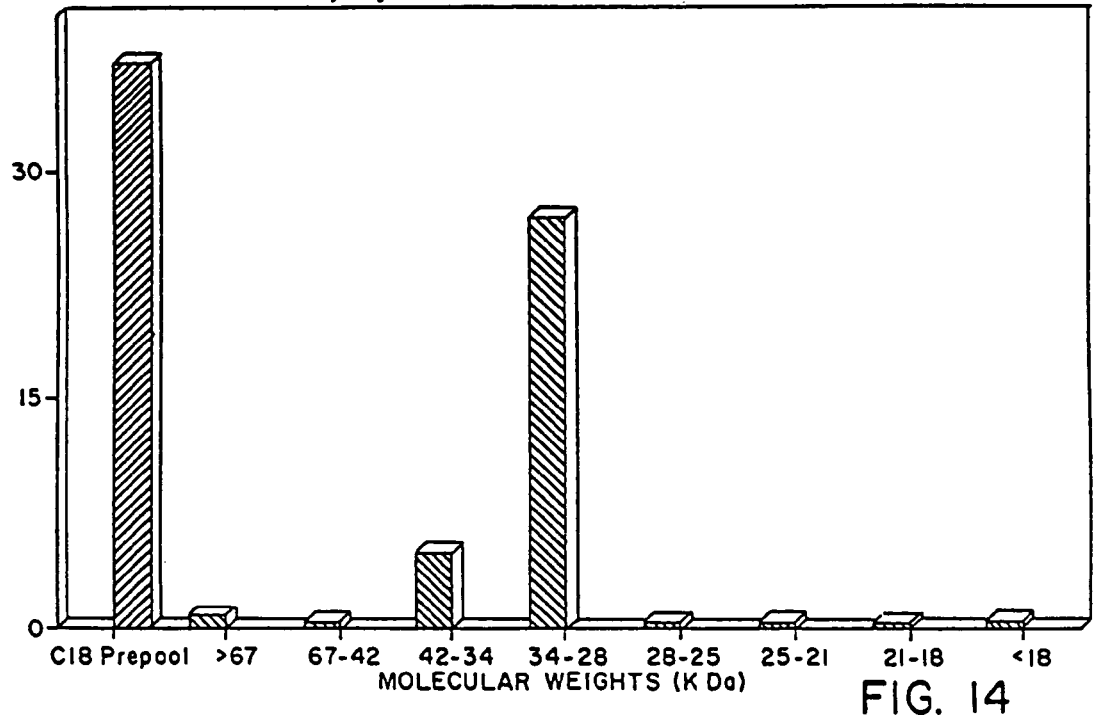
FIG. 14 is a graph of osteogenic activity vs. Increasing molecular weight showing peak bone forming activity in the 30 kD region of an SDS polyacrylamide gel.

An aliquot of C-18 highly purified active fraction is subjected to SDS gel and sliced according to molecular weights described in FIG. 14. Proteins are eluted from the slices in 4 M guanidine-HCl containing 0.5% Triton X-100, desalted, concentrated and assayed for endochondral bone forming activity as determined by calcium content. The C-18 highly active fractions and gel eluted substantially pure 30 kD osteogenic protein are implanted in varying concentrations in order to determine the half maximal bone inducing activity.

Figure 20A:
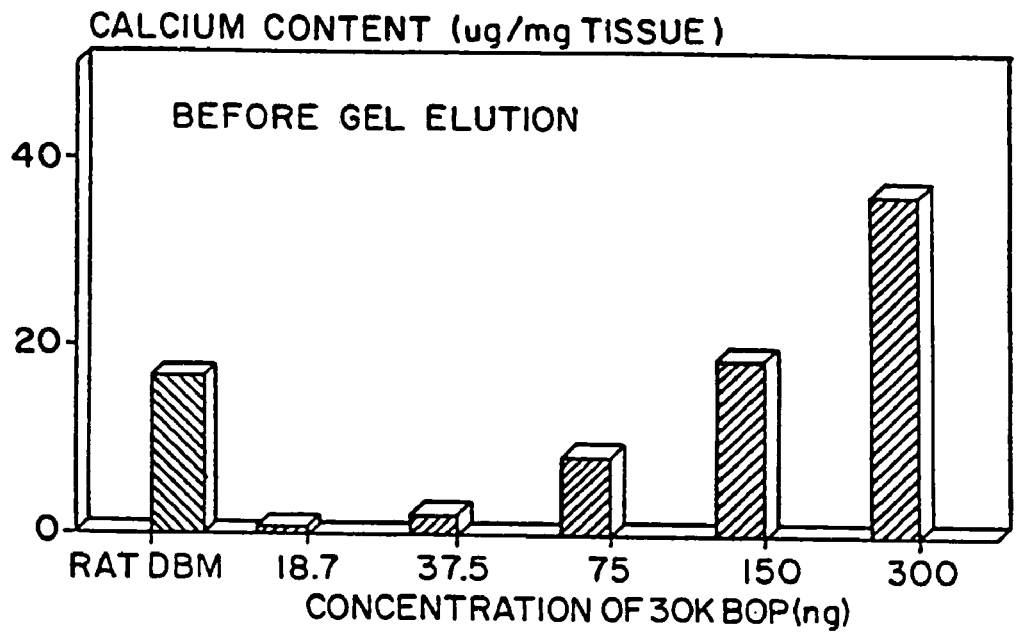
FIGS. 20A and 20B are bar graphs showing the specific activity of naturally sourced OP before and after gel elution as measured by calcium content vs. increasing concentrations of proteins (dose curve, in ng)
Figure 20B:
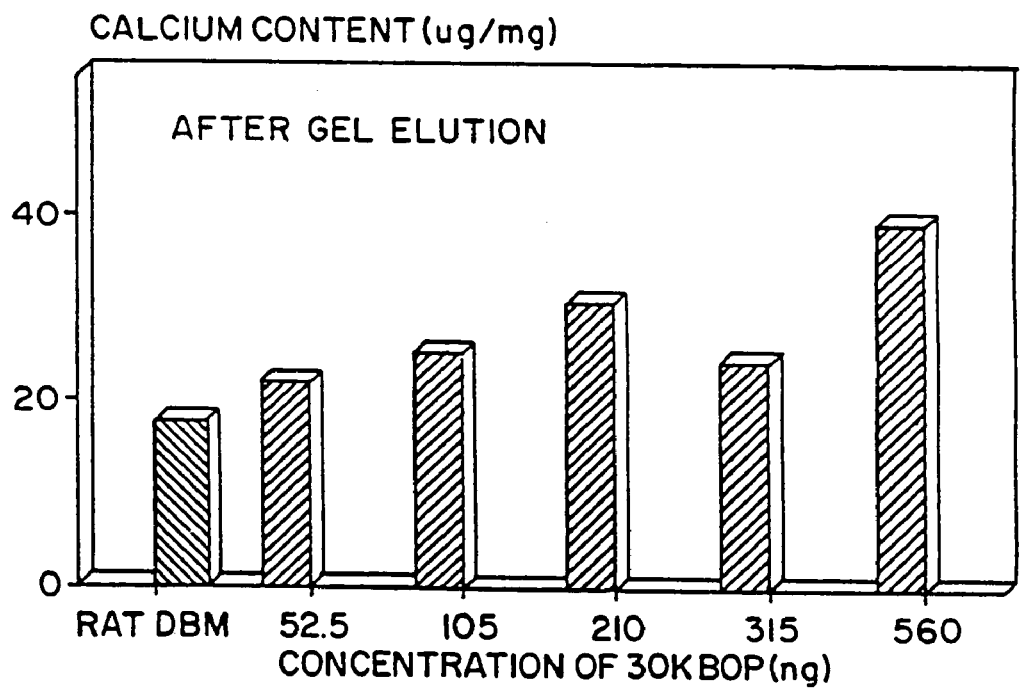

FIG. 14 demonstrates that the bone inducing activity is due to proteins eluted at 28-34 kD region. The recovery of activity after gel elution step is determined by calcium content. FIGS. 20A and 20B represent the bone inducing activity for the various concentrations of 30 kD protein before and after gel elution as estimated by calcium content. The concentration of protein is determined by gel scanning in the 30 kD region. The data suggest that the half maximal activity for 30 kD protein before gel elution is 69 nanogram per 25 mg implant and is 21 nanogram per 25 mg implant after elution. Table 4 describes the yield, total specific activity, and fold purification of osteogenic protein at each step during purification. Approximately 500 ug of heparin sepharose I fraction, 130-150 ug of the HA ultrogel fraction, 10-12 ug of the gel filtration fraction, 4-5 ug of the heparin sepharose II fraction, 0.4-0.5 ug of the C-18 highly purified fraction, and 20-25 ng of gel eluted substantially purified is needed per 25 mg of implant for unequivocal bone formation for half maximal activity. Thus, 0.8-1.0 ng purified osteogenic protein per mg. of implant is required to exhibit half maximal bone differentiation activity in vivo.

TABLE 4

PURIFICATION OF BOP

| Purification Steps | Protein (mg.) | Biological Activity Units* | Specific Activity Units/mg. | Purification Fold |
|---|---|---|---|---|
| Ethanol Precipitate** | 30,000# | 4,000 | 0.13 | 1 |
| Heparin Sepharose I | 1,200# | 2,400 | 2.00 | 15 |
| HA-Ultrogel | 300# | 2,307 | 7.69 | 59 |
| Gel filtration | 20# | 1,600 | 80.00 | 615 |
| Heparin Sepharose II | 5# | 1,000 | 200.00 | 1,538 |
| C-18 HPLC | 0.070@ | 150 | 2,043.00 | 15,715 |
| Gel elution | 0.004@ | 191 | 47,750.00 | 367,307 |

Values are calculated from 4 kg. of bovine bone matrix (800 g of demineralized matrix).
*One unit of bone forming activity is defined as the amount that exhibits half maximal bone differentiation activity compared to rat demineralized bone matrix, as determined by calcium content of the implant on day 12 in rats.
Proteins were measured by absorbance at 280 nm.
@Proteins were measured by gel scanning method compared to known standard protein, bovine serum albumin.
**Ethanol-precipitated guanidine extract of bovine bone is a weak inducer of bone in rats, possibly due to endogenous inhibitors. This precipitate is subjected to gel filtration and proteins less than 50 kD were separated and used for bioassay.

C. Chemical Characterization of BOP

C1. Molecular Weight and structure

Electrophoresis of the most active fractions from reverse phase C-18 chromatography on non-reducing SDS polyacrylamide gels reveals a single band at about 30 kD as detected by both Coomassie blue staining (FIG. 3A) and autoradiography.

In order to extend the analysis of BOP, the protein was examined under reducing conditions. FIG. 3B shows an SDS gel of BOP in the presence of dithiothreitol. Upon reduction, 30 kD BOP yields two species which are stained with Coomassic blue dye: a 16 kD species and an 18 kD species. Reduction causes loss of biological activity. Methods fot the efficient elution of the proteins from SDS gels have been tested, and a protocol has been developed to achieve purification of both proteins. The two reduced BOP species have been analyzed to determine if they are structurally related. Comparison of the amino acid composition of the two proteins (as disclosed below) shows little differences, indicating that the native protein may comprise two chains having some homology.

C2. Charge Determination

Isoelectric focusing studies are initiated to further evaluate the 30 kD protein for possible heterogeneity. Results to date have not revealed any such heterogeneity. The oxidized and reduced species migrate as diffuse bands in the basic region of the isoelectric focusing gel, using the iodinated 30 kD protein for detection. Using two dimensional gel electrophoresis and Con A for detection, the oxidized 30 kD protein show one species migrating in the same basic region as the iodinated 30 kD protein. The diffuse character of the band may be traced to the presence of carbohydrate attached to the protein.

C3. Presence of Carbohydrate

The 30 kD protein has been tested for the presence of carbohydrate by Concanavalin A (Con A) blotting after SDS-PAGE and transfer to nitrocellulose paper. The results demonstrate that the 30 kD protein has a high affinity for Con A, indicating that the protein is glycosylated (FIG. 4A). In addition, the Con A blots provide evidence for a substructure in the 30 kD region of the gel, suggesting heterogeneity due to varying degrees of glycosylation. After reduction (FIG. 4B), Con A blots show evidence for two major components at 16 kD and 18 kD. In addition, it has been demonstrated that no glycosylated material remains at the 30 kD region after reduction.

In order to confirm the presence of carbohydrate and to estimate the amount of carbohydrate attached, the 30 kD protein is treated with N-glycanase, a deglycosylating enzyme with a broad specificity. Samples of the $^{125}$I-labelled 30 kD protein are incubated with the enzyme in the presence of SDS for 24 hours at 37° C. As observed by SDS-PAGE, the treated samples appear as a prominent species at about 27 kD (FIG. 5A). Upon reduction, the 27 kD species is reduced to species having a molecular weight of about 14 kD-16 kD (FIG. 5B).

Chemical cleavage of the carbohydrate moieties using hydrogen fluoride (HP) is performed to assess the role of carbohydrate on the bone inducing activity of BOP in vivo. Active osteogenic protein fractions pooled from the C-18 chromatography step are dried in vacuo over $P_2O_5$ in a polypropylene tube, and 50 ml freshly distilled anhydrous HF at –70° C. is added. After capping the tube tightly, the mixture is kept at 0° C. in an ice-bath with occasional agitation for 1 hr. The HF is then evaporated using a continuous stream of dry nitrogen gas. The tube is removed from the ice bath and the residue dried in vacuo over $P_2O_5$ and KOH pellets.

Following drying, the samples are dissolved in 100 ml of 50% acetonitrile/0.1% TFA and aliquoted for SDS gel analysis, Con A binding, and biological assay. Aliquots are dried and dissolved in either SDS gel sample buffer in preparation for SDS gel analysis and Con A blotting or 4 M guanidine-HCl, 50 mM Tris-HCl, pH 7.0 for biological assay.

The results show that samples are completely deglycosylated by the HF treatment: Con A blots after SDS gel electrophoreses and transfer to Immobilon membrane showed no binding of Con A to the treated samples, while untreated controls were strongly positive at 30 kD. Coomassie gels of treated samples showed the presense of a 27 kD band instead of the 30 kD band present in the untreated controls.

C4. Chemical and Enzymatic Cleavage

Cleavage reactions with CNBr are analyzed using Con A binding for detection of fragments associated with carbohydrate. Cleavage reactions are conducted using trifluoroacetic acid (TFA) in the presence and absence of CNBr. Reactions are conducted at 37° C. for 18 hours, and the samples are vacuum dried. The samples are washed with water, dissolved in SDS gel sample buffer with reducing agent, boiled and applied to an SDS gel. After electrophoresis, the protein is transferred to Immobilon membrane and visualized by Con A binding. In low concentrations of acid (1%), CNBr cleaves the majority of 16 kD and 18 kD species to one product, a species about 14 kD. In reactions using 10% TFA, a 14 kD species is observed both with and without CNBr.

Figure 6:
FIG. 6 is a photographic reproduction of an autoradiogram of an SDS polyacrylamide gel of peptides produced upon the digestion of the 30 kD osteogenic protein with V-8 protease (B), Endo Lys C protease (C), pepsin (D), and trypsin (E). (A) is control.

Four proteolytic enzymes are used in these experiments to examine the digestion products of the kD protein: 1) V-8 protease; 2) Endo Lys C protease; 3) pepsin; and 4) trypsin. Except for pepsin, the digestion buffer for the enzymes is 0.1 M ammonium bicarbonate, pH 8.3. The pepsin reactions are done in 0.1% TFA. The digestion volume is 100 ml and the ratio of enzyme to substrate is 1:10. $^{125}$I-labelled 30 kD osteogenic protein is added for detection. After incubation at 37° C. for 16 hr., digestion mixtures are dried down and taken up in gel sample buffer containing dithiothreitol for SDS-PAGE. FIG. 6 shows an autoradiograph of an SDS gel of the digestion products. The results show that under these conditions, only trypsin digests the reduced 16 kD/18 kD species completely and yields a major species at around 12 kD. Pepsin digestion yields better defined, lower molecular weight species. However, the 16 kD/18 kD fragments were not digested completely. The V-8 digest shows limited digestion with one dominant species at 16 kD.

C5. Protein Sequencing

Figure 7A:
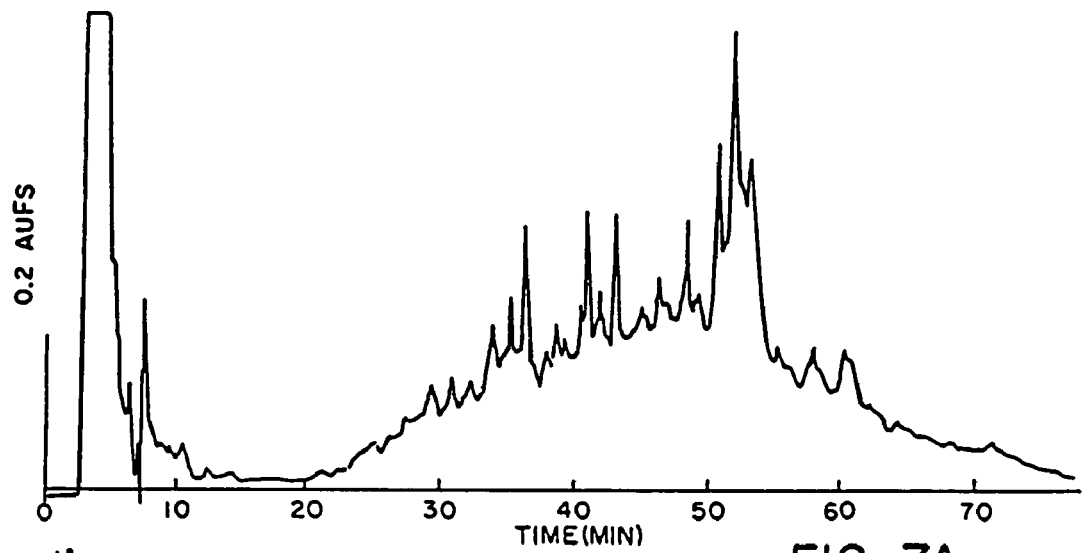
FIG. 7 is a collection of HPLC chromatograms of tryptic peptide digestions of 30 kD BOP (A), the 16 kD subunit (B), and the 18 kD subunit (C)

To obtain amino acid sequence data, the protein is cleaved with trypsin or Endoproteinase Asp-N (EndoAsp-N). The tryptic digest of reduced and carboxymethylated 30 kD protein (approximately 10 mg) is fractionated by reverse-phase HPLC using a C-8 narrowbore column (13 cm×2.1 mm ID) with a TFA/acetonitrile gradient and a flow rate of 150 ml/min. The gradient employs (A) 0.06% TFA in water and (B) 0.04% TFA in water and acetonitrile (1:4; v:v). The procedure was 10% B for five min., followed by a linear gradient for 70 min. to 80% B, followed by a linear gradient for 10 min. to 100% B. Fractions containing fragments as determined from the peaks in the HPLC profile (FIG. 7A) are rechromatographed at least once under the same conditions in order to isolate single components satisfactory for sequence analysis.

Figure 7B:
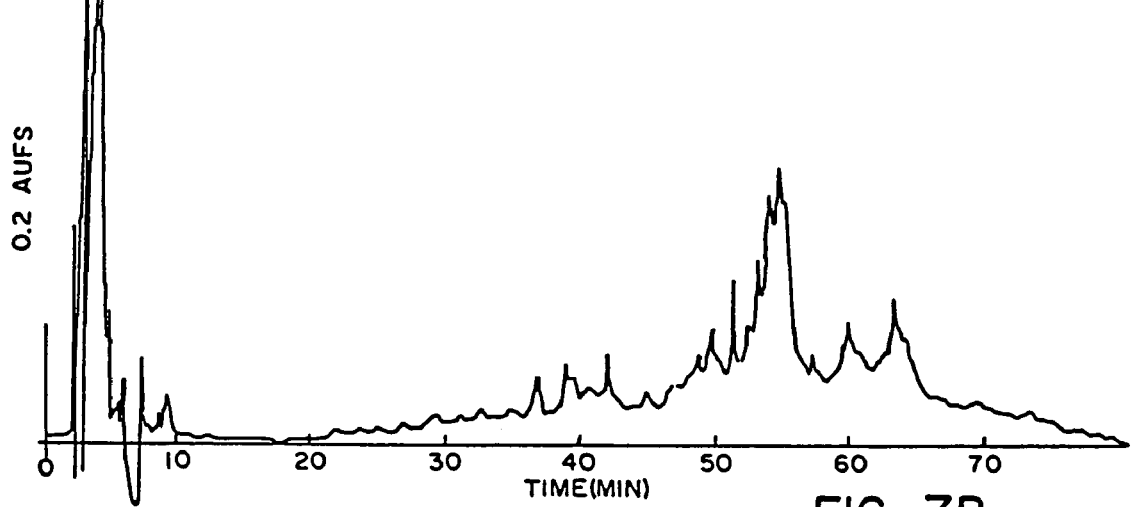
Figure 7C:
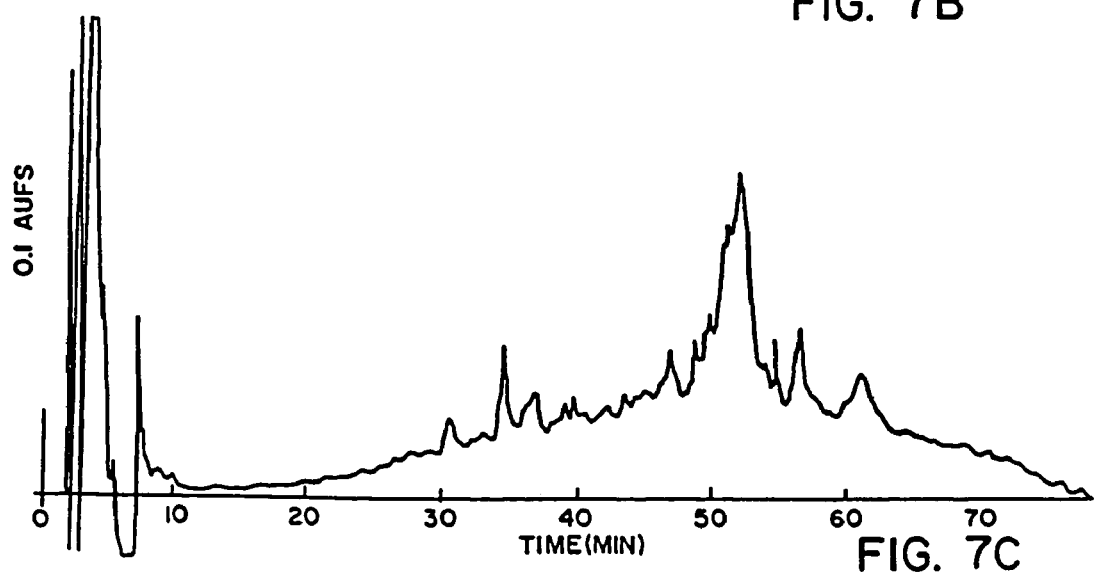

The HPLC profiles of the similarly digested 16 kD and 18 kD subunits are shown in FIGS. 7B and 7C, respectively. These peptide maps are similar suggesting that the subunits are identical or are closely related.

Figure 16A:
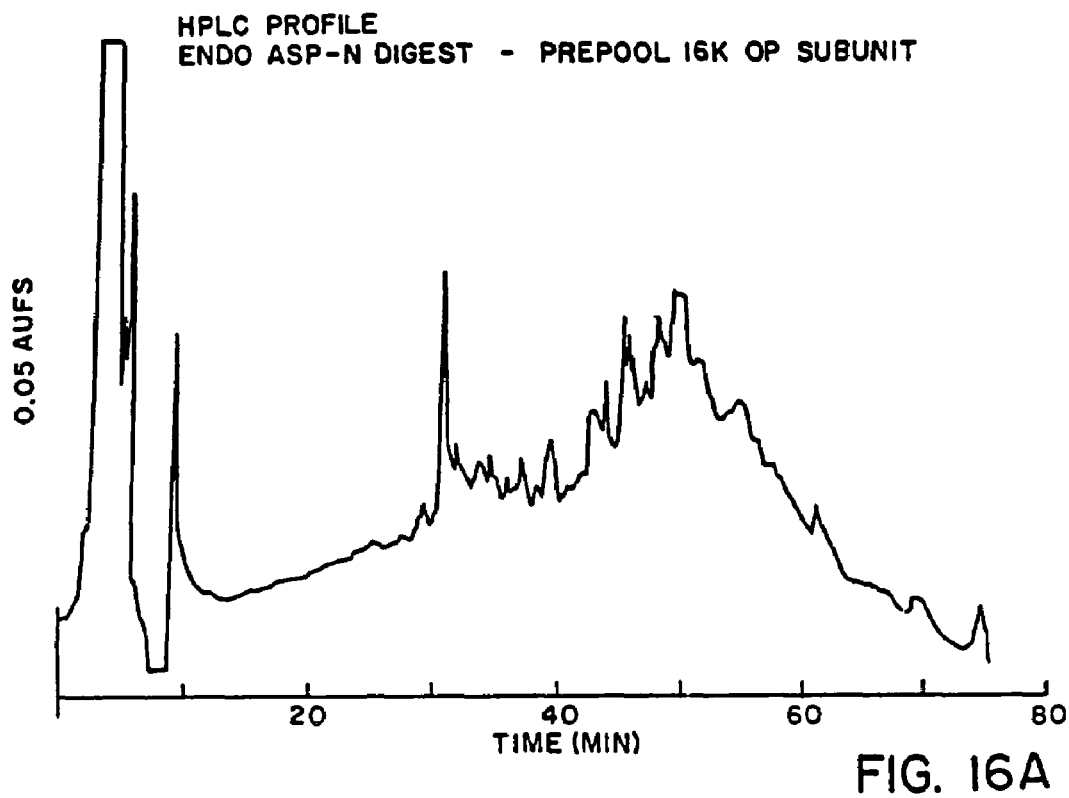
FIG. 16 is a pair of HPLC chromatograms of Endo Asp N proteinase digests of the 18 kD subunit (A) and 16 kD subunit (B)
Figure 16B:
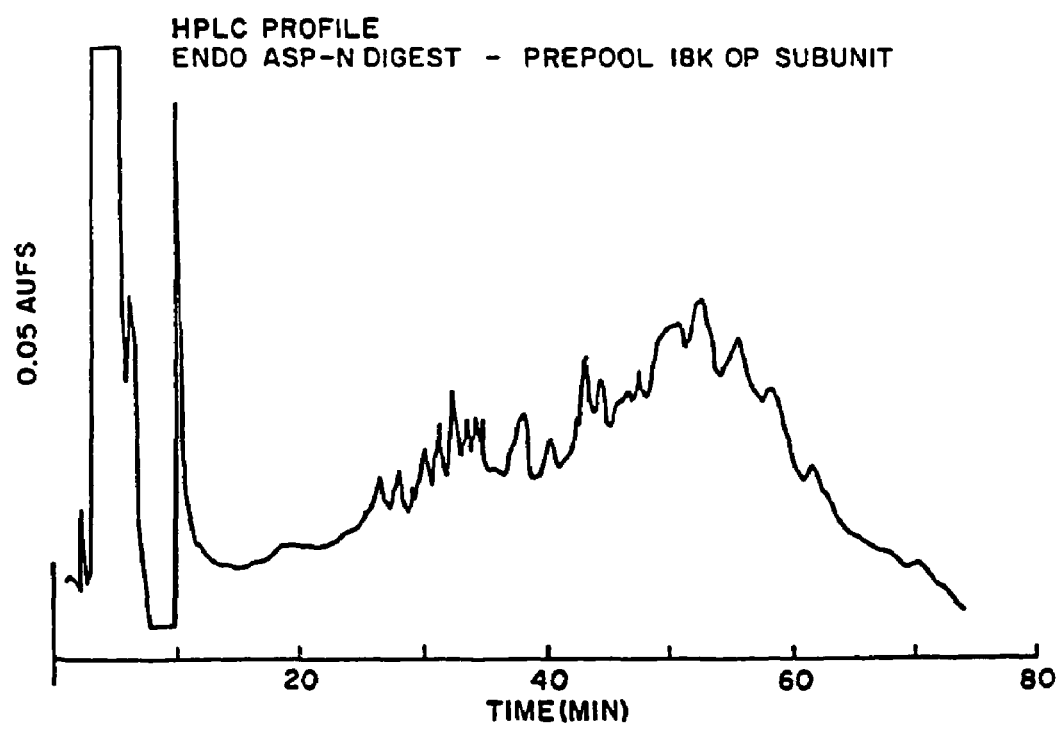

The 16 kD and 18 kD subunits are digested with Endo Asp N proteinase. The protein is treated with 0.5 mg EndoAsp-N in 50 mM sodium phosphate buffer, pH 7.8 at 36° C. for 20 hr. The conditions for fractionation are the same as those described previously for the 30 kD, 16 kD, and 18 kD digests. The profiles obtained are shown in FIGS. 16A and 16B.

Various of the peptide fragments produced using the foregoing procedures have been analyzed in an automated amino acid sequencer (Applied Biosystems 470A with 120A on-line PTH analysis). The following sequence data has been obtained:

(1)  S-F-D-A-Y-Y-C-S-G-A-C-Q-F-P-M-P-K;
     (SEQ ID NO: 17)

(2)  S-L-K-P-S-N-Y-A-T-I-Q-S-I-V;
     (SEQ ID NO: 18)

(3)  A-C-C-V-P-T-E-L-S-A-I-S-M-L-Y-L-D-E-N-E-K;
     (SEQ ID NO: 19)

(4)  M-S-S-L-S-I-L-F-F-D-E-N-K;
     (SEQ ID NO: 20)

(5)  S-Q-E-L-Y-V-D-F-Q-R;
     (SEQ ID NO: 21)

(6)  F-L-H-C-Q-F-S-E-R-N-S;
     (SEQ ID NO: 22)

(7)  T-V-G-Q-L-N-E-Q-S-S-E-P-N-I-Y;
     (SEQ ID NO: 23)

(8)  L-Y-D-P-M-V-V;
     (SEQ ID NO: 24)

(9)  V-G-V-V-P-G-I-P-E-P-C-C-V-P-E;
     (SEQ ID NO: 25)

(10) V-D-F-A-D-I-G;
     (SEQ ID NO: 26)

(11) V-P-K-P-C-C-A-P-T;
     (SEQ ID NO: 27)

-continued

(12) I-N-I-A-N-Y-L;
    (SEQ ID NO: 28)

(13) D-N-H-V-L-T-M-F-P-I-A-I-N;
    (SEQ ID NO: 29)

(14) D-E-Q-T-L-K-K-A-R-R-K-Q-W-I-?-P;
    (SEQ ID NO: 30)

(15) D-I-G-?-S-E-W-I-I-?-P;
    (SEQ ID NO: 31)

(16) S-I-V-R-A-V-G-V-P-G-I-P-E-P-?-?-V;
    (SEQ ID NO: 32)

(17) D-?-I-V-A-P-P-Q-Y-H-A-F-Y;
    (SEQ ID NO: 33)

(18) D-E-N-K-N-V-V-L-K-V-Y-P-N-M-T-V-E;
    (SEQ ID NO: 34)

(19) S-Q-T-L-Q-F-D_E-Q-T-L-K-?-A-R-?-K-Q;
    (SEQ ID NO: 35)

(20) D-E-Q-T-L-K-K-A-R-R-K-Q-W-I-E-P-R-N-?-A-R-R-Y-L;
    (SEQ ID NO: 36)

(21) A-R-R-K-Q-W-I-E-P-R-N-?-A-?-R-Y-?-?-V-D;
    (SEQ ID NO: 37)
and

(22) R-?-Q-W-I-E-P-?-N-?-A-?-?-Y-L-K-V-D-?-A-?-?-G.
    (SEQ ID NO: 38)

Strategies for obtaining amino acid composition were developed using gel elution from 15% SDS gels, transfer onto Immobilon, and hydrolysis Immobilon membrane is a polymer of vinylidene difluoride and, therefore, is not susceptible to acid cleavage. Samples of oxidized (30 kD) and reduced (16 kD and 18 kD) BOP are electrophoresed on a gel and transferred to Immobilon for hydrolysis and analysis as described below. The composition date generated by amino acid analyses of 30 kD BOP is reproducible, with some variation in the number of residues for a few amino acids, especially cysteine and isoleucine.

Samples are run on 15% SDS gels, transferred to Immobilon, and stained with Coomassie blue. The bands of interest are excised from the Immobilon, with a razor blade and placed in a 6×50 mm Corning test tube cleaned by pyrolysis at 550° C. When cysteine is to be determined, the samples are treated with performic acid, which converts cysteine to cysteic acid. Cysteic acid is stable during hydrolysis with HCl, and can be detected during the HPLC analysis by using a modification of the normal Pico-Tag eluents (Millipore) and gradient. The performic acid is made by mixing 50 ml 30% hydrogen peroxide with 950 ml 99% formic acid, and allowing this solution to stand at room temperature for 2 hr. The samples are then treated with performic acid (PFA); 20 ml PFA is pippetted onto each sample and placed in an ice bath at 4° C. for 2.5 hours. After 2.5 hr. the PFA is removed by drying in vacuo, and the samples are then hydrolyzed. A standard protein of known composition and concentration containing cysteine is treated with PFA and hydrolyzed concurrently with the osteogenic protein samples, to take as a control for hydrolysis and amino acid chromatography.

The hydrolysis of the osteogenic protein samples is done in vacuo. The samples, with empty tubes and Immobilon blanks, are placed in a hydrolysis vessel which is placed in a dry ice/ethanol bath to keep the HCl from prematurely evaporating. 200 ml 6 N HCl containing 2% phenol and 0.1% stannous chloride are added to the hydrolysis vessel outside the tubes containing the samples. The hydrolysis vessel is then sealed, flushed with prepurified nitrogen, evacuated, and then held at 115° C. for 24 hours, after which time the HCl is removed by drying in vacuo.

After hydrolysis, each piece of Immobilon is transferred to a fresh tube, where it is rinsed twice with 100 ml 0.1% TFA, 50% acetonitrile. The washings are returned to the original sample tube, which is then redried as below. A similar treatment of amino acid analysis on Immobilon can be found in the literature (LeGendre and Matsudaira (1988) Biotechniques 6: 154-159).

The samples are redried twice using 2:2:1 ethanol:water: triethylamine and allowed to dry at least 30 min. after each addition of redry reagent. These redrying steps bring the sample to the proper pH for derivatization.

The samples are derivatized using standard methodology. The solution is added to each sample tube. The tubes are placed in a desiccator which is partially evacuated, and are allowed to stand for 20 min. The desiccator is then fully evacuated, and the samples are dried for at least 3 hr. After this step the samples may be stored under vacuum at −20° C. or immediately diluted for HPLC. The samples are diluted with Pico-Tag Sample Diluent (generally 100 ml) and allowed to stand for 20 min., after which they are analyzed on HPLC using the Pico Tag chromatographic system with some minor changes involving gradients, eluents, initial buffer conditions and oven temperature.

After HPLC analysis, the compositions are calculated. The molecular weights are assumed to be 14.4 kD, 16.2 kD, and 27 kD to allow for 10% carbohydrate content. The number of residues is approximated by dividing the molecular weight by the average molecular weight per amino acid, which is 115. The total picomoles of amino acid recovered is divided by the number of residues, and then the picomoles recovered for each amino acid is divided by the number of picomoles per residue, determined above. This gives an approximate theoretical number of residues of each amino acid in the protein. Glycine content may be overestimated in this type of analysis.

Composition data obtained are shown in TABLE 5.

TABLE 5

| BOP Amino Acid Analyses | | | |
|---|---|---|---|
| Amino Acid | 30 kD | 16 kD | 18 kD |
| Aspartic Acid/Asparagine | 22 | 14 | 15 |
| Glutamic Acid/Glutamine | 24 | 14 | 16 |
| Serine | 24 | 16 | 23 |
| Glycine | 29 | 18 | 26 |
| Histidine | 5 | * | 4 |
| Arginine | 13 | 6 | 6 |
| Threonine | 11 | 6 | 7 |
| Alanine | 18 | 11 | 12 |
| Proline | 14 | 6 | 6 |
| Tyrosine | 11 | 3 | 3 |
| Valine | 14 | 8 | 7 |
| Methionine | 3 | 0 | 2 |
| Cysteine** | 16 | 14 | 12 |
| Isoleucine | 15 | 14 | 10 |
| Leucine | 15 | 8 | 9 |
| Phenylalanine | 7 | 4 | 4 |
| Tryptophan | ND | ND | ND |
| Lysine | 12 | 6 | 6 |

*This result is not integrated because histidine is present in low quantities.
**Cysteine is corrected by percent normally recovered from performic acid hydrolysis of the standard protein.

The results obtained from the 16 kD and 18 kD subunits, when combined, closely resemble the numbers obtained from the native 30 kD protein. The high figures obtained for glycine and serine are most likely the result of gel elution.

D. Purification of Human Osteogenic Protein

Human bone is obtained from the Bone Bank, (Massachusetts General Hospital, Boston, Mass.), and is milled, defatted, demarrowed and demineralized by the procedure disclosed above. 320 g of mineralized bone matrix yields 70-80 g of demineralized bone matrix. Dissociative extraction and ethanol precipitation of the matrix gives 12.5 g of guanidine-HCl extract.

Figure 10:
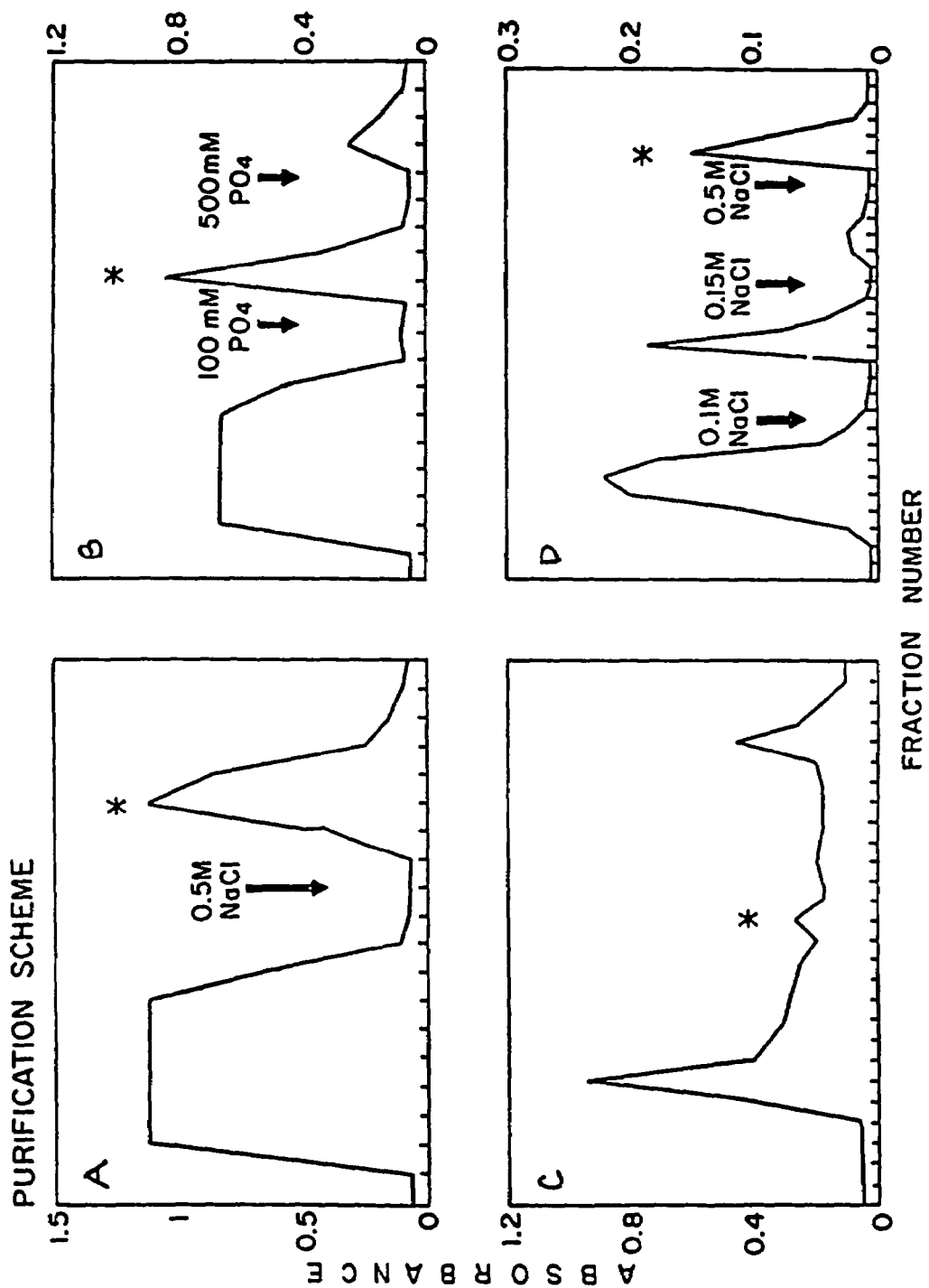
FIG. 10 is a collection of graphs of protein concentration (as indicated by optical absorption) vs. elution volume illustrating the results of human protein fractionation on Heparin-Sepharose I (A), HAP-Ultragel (B), TSK 3000/2000 (C), and heparin-Sepharose II (D). Arrows indicate buffer changes.

One third of the ethanol precipitate (0.5 g) is used for gel filtration through 4 M guanidine-HCl (FIG. 10A). Approximately 70-80 g of ethanol precipitate per run is used. In vivo bone inducing activity is localized in the fractions containing proteins in the 30 kD range. They are pooled and equilibrated in 6 M urea, 0.5 M NaCl buffer, and applied directly onto a HAP column; the bound protein is eluted stepwise by using the same buffer containing 100 mM and 500 mM phosphate (FIG. 10B). Bioassay of HAP bound and unbound fractions demonstrates that only the fraction eluted by 100 mM phosphate has bone inducing activity in vivo. The biologically active fraction obtained from HAP chromatography is subjected to heparin-Sepharose affinity chromatography in buffer containing low salt; the bound proteins are eluted by 0.5 M NaCl (FIG. 10C). Assaying the heparin-Sepharose fractions shows that the bound fraction eluted by 0.5M BaCl have bone-inducing activity. The active fraction is then subjected to C-18 reverse phase chromatography. (FIG. 10D).

The active fraction can then be subjected to SDS-PAGE as noted above to yield a band at about 30 kD comprising substantially pure human osteogenic protein.

E. Biosynthetic Probes for Isolation of Genes Encoding Native Osteogenic Protein E-1 Probe Design A synthetic consensus gene shown in FIG. 13 was designed as a hybridization probe (and to encode a consensus protein, see below) based on amino acid predictions from homology with the TGF-beta gene family and using human codon bias as found in human TGF-beta. The designed concensus sequence was then constructed using known techniques involving assembly of oligonucleotides manufactured in a DNA synthesizer.

Tryptic peptides derived from BOP and sequenced by Edman degradation provided amino acid sequences that showed strong homology with the *Drosophila* DPP protein sequence (as inferred from the gene), the *Xenopus* VG1 protein, and somewhat less homology to inhibin and TGF-beta, as demonstrated below in TABLE 6.

TABLE 6

| protein | amino acid sequence | homology |
|---|---|---|
| (BOP) SEQ ID NO: 55 | SFDAYYCSGACQFPS<br>***** * * ** | (9/15 matches) |
| (DPP) SEQ ID NO: 56 | GYDAYYCHGKCPFFL | |
| (BOP) SEQ ID NO: 55 | SFDAYYCSGACQFPS<br>* ** * * * | (6/15 matches) |
| (Vgl) SEQ ID NO: 57 | GYMANYCYGECPYPL | |
| (BOP) SEQ ID NO: 55 | SFDAYYCSGACQFPS<br>* ** * * | (5/15 matches) |

TABLE 6-continued

| protein | amino acid sequence | homology |
|---|---|---|
| (inhibin) SEQ ID NO: 58 | GYHANYCEGECPSHI | |
| (BOP) SEQ ID NO: 55 | SFDAYYCSGACQFPS<br>* * * * | (4/15 matches) |
| (TGF-beta) SEQ ID NO: 59 | GYHANFCLGPCPYIW | |
| (BOP) SEQ ID NO: 60 | K/RACCVPTELSAISMLYLDEN<br>***** * **** * * | (12/20 matches) |
| (Vgl) SEQ ID NO: 61 | LPCCVPTKMSPISMLFYDNN | |
| (BOP) SEQ ID NO: 60 | K/RACCVPTELSAISMLYLDEN<br>* ***** * **** * | (12/20 matches) |
| (inhibin) SEQ ID NO: 62 | KSCCVPTKLRPMSMLYYDDG | |
| (BOP) SEQ ID NO: 60 | K/RACCVPTELSAISMLYLDE<br>**** * * | (6/19 matches) |
| (TGF-beta) SEQ ID NO: 63 | APCCVPQALEPLPIVYYVG | |
| (BOP) SEQ ID NO: 60 | K/RACCVPTELSAISMLYLDEN<br>******* * **** | (12/20 matches) |
| (DPP) SEQ ID NO: 64 | KACCVPTQLDSVAMLYLNDQ | |
| (BOP) SEQ ID NO: 65 | LYVDF<br>***** | (5/5 matches) |
| (DPP) SEQ ID NO: 66 | LYVDF | |
| (BOP) SEQ ID NO: 65 | LYVDF<br>*** * | (4/5 matches) |
| (Vgl) SEQ ID NO: 67 | LYVEF | |
| (BOP) SEQ ID NO: 65 | LYVDF<br>** ** | (4/5 matches) |
| (TGF-beta) SEQ ID NO: 68 | LYIDF | |
| (BOP) SEQ ID NO: 65 | LYVDF<br>* * | (2/4 matches) |
| (inhibin) SEQ ID NO: 69 | FFVSF | |

*-match

In determining the amino acid sequence of an osteogenic protein (from which the nucleic acid sequence can be determined), the following points were considered: (1) the amino acid sequence determined by Edman degradation of osteogenic protein tryptic fragments is ranked highest as long as it has a strong signal and shows homology or conservative changes when aligned with the other members of the gene family; (2) where the sequence matches for all four proteins, it is used in the synthetic gene sequence; (3) matching amino acids in DPP and Vg1 are used; (4) If Vg1 or DPP diverged but either one were matched by inhibin of by TGF-beta, this matched amino acid is chosen; (5) where all sequences diverged, the DPP sequence is initially chose, with a later plan of creating the Vg1 sequence by mutagenesis kept as a possibility. In addition, the consensus sequence is designed to preserve the disulfide crosslinking and the apparent structural homology.

One purpose of the originally designed synthetic consensus gene sequence, designated COP0., (see FIG. 13), was to serve as a probe to isolate natural genes. For this reason the DNA was designed using human codon bias. Alternatively, probes may be constructed using conventional techniques comprising a group of sequences of nucleotides which encode any portion of the amino acid sequence of the osteogenic protein produced in accordance with the foregoing isolation procedure. Use of such pools of probes also will enable isolation of a DNA encoding the intact protein.

E-2 Retrieval of Genes Encoding Osteogenic Protein from Genomic Library

A human genomic library (Maniatis-library) carried in lambda phage (Charon 4A) was screened using the COP0 consensus gene as probe. The initial screening was of 500,000 plaques (10 plates of 50,000 each). Areas giving hybridization signal were punched out from the plates, phage particles were eluted and plated again at a density of 2000-3000 plaques per plate. A second hybridization yielded plaques which were plated once more, this time at a density of ca 100 plaques per plate allowing isolation of pure clones. The probe (COP0) is a 300 base pair BamHI-PstI fragment restricted from an amplification plasmid which was labeled using alpha 32 dCTP according to the random priming method of Feinberg and Vogelstein, Anal. Biochem., 137, 266-267, 1984. Prehybridization was done for 1 hr in 5×SSPE, 10×Denhardt's mix, 0.5% SDS at 50° C. Hybridization was overnight in the same solution as above plus probe. The washing of nitrocellulose membranes was done, once cold for 5 min. in 1×SSPE with 0.1% SDS and twice at 50° C. for 2×30 min. in the same solution. Using this procedure, twenty-four positive clones were found. Two of these yielded the genes corresponding to BMP-2b, one yielded BMP-3 (see PCT US 87/01537) and two contained a gene never before reported designated OP1, osteogenic protein-1 described below.

Southern blot analysis of lambda #13 DNA showed that an approximately 3 kb BamHI fragment hybridized to the probe. (See FIG. 1B). This fragment was isolated and subcloned into a bluescript vector (at the BamHI site). The clone was further analyzed by Southern blotting and hybridization to the COP0 probe. This showed that a 1 kb (approx.) EcoRI fragment strongly hybridized to the probe. This fragment was subcloned into the EcoRI site of a bluescript vector, and sequenced. Analysis of this sequence showed that the fragment encoded the carboxy terminus of a protein, named osteogenic protein-1 (OP1). The protein was identified by amino acid homology with the TGF-beta family. For this comparison cysteine patterns were used and then the adjacent amino acids were compared. Consensus splice signals were found where amino acid homologies ended, designating exon intron boundaries. Three exons were combined to obtain a functional TGF-beta-like domain containing seven cysteines. Two introns were deleted by looping out via primers bridging the exons using the single stranded mutagenesis method of Kunkel. Also, upstream of the first cysteine, an EcoRI site and an asp-pro junction for acid cleavage were introduced, and at the 3' end a PstI site was added by the same technique. Further sequence information (penultimate exon) was obtained by sequencing the entire insert. The sequencing was done by generating a set of unidirectionally deleted clones (Ozkaynak, E., and Putney, S.: Biotechniques, 5, 770-773, 1987). The obtained sequence covers about 80% of the TGF-beta-like region of OP1 and is set forth in FIG. 1A. The complete sequence of the TGF-beta like region was obtained by first subcloning all EcoRI generated fragments of lambda clone #13 DNA and sequencing a 4 kb fragment that includes the first portion of the TGF-beta like region (third exon counting from end) as well as sequences characterized earlier. The gene on an EcoRI to PstI fragment was inserted into an *E. coli* expression vector controlled by the trp promoter-operator to produce a modified trp LE fusion protein with an acid cleavage site. The OP1 gene encodes amino acids corresponding substantially to a peptide found in sequences of naturally sourced material. The amino acid sequence of what is believed to be its active region is set forth below:

```
              1         10        20        30        40
OP1           LYVSFR-DLGWQDWIIAPEGYAAYYCEGECAFPLNS
                        50        60        70
              YMNATN--H-AIVQTLVHFINPET-VPKPCCAPTQLNA
                        80        90       100
              ISVLYFDDSSNVILKKYRNMVVRACGCH
              (SEQ ID NO: 39)
```

A longer active sequence is:

```
                                                    -5
                                                  HQRQA
              1         10        20        30        40
OP1           CKKHELYVSFR-DLGWQDWIIAPEGYAAYYCEGECAFPLNS
                        50        60        70
              YMNATN--H-AIVQTLVHFINPET-VPKPCCAPTQLNA
                        80        90       100
              ISVLYFDDSSNVILKKYRNMVVRACGCH
              (SEQ ID NO: 9)
```

E-3 Probing cDNA Library

Another example of the use of pools of probes to enable isolation of a DNA encoding the intact protein is shown by the following. Cells known to express the protein are extracted to isolate total cytoplasmic RNA. An oligo-dT column can be used to isolate mRNA. This mRNA can be size fractionated by, for example, gel electrophoresis. The fraction which includes the mRNA of interest may be determined by inducing transient expression in a suitable host cell and testing for the presence of osteogenic protein using, for example, antibody raised against peptides derived from the tryptic fragments of osteogenic protein in an immunoassay. The mRNA fraction is then reverse transcribed to single stranded cDNA using reverse transcriptase; a second complementary DNA strand can then be synthesized using the cDNA as a template. The double-standard DNA is then ligated into vectors which are used to transfect bacteria to produce a cDNA library.

The radiolabelled consensus sequence, portions thereof, and/or synthetic deoxy oligonucleotides complementary to codons for the known amino acid sequences in the osteogenic protein may be used to identify which of the DNAs in the cDNA library encode the full length osteogenic protein by standard DNA-DNA hybridization techniques.

The cDNA may then be integrated in an expression vector and transfected into an appropriate host cell for protein expression. The host may be a prokaryotic or eucaryotic cell since the former's inability to glycosylate osteogenic protein will not effect the protein's enzymatic activity. Useful host cells include *Saccharomyces, E. Coli*, and various mammalian cell cultures. The vector may additionally encode various signal sequences for protein secretion and/or may encode osteogenic protein as a fusion protein. After being translated, protein may be purified from the cells or recovered from the culture medium.

II. Recombinant Non-Native Osteogenic Protein Constructs

A. Protein Design

This section discloses the production of novel recombinant proteins capable of inducing cartilage and endochondral bone comprising a protein structure duplicative of the functional domain of the amino acid sequence encoded by consensus DRA sequences derived from a family of natural proteins implicated in tissue development. These gene products/proteins are known to exist in active form as dimers and are, in general, processed from a precursor protein to produce an active C-terminal domain of the precursor.

The recombinant osteogenic/chondrogenic proteins are "novel" in the sense that, as far as applicants are aware, they do not exist in nature or, if they do exist, have never before been associated with bone or cartilage formation. The approach to design of these proteins was to employ amino acid sequences, found in the native isolates described above, in polypeptide structures which are patterned after certain proteins reported in the literature, or the amino acid sequences inferred from DNAs reported in the literature. Thus, using the design criteria set forth above in the probe design section, and refining the amino acid sequence as more protein sequence information was learned, a series of synthetic proteins were designed with the hope and intent that they might have osteogenic or chondrogenic activity when tested in the bioassay system disclosed below.

It was noted, for example, that DPP from *drosophila*, VG1 from *Xenopus*, the TGF beta family of proteins, and to a lesser extent, alpha and beta inhibins, had significant homologies with certain of the sequences derived from the naturally sourced OP product. (FIG. 18.) Study of these proteins led to the realization that a portion of the sequence of each had a structural similarity observable by analysis of the positional relationship of cysteines and other amino acids which have an important influence on three dimensional protein conformation. It was noted that a region of these sequences had a series of seven cysteines, placed very nearly in the same relative positions, and certain other amino acids in sequence as set forth below:

```
         10        20        30        40        50
CXXXXLXVXFXDXGWXXWXXXPXGXXAXYCXGXCXXPXXXXXXXXNHAXX 60        70        80        90
QXXVXXXNXXXXPXXCCXPXXXXXXXXLXXXXXXXXVXLXXYXXMXVX

100
XCXCX
(SEQ ID NO: 4)
``` wherein each X independently represents an amino acid. Expression experiments with constructs patterned after this template amino acid sequence showed activity occurred with a shorter sequence having only six cysteines (SEQ ID NO: 3):

```
         10        20        30        40        50
     LXVXFXDXGWXXWXXXPXGXXAXYCXGXCXXPXXXXXXXXNHAXX 60        70        80        90
QXXVXXXNXXXXPXXCCXPXXXXXXXXLXXXXXXXXVXLXXYXXMXVX

100
XCXCX
``` wherein each X independently represents an amino acid. Within these generic structures are a multiplicity of specific sequences which have osteogenic or chondrogenic activity. Preferred structures are those having the amino acid sequence:

```
         10        20        30        40        50
CKRHPLYVDFRDVGWNDWIVAPPGYHAFYCHGECPFPLADHLNSTNHAIV
 RRRS K S S L   QE VIS E FD Y   E A AY MPESMKAS    VI
   KE F E K I    DN     L    N S  Q  ITK F P       TL
    Q     A     S       K 60        70        80        90
QTLVNSVNPGKIPKACCVPTELSAISMLYLDENENVVLKNYQDMVV
 SI HAI SEQV EP  A EQMNSLAI FFNDQDK I RK  EE T
    RF    T    S     K DPV V  Y N S       H RN
     N    S                        K        P

100
EGCGCR
 DA H H
 RS
  E
(SEQ ID NO: 6)
```

Wherein, in each position where more than one amino acid is shown, any one of the amino acids shown may be used. Novel active proteins also are defined by amino acid sequences comprising an active domain beginning at residue number 6 of this sequence, i.e., omitting the N terminal CXXXX, or omitting any of the preferred specific combinations such as CKRHP (SEQ ID NO: 70), CRRKQ (SEQ ID NO: 71), CKRHE (SEQ ID NO: 72), etc., resulting in a construct having only 6 cystein residues. After this work, PCT 87/01537 was published, and it was observed that the proteins there identified as BMPII a and b and BMPIII each comprised a region embodying this generic structure. These proteins were not demonstrated to be osteogenic in the published application. However, applicants discovered that a subpart of the amino acid sequence of these proteins, properly folded, and implanted as set forth herein, is active. These are disclosed herein as CBMPIIa, CBMPIIb, and CBMPIII. Also, the OP1 protein was observed to exhibit the same generic structure.

Thus, the preferred osteogenic proteins are expressed from recombinant DNA and comprise amino acid sequences including any of the following sequences:

```
          1       10        20        30        40
Vg1    CKKRHLYVEFK-DVGWQNWVIAPQGYMANYCYGECPYPLTE
                   50        60        70
       ILNGSN--H-AILQTLVHSIEPED-IPLPCCVPTKMSP
               80        90       100
       ISMLFYDNNDNVVLRHYENMAVDECGCR
       (SEQ ID NO: 7)

1       10        20        30        40
DPP    CRRHSLYVDFS-DVGWDDWIVAPLGYDAYYCHGKCPFPLAD
                   50        60        70
       HFNSTN--H-AVVQTLVNNNNPGK-VPKACCVPTQLDS
               80        90       100
       VAMLYLNDQSTVVLKNYQEMTVVGCGCR
       (SEQ ID NO: 8)

1       10        20        30        40
Op1       LYVSFR-DLGWQDWIIAPEGYAAYYCEGECAFPLNS
                   50        60        70
       YMNATN--H-AIVQTLVHFINPET-VPKPCCAPTQLNA
               80        90       100
       ISVLYFDDSSNVILKKYRNMVVRACGCH
       (SEQ ID NO: 39)

-5
                                            HQRQA
          1       10        20        30        40
Op1    CKKHELYVSFR-DLGWQDWIIAPEGYAAYYCEGECAFPLNS
                   50        60        70
       YMNATN--H-AIVQTLVHFINPET-VPKPCCAPTQLNA
               80        90       100
       ISVLYFDDSSNVILKKYRNMVVRACGCH
       (SEQ ID NO: 9)
```

-continued

```
              1         10        20        30        40
CBMP-2a   CKRHPLYVDFS-DVGWNDWIVAPPGYHAFYCHGECPFPLAD
                   50        60        70
          HLNSTN--H-AIVQTLVNSVNS-K-IPKACCVPTELSA
                   80        90       100
          ISMLYLDENEKVVLKNYQDMVVEGCGCR
          (SEQ ID NO: 10)

1         10        20        30        40
CBMP-2b   CRRHSLYVDFS-DVGWNDWIVAPPGYQAFYCHGDCPFPLAD
                   50        60        70
          HLNSTN--H-AIVQTLVNSVNS-S-IPKACCVPTELSA
                   80        90       100
          ISMLYLDEYDKVVLKNYQEMVVEGCGCR
          (SEQ ID NO: 11)

1         10        20        30        40
CBMP-3    CARRYLKVDFA-DIGWSEWIISPKSFDAYYCSGACQFPMPK
                   50        60        70
          SLKPSN--H-ATIQSIVRAVGVVPGIPEPCCVPEKMSS
                   80        90       100
          LSILFFDENKNVVLKVYPNMTVESCACR
          (SEQ ID NO: 12)

1         10        20        30        40
COP1          LYVDFQRDVGWDDWIIAPVDFDAYYCSGACQFPSAD
                   50        60        70
          HFNSTN--H-AVVQTLVNNMNPGK-VPKPCCVPTELSA
                   80        90       100
          ISMLYLDENSTVVLKNYQEMTVVGCGCR
          (SEQ ID NO: 13)

1         10        20        30        40
COP3          LYVDFQRDVGWDDWIVAPPGYQAFYCSGACQFPSAD
                   50        60        70
          HFNSTN--H-AVVQTLVNNMNPGK-VPKPCCVPTELSA
                   80        90       100
          ISMLYLDENEKVVLKNYQEMVVEGCGCR
          (SEQ ID NO: 14)

1         10        20        30        40
COP4          LYVDFS-DVGWDDWIVAPPGYQAFYCSGACQFPSAD
                   50        60        70
          HFNSTN--H-AVVQTLVNNMNPGK-VPKPCCVPTELSA
                   80        90       100
          ISMLYLDENEKVVLKNYQEMVVEGCGCR
          (SEQ ID NO: 15)

1         10        20        30        40
COP5          LYVDFS-DVGWDDWIVAPPGYQAFYCHGECPFPLAD
                   50        60        70
          HFNSTN--H-AVVQTLVNSVNSKI--PKACCVPTELSA
                   80        90       100
          ISMLYLDENEKVVLKNYQEMVVEGCGCR
          (SEQ ID NO: 1)

1         10        20        30        40
COP7          LYVDFS-DVGWNDWIVAPPGYHAFYCHGECPFPLAD
                   50        60        70
          HLNSTN--H-AVVQTLVNSVNSKI--PKACCVPTELSA
                   80        90       100
          ISMLYLDENEKVVLKNYQEMVVEGCGCR
          (SEQ ID NO: 2)

10
                                    PKHHSQRARKKNKN
              1         10        20        30        40
COP16     CRRHSLYVDFS-DVGWNDWIVAPPGYQAFYCHGECPFPLAD
                   50        60        70
          HFNSTN--H-AVVQTLVNSVNSKI--PKACCVPTELSA
                   80        90       100
          ISMLYLDENEKVVLKNYQEMVVEGCGCR
          (SEQ ID NO: 16)
```

As shown in FIG. 18, these sequences have considerable homology with the alpha and beta inhibins, three forms of TGF beta, and MIS.

B. Gene Preparation

The synthetic genes designed as described above preferably are produced by assembly of chemically synthesized oligonucleotides. 15-100 mer oligonucleotides may be synthesized on a Biosearch DNA Model 8600 Synthesizer, and purified by polyacrylamide gel electrophoresis (PAGE) in Tris-Borate-EDTA buffer (TBE). The DNA is then electroeluted from the gel. Overlapping oligomers may be phosphorylated by T4 polynucleotide kinase and ligated into larger blocks which may also be purifed by PAGE. Natural gene sequences and cDNAs also may be used for expression.

C. Expression

Figure 21A:
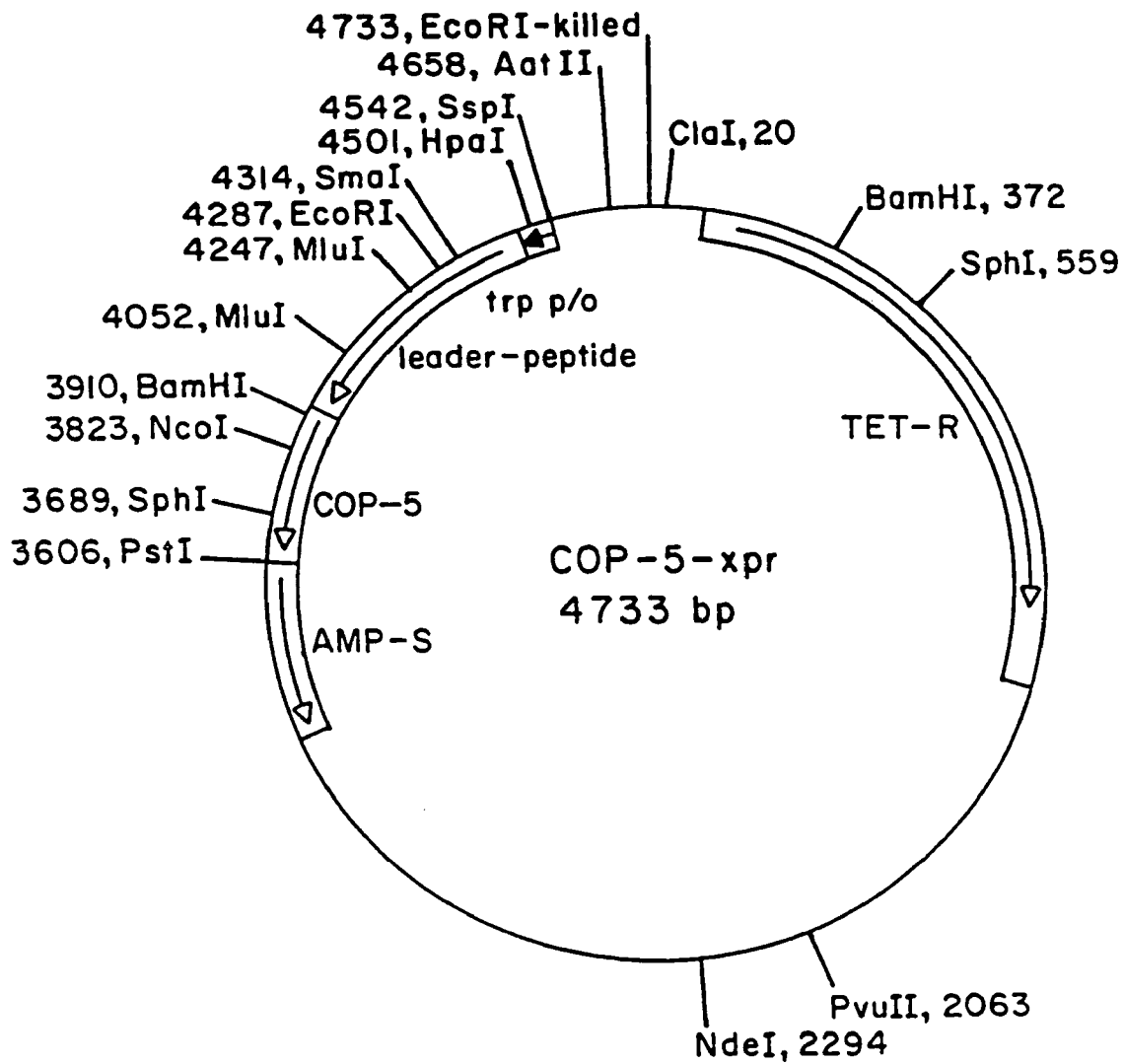
FIG. 21A is an *E. coli* expression vector containing a gene of an osteogenic protein fused to a leader protein.

The genes can be expressed in appropriate prokaryotic hosts such as various strains of *E. coli*. For example, if the gene is to be expressed in *E. coli*, it must first be cloned into an expression vector. An expression vector (FIG. 21A) based on pBR322 and containing a synthetic trp promoter operator and the modified trp LE leader can be opened at the EcoRI and PSTI restriction sites, and a FB-FB COP gene fragment (FIG. 21B) can be inserted between these sites, where FB is fragment B of Staphylococcal Protein A. The expressed fusion protein results from attachment of the COP gene to a fragment encoding FB. The COP protein is joined to the leader protein via a hinge region having the sequence asp-pro-asn-gly. This hinge permits chemical cleavage of the fusion protein with dilute acid at the asp-pro site or cleavage at asn-gly with hydroxylamine, resulting in release of the COP protein.

D. Production of Active Proteins

The following procedure was followed for production of active recombinant protiens. *E. coli* cells containing the fusion proteins were lysed. The fusion proteins were purified by differential solubilization. In the case of the COP 1, 3, 4, 5, and 7 fusion proteins, cleavage was with dilute acid, and the resulting cleavage products were passed through a Sephacryl-200HR column. The Sephacryl column separated most of the uncleaved fusion products from the COP 1, 3, 4, 5, and 7 analogs. In the case of the COP 16 fusion protein, cleavage was with a more concentrated acid, and an SP-Trisacryl column was used to separate COP 16, the leader protein, and the residual fusion protein. The COP fractions from any of the COP analogs were then subjected to HPLC on a semi-prep C-18 column. The HPLC column primarily separated the leader proteins and other minor impurities from the COP analogs.

Initial conditions for refolding of COP analogs were at pH 8.0 using Tris, GuHCl, dithiothreitol. Final conditions for refolding of COP analogs were at pH 8.0 using Tris, oxidized glutathione, and lower amounts of GuHCl and dithiothreitol.

E. Production of Antisera

Antisera to COP 7 and COP5 were produced in New Zealand white rabbits. Western blots demonstrate that the antisera react with COP 7 and COP5 preparations. Antisera to COP 7 has been tested for reactivity to bovine osteogenic protein samples. Western blots show a clear reaction with the 30 kD protein and, when reduced, with the 16 kD subunit. The immunoreactive species appears as a closely-spared doublet in the 16K subunit region, similar to the 16K doublet seen in Con A blots.

III. Matrix Preparation

A. General Consideration of Matrix Properties

The carrier described in the bioassay section, infra, may be replaced by either a biodegradable-synthetic or synthetic-inorganic matrix (e.g., HAP, collagen, tricalcium phosphate, or polylactic acid, polyglycolic acid and various copolymers thereof). Also xenogeneic bone may be used if pretreated as described below.

Studies have shown that surface charge, particle size, the presence of mineral, and the methodology for combining matrix and osteogenic protein all play a role in achieving successful bone induction. Perturbation of the charge by chemical modification abolishes the inductive response. Particle size influences the quantitative response of new bone; particles between 75 and 420 mm elicit the maximum response. Contamination of the matrix with bone mineral will inhibit bone formation. Most importantly, the procedures used to formulate osteogenic protein onto the matrix are extremely sensitive to the physical and chemical state of both the osteogenic protein and the matrix.

The sequential cellular reactions at the interface of the bone matrix/OP implants are complex. The multistep cascade includes: binding of fibrin and fibronectin to implanted matrix, chemotaxis of cells, proliferation of fibroblasts, differentiation into chondroblasts, cartilage formation, vascular invasion, bone formation, remodeling, and bone marrow differentiation.

A successful carrier for osteogenic protein must perform several important functions. It must bind osteogenic protein and act as a slow release delivery system, accommodate each step of the cellular response during bone development, and protect the osteogenic protein from nonspecific proteolysis. In addition, selected materials must be biocompatible in vivo and biodegradable; the carrier must act as a temporary scaffold until replaced completely by new bone. Polylactic acid (PLA), polyglycolic acid (PGA), and various combinations have different dissolution rates in vivo. In bones, the dissolution rates can vary according to whether the implant is placed in cortical or trabecular bone.

Matrix geometry, particle size, the presence of surface charge, and porosity or the presence of interstices among the particles of a size sufficient to permit cell infiltration, are all important to successful matrix performance. It is preferred to shape the matrix to the desired form of the new bone and to have dimensions which span non-union defects. Rat studies show that the new bone is formed essentially having the dimensions of the device implanted.

The matrix may comprise a shape-retaining solid made of loosely adhered particulate material, e.g., with collagen. It may also comprise a molded, porous solid, or simply an aggregation of close-packed particles held in place by surrounding tissue. Masticated muscle or other tissue may also be used. Large allogeneic bone implants can act as a carrier for the matrix if their marrow cavities are cleaned and packed with particles and the dispersed osteogenic protein.

B. Preparation of Biologically Active Allogenic Matrix

Demineralized bone matrix is prepared from the dehydrated diaphyseal shafts of rat femur and tibia as described herein to produce a bone particle size which pass through a 420 mm sieve. The bone particles are subjected to dissociative extraction with 4 M guanidine-HCl. Such treatment results in a complete loss of the inherent ability of the bone matrix to induce endochondral bone differentiation. The remaining insoluble material is used to fabricate the matrix. The material is mostly collagenous in nature, and upon implantation, does not induce cartilage and bone. All new preparations are tested for mineral content and false positives before use. The total loss of biological activity of bone matrix is restored when an active osteoinductive protein fraction or a pure protein is reconstituted with the biologically inactive insoluble collagenous matrix. The osteoinductive protein can be obtained from any vertebrate, e.g., bovine, porcine, monkey, or human, or produced using recombinant DNA techniques.

C. Preparation of Deglycosylated Bone Matrix for Use in Xenogenic Implant

When osteogenic protein is reconstituted with collagenous bone matrix from other species and implanted in rat, no bone is formed. This suggests that while the osteogenic protein is xenogenic (not species specific), while the matrix is species specific and cannot be implanted cross species perhaps due to intrinsic immunogenic or inhibitory components. Thus, heretofore, for bone-based matrices, in order for the osteogenic protein to exhibit its full bone inducing activity, a species specific collagenous bone matrix was required.

The major component of all bone matrices is Type I collagen. In addition to collagen, extracted bone includes non-collagenous proteins which may account for 5% of its mass. Many non-collagenous components of bone matrix are glycoproteins. Although the biological significance of the glycoproteins in bone formation is not known, they may present themselves as potent antigens by virtue of their carbohydrate content and may constitute immunogenic and/or inhibitory components that are present in xenogenic matrix.

It has now been discovered that a collagenous bone matrix may be used as a carrier to effect bone inducing activity in zenogenic implants, if one first removes the immonogenic and inhibitory components from the matrix. The matrix is deglycosglated chemically using, for example, hydrogen fluoride to achieve this purpose.

Bovine bone residue prepared as described above is sieved, and particles of the 74-420 mM are collected. The sample is dried in vacuo over $P_2O_5$, transferred to the reaction vessel and anhydrous hydrogen fluoride (HF) (10-20 ml/g of matrix) is then distilled onto the sample at −70° C. The vessel is allowed to warm to 0° and the reaction mixture is stirred at this temperature for 60 min. After evaporation of the HF in vacuo, the residue is dried thoroughly in vacuo over KOH pellets to remove any remaining traces of acid.

Extent of deglycosylation can be determined from carbohydrate analysis of matrix samples taken before and after treatment with HF, after washing the samples appropriately to remove non-covalently bound carbohydrates.

The deglycosylated bone matrix is next treated as set forth below:

1) suspend in TBS (Tris-buffered Saline) 1 g/200 ml and stir at 4° C. for 2 hrs;
2) centrifuge then treated again with TBS, 1 g/200 ml and stir at 4° C. overnight; and
3) centrifuged; discard supernatant; water wash residue; and then lyophilized.

IV. Fabrication of Device

Fabrication of osteogenic devices using any of the matrices set forth above with any of the osteogenic proteins described above may be performed as follows.

A. Ethanol Precipitation

In this procedure, matrix was added to osteogenic protein in guanidine-HCl. Samples were vortexed and incubated at a low temperature. Samples were then further vortexed. Cold absolute ethanol was added to the mixture which was then stirred and incubated. After centrifugation (microfuge high speed) the supernatant was discarded. The reconstituted matrix was washed with cold concentrated ethanol in water and then lyophilized.

B. Acetonitrile Trifluoroacetic Acid Lyophilization

In this procedure, osteogenic protein in an acetonitrile trifluoroacetic acid (ACN/TFA) solution was added to the carrier. Samples were vigorously vortexed many times and then lyophilized. Osteogenic protein was added in varying concentrations obtained at several levels of purity that have been tested to determine the most effective dose/purity level in rat in vivo assay.

C. Urea Lyophilization

For those proteins that are prepared in urea buffer, the protein is mixed with the matrix, vortexed many times, and then lyophilized. The lyophilized material may be used "as is" for implants.

V. In Vivo Rat Bioassay

Substantially pure BOP, BOP-rich extracts comprising protein having the properties set forth above, and several of the synthetic proteins have been incorporated in matrices to produce osteogenic devices, and assayed in rat for endochondral bone. Studies in rats show the osteogenic effect to be dependent on the dose of osteogenic protein dispersed in the osteogenic device. No activity is observed if the matrix is implanted alone. The following sets forth guidelines for how the osteogenic devices disclosed herein might be assayed for determining active fractions of osteogenic protein when employing the isolation procedure of the invention, and evaluating protein constructs and matrices for biological activity.

A. Subcutaneous Implantation

The bioassay for bone induction as described by Sampath and Reddi (Proc. Natl. Acad. Sci. USA (1983) 80: 6591-6595), herein incorporated by reference, is used to monitor the purification protocols for endochondral bone differentiation activity. This assay consists of implanting the test samples in subcutaneous sites in allogeneic recipient rats under ether anesthesia. Male Long-Evans rats, aged 28-32 days, were used. A vertical incision (1 cm) is made under sterile conditions in the skin over the thoracic region, and a pocket is prepared by blunt dissection. Approximately 25 mg of the test sample is implanted deep into the pocket and the incision is closed with a metallic skin clip. The day of implantation is designated as day of the experiment. Implants were removed on day 12. The heterotropic site allows for the study of bone induction without the possible ambiguities resulting from the use of orthotopic sites.

B. Cellular Events

The implant model in rats exhibits a controlled progression through the stages of matrix induced endochondral bone development including: (1) transient infiltration by polymorphonuclear leukocytes on day one; (2) mesenchymal cell migration and proliferation on days two and three; (3) chondrocyte appearance on days five and siz; (4) cartilage matrix formation on day seven; (5) cartiliage calcification on day eight; (6) vascular invasion, appearance of osteoblasts, and formation of new bone on days nine and ten; (7) appearance of osteoblastic and bone remodeling and dissolution of the implanted matrix on days twelve to eighteen; and (8) hematopoietic bone marrow differentiation in the ossicle on day twenty-one. The results show that the shape of the new bone conforms to the shape of the implanted matrix.

C. Histological Evaluation

Histological sectioning and staining is preferred to determine the extent of osteogenesis in the implants. Implants are fixed in Bouins Solution, embedded in parafilm, cut into 6-8 mm sections. Staining with toluidine blue or hemotoxylin/eosin demonstrates clearly the ultimate development of endochondrial bone. Twelve day implants are usually sufficient to determine whether the implants show bone inducing activity.

D. Biological Markers

Alkaline phosphatase activity may be used as a marker for osteogenesis. The enzyme activity may be determined spectrophotometrically after homogenization of the implant. The activity peaks at 9-10 days in vivo and thereafter slowly declines. Implants showing no bone development by histology should have little or no alkaline phosphatase activity under these assay conditions. The assay is useful for quantitation and obtaining an estimate of bone formation very quickly after the implants are removed from the rat. In order to estimate the amount of bone formation, the calcium content of the implant is determined.

Implants containing osteogenic protein at several levels of purity have been tested to determine the most effective dose/purity level, in order to seek a formulation which could be produced on an industrial scale. The results as measured by specific activity of alkaline phosphatase and calcium content, and histological examination. For specific activity of alkaline phosphatase is elevated during onset of bone formation and then declines. On the other hand, calcium content is directly proportional to the total amount of bone that is formed. The osteogenic activity due to osteogenic protein is represented by "bone forming units". For example, one bone forming unit represents the amount of protein that is needed for half maximal bone forming activity as compared to rat demineralized bone matrix as control and determined by calcium content of the implant on day 12.

E. Results

E-1. Natural Sourced Osteogenic Protein

Figure 11:
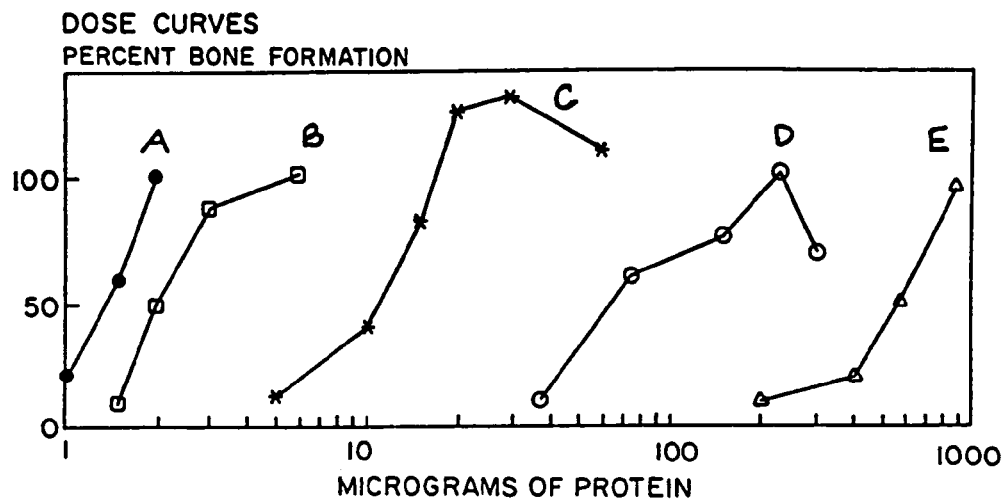
FIG. 11 is a graph showing representative dose response curves for bone-inducing activity in samples from various purification steps including reverse phase HPLC on C-18 (A), Heparin-Sepharose II (B), TSK 3000 (C), HAP-ultragel (D), and Heparin-Sepharose I (E)

Dose curves are constructed for bone inducing activity in vivo at each step of the purification scheme by assaying various concentrations of protein. FIG. 11 shows representative dose curves in rats as determined by alkaline phosphatase. Similar results are obtained when represented as bone forming units. Approximately 10-12 mg of the TSK-fraction, 3-4 mg of heparin-Sepharose-II fraction, 0.4-0.5 mg of the C-18 column purified fraction, and 20-25 ng of gel eluted highly purified 30 kD protein is needed for unequivocal bone formation (half maximum activity). 20-25 ng per 25 mg of implant is normally sufficient to produce endochondral bone. Thus, 1-2 ng osteogenic protein per mg of implant is a reasonable dosage, although higher dosages may be used. (See section IB5 on specific activity of osteogenic protein.)

E-2. Xenogenic Matrix Results

Figure 19:
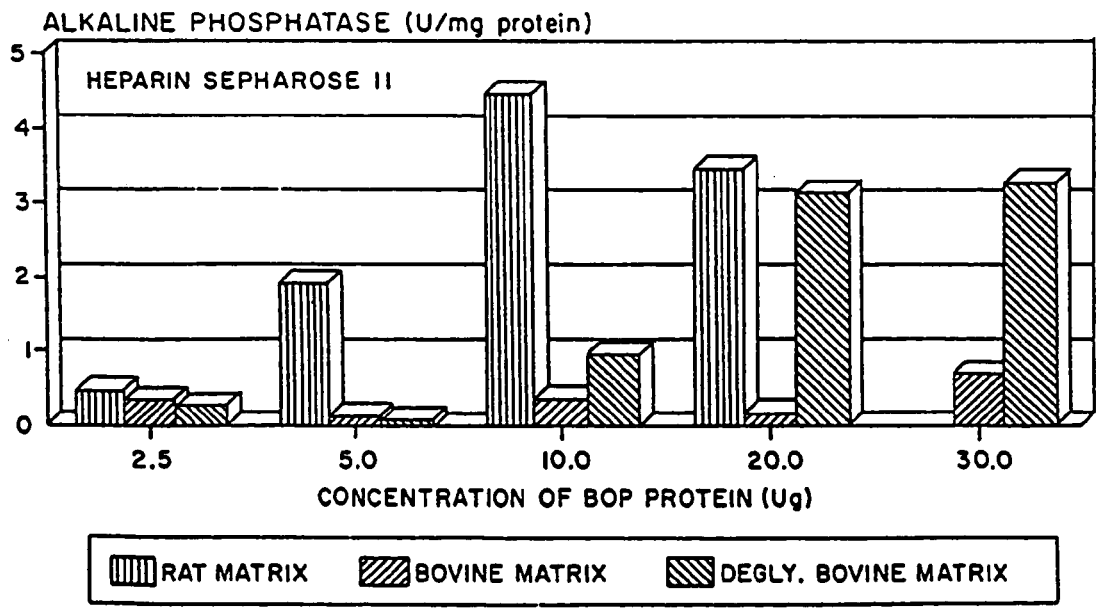
FIG. 19 is a graph illustrating the activity of xenogenic matrix (deglycosylated bovine matrix)

Deglycosylated zenogenic collagenous bone matrix (example: bovine) has been used instead of allogenic collagenous matrix to prepare osteogenic devices (see previous section) and bioassayed in rat for bone inducing activity in vivo. The results demonstrate that xenogenic collagenous bone matrix after chemical deglycosylation induces successful endochondral bone formation (FIG. 19). As shown by specific activity of alkaline phosphotase, it is evident that the deglycosylated xenogenic matrix induced bone whereas untreated bovine matrix did not.

Histological evaluation of implants suggests that the deglycosylated bovine matrix not only has induced bone in a way comparable to the rat residue matrix but also has advanced the developmental stages that are involved in endochondral bone differentiation. Compared to rat residue as control, the HF treated bovine matrix contains extensively remodeled bone. Ossicles are formed that are already filled with bone marrow elements by 12 days. This profound action as elicited by deglycosylated bovine matrix in supporting bone induction is reproducible and is dose dependent with varying concentration of osteogenic protein.

E-3. Synthetic/Recombinant Proteins (COP5, COP7)

Figure 22A:
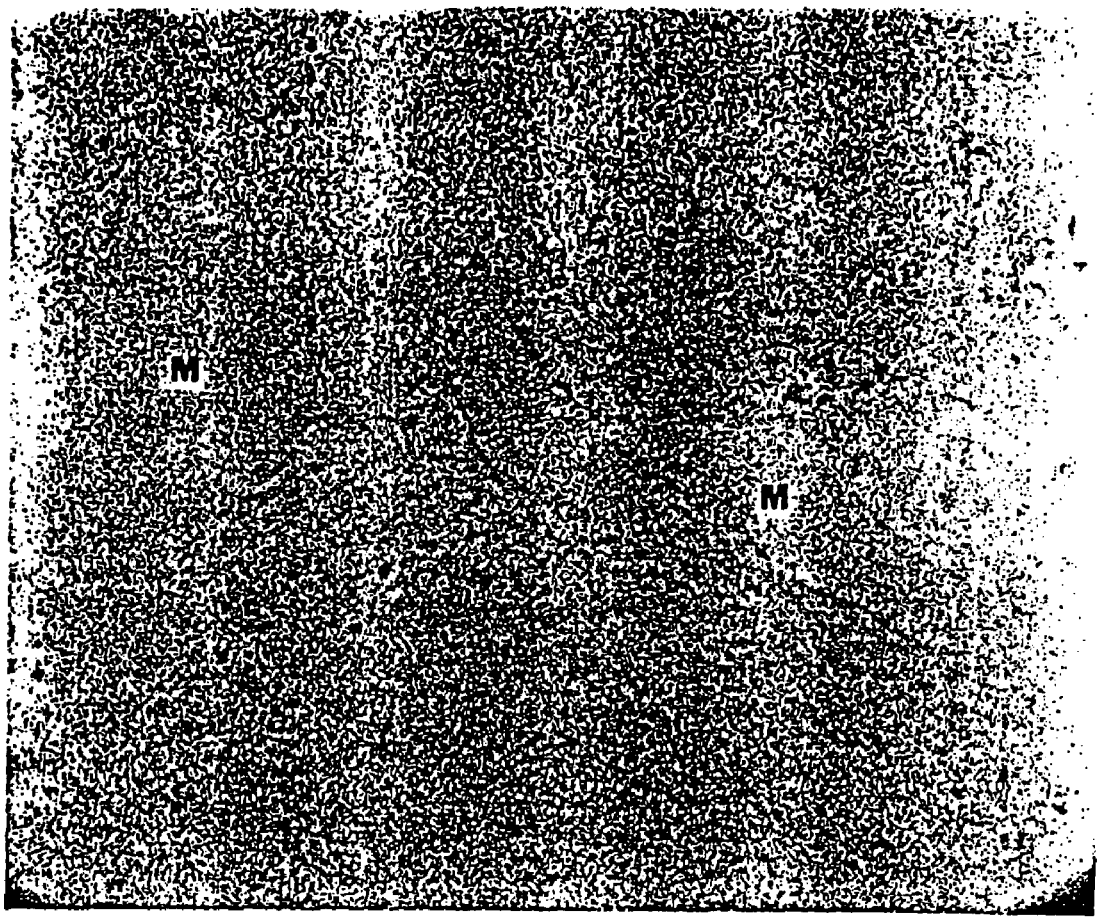
FIGS. 22A and 22B are photomicrographs of implants showing the histology (day 12) of COP5 active recombinant protein. A is a control (rat matrix alone, 25 mg). B is rat matrix plus COP5, showing +++ cartilage formation and ++ bone formation (see key infra). Similar results are achieved with COP7.

The device that contained only rat carrier showed complete absence of new bone formation. The implant consists of carrier rat matrix and surrounding mesenchymal cells. Again, the devices that contained rat carrier and not correctly folded (or biologically inactive) recombinant protein also showed complete absence of bone formation. These implants are scored as cartilage formation (−) and bone formation (−). The endochondral bone formation activity is scored as zero percent (0%). (FIG. 22A)

Implants included biologically active recombinant protein, however, showed evidence of endochondral bone formation. Histologically they showed new cartilage and bone formation.

Figure 22B:
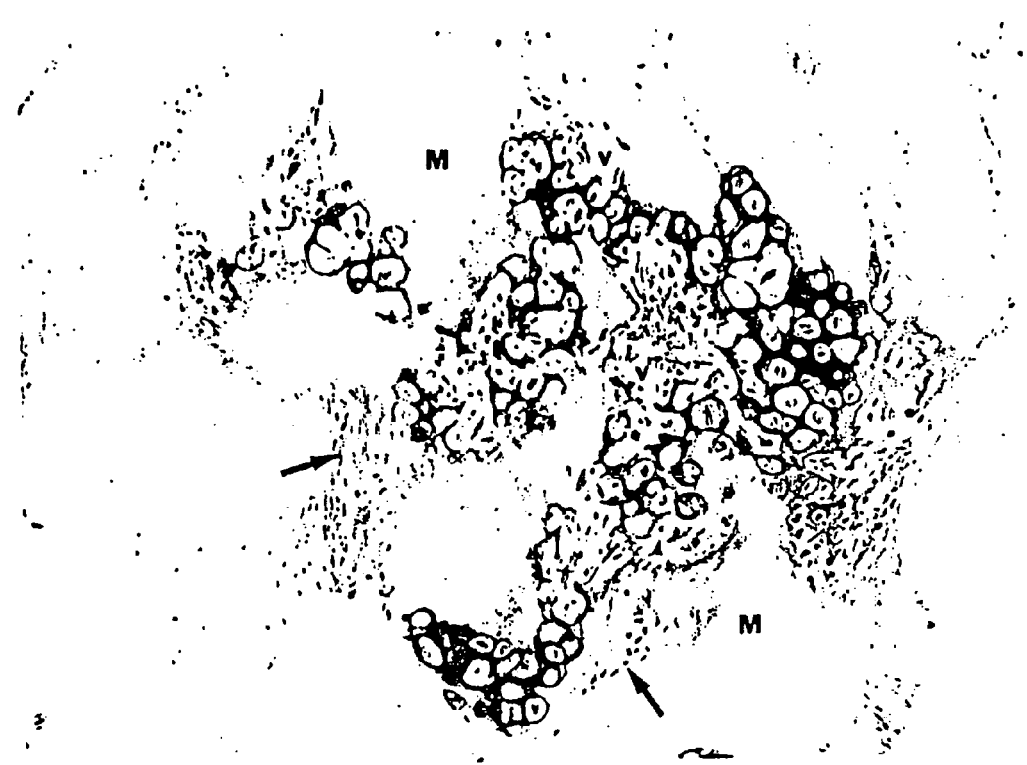

The cartilage formation is scored as (+) by the presence of metachromatically stained chondrocytes in center of the implant, as (++) by the presence of numerous chondrocytes in many areas of the implant and as (+++) by the presence of abundant chondrocytes forming cartilage matrix and the appearance of hypertrophied chondrocytes accompanying cartilage calcification (FIG. 22B).

The bone formation is scored as (+) by the presence of osteoblast surrounding vascular endothelium forming new matrix, and as (++) by the formation of bone due to osteoblasts (as indicated by arrows) and further bone remodeling by the appearance of osteoblasts in apposition to the rat carrier. Vascular invasion is evident in these implants (FIG. 22B).

The overall bone inducing activity due to recombinant protein is represented as percent response of endochondral bone formation (see Table 7 below). The percent response means the area of the implant that is covered by newly induced cartilage and bone as shown by histology in low magnification.

TABLE 7

HISTOLOGICAL EVALUATION OF RECOMBINANT BONE INDUCTIVE PROTEINS

| Implanted Protein | Cartilage Formation | Bone Formation | Percent Response in the Implant |
|---|---|---|---|
| COP-5 | +++ | ++ | 15% |
| COP-5 | ++ | + | 5% |
| COP-7 | +++ | ++ | 30% |
| COP-7 | +++ | ++ | 20% |
| COP-7 | ++ | + | 20% |
| COP-7 | ++ | + | 10% |
| COP-7 | +++ | ++ | 30% |
| COP-7 | ++ | ++ | 20% |
| COP-5 | +++ | ++ | 20% |

VI. Animal Efficacy Studies

Substantially pure osteogenic protein from bovine bone (BOP), BOP-rich osteogenic fractions having the properties set forth above, and several of the synthetic/recombinant proteins have been incorporated in matrices to produce osteogenic devices. The efficacy of bone-inducing potential of these devices was tested in cat and rabbit models, and found to be potent inducers of osteogenesis, ultimately resulting in formation of mineralized bone. The following sets forth guidelines as to how the osteogenic devices disclosed herein might be used in a clinical setting.

A. Feline Model

The purpose of this study is to establish a large animal efficacy model for the testing of the osteogenic devices of the invention, and to characterize repair of massive bone defects and simulated fracture non-union encountered frequently in the practice of orthopedic surgery. The study is designed to evaluate whether implants of osteogenic protein with a carrier can enhance the regeneration of bone following injury and major-reconstructive surgery by use of this large mammal model. The first step in this study design consists of the surgical preparation of a femoral osteotomy defect which, without further intervention, would consistently progress to non-union of the simulated fracture defect. The effects of implants of osteogenic devices into the created bone defects were evaluated by the following study protocol.

A-1. Procedure

Sixteen adult cats weighing less than 10 lbs. undergo unilateral preparation of a 1 cm bone defect in the right femur through a lateral surgical approach. In other experiments, a 2 cm bone defect was created. The femur is immediately internally fixed by lateral placement of an 8-hole plate to preserve the exact dimensions of the defect. There are three different types of materials implanted in the surgically created cat femoral defects: group I (n=3) is a control group which undergo the same plate fixation with implants of 4 M guanidine-HCl-treated (inactivated) cat demineralized bone matrix powder (GuHCl-DBM) (360 mg); group II (n=3) is a positive control group implanted with biologically active demineralized bone matrix powder (DBM) (360 mg); and group III (n=10) undergo a procedure identical to groups I-II, with the addition of osteogenic protein onto each of the GuHCl-DBM carrier samples. To summarize, the group III osteogenic protein-treated animals are implanted with exactly the same material as the group II animals, but with the singular addition of osteogenic protein.

All animals are allowed to ambulate ad libitum within their cages post-operatively. All cats are injected with tetracycline (25 mg/kg SQ each week for four weeks) for bone labelling. All but four group III animals are sacrificed four months after femoral osteotomy.

A-2. Radiomorphometrics

Figure 12:
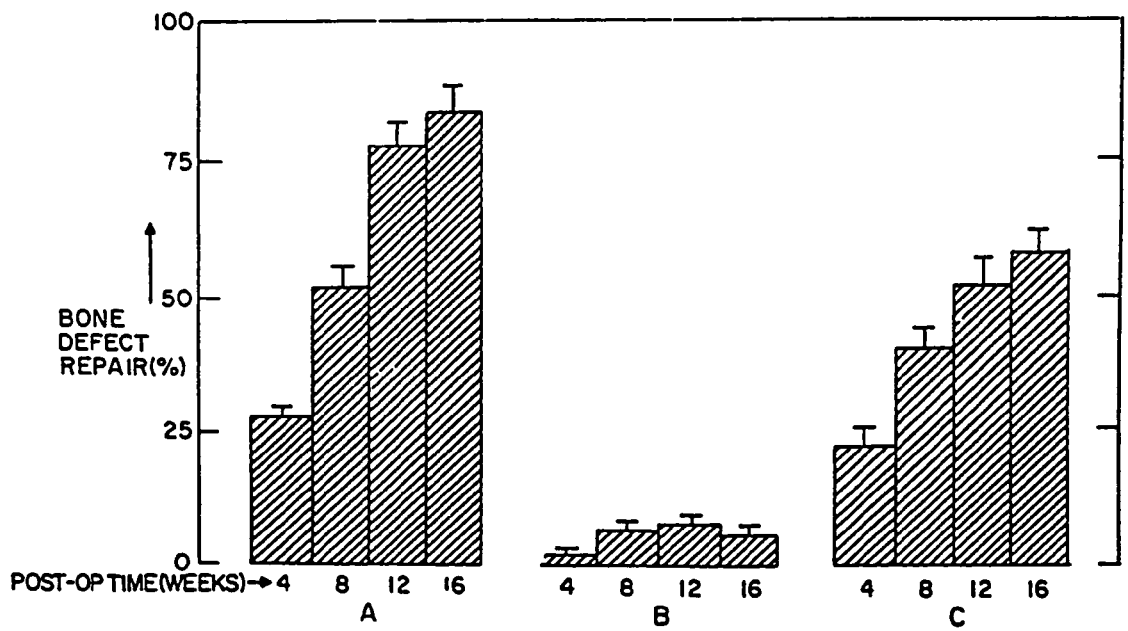
FIG. 12 is a bar graph of radiomorphometric analyses of feline bone defect repair after treatment with an osteogenic device (A), carrier control (B), and demineralized bone (C)

In vivo radiomorphometric studies are carried out immediately post-op at 4, 8, 12 and 16 weeks by taking a standardized x-ray of the lightly anesthesized animal positioned in a cushioned x-ray jig designed to consistently produce a true anterio-posterior view of the femur and the osteotomy site. All x-rays are taken in exactly the same fashion and in exactly the same position on each animal. Bone repair is calculated as a function of mineralization by means of random point analysis. A final specimen radiographic study of the excised bone is taken in two planes after sacrifice. X-ray results are shown in FIG. 12, and displaced as percent of bone defect repair. To summarize, at 16 weeks, 60% of the group III femors are united with average 86% bone defect regeneration. By contrast, the group I GuHCl-DMB negative-control implants exhibit no bone growth at four weeks, less than 10% at eight and 12 weeks, and 16% (±10%) at 16 weeks with one of the five exhibiting a small amount of bridging bone. The group II DMB positive-control implants exhibited 18% (±3%) repair at four weeks, 35% at eight weeks, 50% (±10%) at twelve weeks and 70% (±12%) by 16 weeks, a statistical difference of $p<0.01$ compared to osteogenic protein at every month. One of the three (33%) is united at 16 weeks.

A-3. Biomechanics

Excised test and normal femurs are immediately studied by bone densitometry, wrapped in two layers of saline-soaked towels, placed in two sealed plastic bags, and stored at −20° C. until further study. Bone repair strength, load to failure, and work to failure are tested by loading to failure on a specially designed steel 4-point bending jig attached to an Instron testing machine to quantitate bone strength, stiffness, energy absorbed and deformation to failure. The study of test femurs and normal femurs yield the bone strength (load) in pounds and work to failure in joules. Normal femurs exhibit a strength of 96 (±12) pounds. osteogenic protein-implanted femurs exhibited 35 (±4) pounds, but when corrected for surface area at the site of fracture (due to the "hourglass" shape of the bone defect repair) this correlated closely with normal bone strength. Only one demineralized bone specimen was available for testing with a strength of 25 pounds, but, again, the strength correlated closely with normal bone when corrected for fracture surface area.

A-4. Histomorphometry/Histology

Following biomechanical testing the bones are immediately sliced into two longitudinal sections at the defect site, weighed, and the volume measured. One-half is fixed for standard calcified bone histomorphometrics with fluorescent stain incorporation evaluation, and one-half is fixed for decalcified hemotoxylin/eosin stain histology preparation.

A-5. Biochemistry

Selected specimens from the bone repair site (n=6) are homogenized in cold 0.15 M NaCl, 3 mM $NaHCO_3$, pH 9.0 by a Spez freezer mill. The alkaline phosphatase activity of the supernatant and total calcium content of the acid soluble fraction of sediment are then determined.

A-6. Histopathology

The final autopsy reports reveal no unusual or pathologic findings noted at necropsy of any of the animals studied. Portion of all major organs are preserved for further study. A histopathological evaluation is performed on samples of the following organs: heart, lung, liver, both kidneys, spleen, both adrenals, lymph nodes, left and right quadriceps muscles at mid-femur (adjacent to defect site in experimental femur). No unusual or pathological lesions are seen in any of the tissues. Mild lesions seen in the quadriceps muscles are compatible with healing responses to the surgical manipulation at the defect site. Pulmonary edema is attributable to the euthanasia procedure. There is no evidence of any general systemic effects or any effects on the specific organs examined.

A-7. Feline Study Summary

The 1 cm and 2 cm femoral defect cat studies demonstrate that devices comprising a matrix containing disposed osteogenic protein can: (1) repair a weight-bearing bone defect in a large animal; (2) consistently induces bone formation shortly following (less than two weeks) implantation; and (3) induce bone by endochondral ossification, with a strength equal to normal bone, on a volume for volume basis. Furthermore, all animals remained healthy during the study and showed no evidence of clinical or histological laboratory reaction to the implanted device. In this bone defect model, there was little or no healing at control bone implant sites. The results provide evidence for the successful use of osteogenic devices to repair large, non-union bone defects.

B. Rabbit Model:

B1. Procedure and Results

Eight mature (less than 10 lbs) New Zealand White rabbits with epiphyseal closure documented by X-ray were studied. The purpose of this study is to establish a model in which there is minimal or no bone growth in the control animals, so that when bone induction is tested, only a strongly inductive substance will yield a positive result. Defects of 1.5 cm are created in the rabbits, with implantation of: osteogenic protein (n=5), DBM (n=8), GuHCl-DBM (n=6), and no implant (n=10). Six osteogenic protein implants are supplied and all control defects have no implant placed.

Of the eight animals (one animal each was sacrificed at one and two weeks), 11 ulnae defects are followed for the full course of the eight week study. In all cases (n=7) following osteo-periosteal bone resection, the no implant animals establish no radiographic union by eight weeks. All no implant animals develop a thin "Shell" of bone growing from surrounding bone present at four weeks and, to a slightly greater degree, by eight weeks. In all cases (n=4), radiographic union with marked bone induction is established in the osteogenic protein-implanted animals by eight weeks. As opposed to the no implant repairs, this bone repair is in the site of the removed bone.

Radiomorphometric analysis reveal 90% osteogenic protein-implant bone repair and 18% no-implant bone repair at sacrifice at eight weeks. At autopsy, the osteogenic protein bone appears normal, while "no implant" bone sites have only a soft fibrous tissue with no evidence of cartilage or bone repair in the defect site.

B-2. Allograft Device

In another experiment, the marrow cavity of the 1.5 cm ulnar defect is packed with activated osteogenic protein rabbit bone powder and the bones are allografted in an intercalary fashion. The two control ulnae are not healed by eight weeks and reveal the classic "ivory" appearance. In distinct contrast, the osteogenic protein-treated implants "disappear" radiographically by four weeks with the start of remineralization by six to eight weeks. These allografts heal at each end with mild proliferative bone formation by eight weeks.

This type of device serves to accelerate allograph repair.

B-3. Summary

These studies of 1.5 cm osteo-periosteal defects in the ulnae of mature rabbits show that: (1) it is a suitable model for the study of bone growth; (2) "no implant" or GuHCl negative control implants yield a small amount of periosteal-type bone, but not medullary or cortical bone growth; (3) osteogenic protein-implanted rabbits exhibited proliferative bone growth in a fashion highly different from the control groups; (4) initial studies show that the bones exhibit 50% of normal bone strength (100% of normal correlated vol:vol) at only eight weeks after creation of the surgical defect; and (5) osteogenic protein-allograft studies reveal a marked effect upon both the allograft and bone healing.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An isolated nucleic acid molecule comprising:
   (a) a first nucleic acid sequence consisting of nucleotides 1-1880 of SEQ ID NO: 40, and
   (b) a second nucleic acid sequence consisting of nucleotides 1882-4805 of SEQ ID NO: 40.

2. An isolated nucleic acid molecule comprising a nucleic acid sequence consisting essentially of nucleotides 15-305 of SEQ ID NO: 42, wherein said nucleic acid sequence encodes a protein competent to induce bone and cartilage formation in a mammal.

3. The isolated nucleic acid molecule of claim 1, wherein the nucleic acid is DNA.

4. The isolated nucleic acid molecule of claim 2, wherein the nucleic acid is DNA.

5. A host cell transformed with the nucleic acid molecule of claim 1.

6. A host cell transformed with the nucleic acid molecule of claim 2.

7. A host cell transformed with the nucleic acid molecule of claim 3.

8. A host cell transformed with the nucleic acid molecule of claim 4.

9. The host cell of claim 5, wherein the host cell is a prokaryotic or eukaryotic cell.

10. The host cell of claim 6, wherein the host cell is a prokaryotic or eukaryotic cell.

11. The host cell of claim 7, wherein the host cell is a prokaryotic or eukaryotic cell.

12. The host cell of claim 8, wherein the host cell is a prokaryotic or eukaryotic cell.

13. The host cell of claim 9, wherein said prokaryotic cell is an *E. coli* cell, and said eukaryotic cell is a *Saccharomyces* cell or a mammalian cell.

14. The host cell of claim 10, wherein said prokaryotic cell is an *E. coli* cell, and said eukaryotic cell is a *Saccharomyces* cell or a mammalian cell.

15. The host cell of claim 11, wherein said prokaryotic cell is an *E. coli* cell, and said eukaryotic cell is a *Saccharomyces* cell or a mammalian cell.

16. The host cell of claim 12, wherein said prokaryotic cell is an *E. coli* cell, and said eukaryotic cell is a *Saccharomyces* cell or a mammalian cell.

* * * * *